US012036311B2

(12) United States Patent
Furuta et al.

(10) Patent No.: US 12,036,311 B2
(45) Date of Patent: *Jul. 16, 2024

(54) ANTI-OBESITY AGENT, ANTI-DEMENTIA AGENT, DEODORANT, ANTI-AGING AGENT, ANTI-GLYCATION AGENT, ANTI-TYPE I ALLERGY AGENT, HYPOTENSIVE AGENT, FLAVOR IMPROVING AGENT, MUSCLE ENHANCING AGENT, AND BONE METABOLISM IMPROVING AGENT

(71) Applicant: Mitsui Sugar Co., Ltd., Tokyo (JP)

(72) Inventors: Toma Furuta, Tokyo (JP); Masami Mizu, Tokyo (JP); Kiyoaki Miyasaka, Tokyo (JP); Sayoko Fujii, Tokyo (JP); Kazuyo Shiomi, Tokyo (JP); Satoru Itou, Tokyo (JP); Miki Sakazaki, Tokyo (JP)

(73) Assignee: Mitsui Sugar Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/058,756

(22) PCT Filed: May 30, 2019

(86) PCT No.: PCT/JP2019/021592
§ 371 (c)(1),
(2) Date: Nov. 25, 2020

(87) PCT Pub. No.: WO2019/230907
PCT Pub. Date: Dec. 5, 2019

(65) Prior Publication Data
US 2021/0369597 A1  Dec. 2, 2021

(30) Foreign Application Priority Data

| May 30, 2018 | (JP) | 2018-103251 |
| May 30, 2018 | (JP) | 2018-103252 |
| May 30, 2018 | (JP) | 2018-103255 |
| May 30, 2018 | (JP) | 2018-103256 |
| Jun. 29, 2018 | (JP) | 2018-124544 |
| Jun. 29, 2018 | (JP) | 2018-124548 |
| Jul. 12, 2018 | (JP) | 2018-132453 |
| Aug. 2, 2018 | (JP) | 2018-146229 |
| Aug. 20, 2018 | (JP) | 2018-154039 |
| Nov. 29, 2018 | (JP) | 2018-223926 |
| Feb. 25, 2019 | (JP) | 2019-031756 |
| Apr. 1, 2019 | (JP) | 2019-070045 |
| Apr. 9, 2019 | (JP) | 2019-074154 |

(51) Int. Cl.
*A61K 8/9794* (2017.01)
*A61Q 15/00* (2006.01)

(52) U.S. Cl.
CPC ............ *A61K 8/9794* (2017.08); *A61Q 15/00* (2013.01); *A61K 2800/85* (2013.01)

(58) Field of Classification Search
None
See application file for complete search history.

(56) References Cited

U.S. PATENT DOCUMENTS

2010/0004185 A1    1/2010  Kanner et al.
2014/0357583 A1   12/2014  Ilag et al.
2021/0169764 A1*   6/2021  Wu ...................... A61Q 15/00

FOREIGN PATENT DOCUMENTS

| CN | 101188950 A | 5/2008 |
| CN | 102206691 A | 10/2011 |
| CN | 104957602 A | 10/2015 |
| CN | 109125341 A | 1/2019 |
| JP | H11-079971 A | 3/1999 |
| JP | H11-292776 A | 10/1999 |
| JP | 2000-217540 A | 8/2000 |
| JP | 2001-087365 A | 4/2001 |
| JP | 2001-299264 A | 10/2001 |
| JP | 2002-226323 A | 8/2002 |
| JP | 2002-338490 A | 11/2002 |
| JP | 2003-137803 A | 5/2003 |
| JP | 2003-265135 A | 9/2003 |
| JP | 2005-187430 A | 7/2005 |
| JP | 2006-219420 A | 8/2006 |
| JP | 2006-242835 A | 9/2006 |
| JP | 2010-503417 A | 2/2010 |
| JP | 2010-503609 A | 2/2010 |
| JP | 2010-070501 A | 4/2010 |
| JP | 2010-070541 A | 4/2010 |
| JP | 2010-083786 A | 4/2010 |
| JP | 2011-000428 A | 1/2011 |

(Continued)

OTHER PUBLICATIONS

Heinonen et al. (Advances in Chemical Engineering, vol. 42, Chapter 5 (2013)).*
Ju et al. (Carbohydrate Polymers 83 (2011) 591-599).*
Pei et al., "p-Coumaric acid and its conjugates: dietary sources, pharmacokinetic properties and biological activities," Journal of the Science of Food and Agriculture, 96: 2952-2962 (2018).
Furuta et al., "Technological development and demonstration to reduce GHG by manufacturing valuable substances from bagasse and molasses of domestic sugar mills," Proceedings of the Research Society of Japan Sugar Refineries Technologist, 63 (2017) (see English abstract).
Jiang et al., "Research on Strategies for More Valuable, Comprehensive Utilization of Sugarcane Bagasse," Light Industry Science and Technology, 11 (2013) (see English abstract).

(Continued)

*Primary Examiner* — Patricia Duffy
*Assistant Examiner* — Garen Gotfredson
(74) *Attorney, Agent, or Firm* — Morgan, Lewis & Bockius LLP

(57) ABSTRACT

One aspect of the present invention provides an anti-obesity agent, an anti-dementia agent, a deodorant, an anti-aging agent, an anti-glycation agent, an anti-type I allergy agent, a hypotensive agent, a flavor improving agent, a muscle enhancing agent, and a bone metabolism improving agent which contain a bagasse decomposition extract as an active ingredient.

14 Claims, 11 Drawing Sheets

(56) References Cited

FOREIGN PATENT DOCUMENTS

| | | |
|---|---|---|
| JP | 2013-213021 A | 10/2013 |
| JP | 2014-114289 A | 6/2014 |
| JP | 2015-528448 A | 9/2015 |
| JP | 2017-193947 A | 10/2017 |
| JP | 2018-027983 A | 2/2018 |
| JP | 2018-150240 A | 9/2018 |
| WO | 2007/037249 A1 | 4/2007 |
| WO | 2008/023266 A2 | 2/2008 |
| WO | 2008/034180 A1 | 3/2008 |
| WO | 2013/100105 A1 | 7/2013 |
| WO | 2014/032100 A1 | 3/2014 |
| WO | 2017/078175 A1 | 5/2017 |
| WO | 2019/028506 A1 | 2/2019 |

OTHER PUBLICATIONS

Suixin et al., "The Optimization of Extracting Xylan from Sugarcane Bagasses by Using Potassium Hydroxide and H2O2 and Analysis of Xylooligosaccharides Produced by Xylanase from Sugarcane Bagasse," Genomics and Applied Biology, 36 (9): 3863-38700 (2017) (see English abstract).

Xu et al., "Determination of cell wall ferulic and p-coumaric acids in sugarcane bagasse," Analytica Chimica Acta, 552: 207-217 (2005).

Zhenyu et al., "Progress in Understanding the Role of Polyphenol Compounds in Lipogenesis and Obesity," Food Science, 39 (19) (2017) (see English abstract).

Alam et al., "Hydroxycinnamic acid derivatives: a potential class of natural compounds for the management of lipid metabolism and obesity," Nutrition & Metabolism, 13: 27 (2016).

Zhao et al., "Crystallization of p-coumaric Acid from Sugarcane Bagasse Alkaline Hydrolysates," China Academic Journal Electronic Publishing House (2010) (see English abstract).

Takuma et al., "Behavioral analyses for learning and memory in mice and rats," Folia Pharmacol. Jpn. 130 (2): 112-116 (2007) (see partial English translation).

Furuta et al., "Verification of GHG reduction technique in manufacturing valuable products from waste of domestic sugar refinery," Proceedings of the Research Society of Japan Sugar Refineries' Technologists, 63: 7-10 (2017) (see English abstract).

Mitsubishi Chemical Corporation, Synthetic adsorbent (2017), http://www.diaion.com/products/synthesis_0201.html.

Shiomi et al., "Flavor-Improving Effects of a Sugar Cane Extract for Food," New Food Industry, 57 (6): 1-6 (2015) (see partial English translation).

Editorial department, "Trends in the Market for Food Ingredients Including Polyphenols," Food processing and Ingredients, 43 (6): 44-58 (2008) (see partial English translation).

Editorial department, "Trends in market for polyphenol foods and ingredients, where diversification of ingredients and function research are progressing," Food processing and ingredients, 44 (6): 49-59 (2009) (see partial English translation).

Miyazaki et al., "Verification of technique for manufacturing useful materials from bagasse," Proceedings for the Research Society of Japan Sugar Refineries' Technologists, 64: 1-4 (2018) (see English abstract).

Miyazaki et al., "Verification of technique for manufacturing useful materials from bagasse," Lecture Abstracts of the Research Society of Japan Sugar Refineries' Technologist, 5-8 (2018) (see partial English translation).

Yanai et al., "Effects of sugar cane-derived polymeric substances on intestinal environment," Lecture Abstracts of the Annual Meeting of Japan Society of Nutrition and Food Science, 255 (2016).

Sadowska-Bartosz et al., "Prevention of Protein Glycation by Natural Compounds," Molecules, 20: 3309-3334 (2015).

International Preliminary Report on Patentability and Written Opinion issued in corresponding International Patent Application No. PCT/JP2019/021592 dated Dec. 1, 2020.

International Search Report issued in corresponding International Patent Application No. PCT/JP2019/021592 dated Jul. 9, 2019.

Zheng et al., "Antioxidant/antihyperglycemic activity of phenolics from sugarcane (*Saccharum officinarum* L.) bagasse and identification by UHPLC-HR-TOFMS," Industrial Crops and Products, 101: 104-114 (2017).

Office Action issued in related U.S. Appl. No. 17/222,343 dated Jan. 20, 2023.

\* cited by examiner (a)

(b)

(c)

(d)

(a)

(b)

(c)

(a)

(b)

(c)

ANTI-OBESITY AGENT, ANTI-DEMENTIA AGENT, DEODORANT, ANTI-AGING AGENT, ANTI-GLYCATION AGENT, ANTI-TYPE I ALLERGY AGENT, HYPOTENSIVE AGENT, FLAVOR IMPROVING AGENT, MUSCLE ENHANCING AGENT, AND BONE METABOLISM IMPROVING AGENT

TECHNICAL FIELD

The present invention relates to an anti-obesity agent, an anti-dementia agent, a deodorant, an anti-aging agent, an anti-glycation agent, an anti-type I allergy agent, a hypotensive agent, a flavor improving agent, a muscle enhancing agent, and a bone metabolism improving agent.

BACKGROUND ART

Obesity, especially obesity due to visceral lipid accumulation is a cause of metabolic syndrome that has become a global health problem. Obesity in terms of a systematic mechanism refers to a state in which adipocytes accumulate a large amount of lipids and become enlarged and a state in which the number of enlarged adipocytes increases significantly.

Appropriate exercise and calorie intake restriction are effective in order to inhibit obesity, but in recent years, anti-obesity agents have been developed in order to inhibit obesity more efficiently. Patent Literature 1 discloses that a kiwi extract is effective in inhibiting obesity.

On the other hand, dementia refers to a state in which brain cells die or work poorly due to various causes, which results in various disorders that hinder living. Physical functions may also be lost due to atrophy of the entire brain with the onset of dementia.

Therefore, in recent years, studies on components that have an effect of inhibiting dementia have been actively conducted. For example, Patent Literature 2 discloses that royal jelly exhibits anti-dementia activity.

On the other hand, in recent years, deodorants used for eliminating or deodorizing bad odors generated from creatures such as humans and other animals, bad odors generated indoors, and from cars, refrigerators, toilets, barns, fish aquariums, factories, and the like, and bad odors generated from household waste and industrial wastes have become commercially available. On the other hand, in such deodorants, it is desired to use a deodorant derived from natural products even for environmental applications in consideration of the environment after disposal. Regarding the deodorant derived from natural products, Patent Literature 3 discloses a deodorant containing a sugar cane-derived distillate as an active ingredient.

On the other hand, the skin has a three-layer structure of the epidermis, dermis, and subcutaneous tissues. In the dermis, type I collagen accumulates to form a bundle and plays a role such as support of the dermis and components such as elastin and hyaluronic acid are present around the dermis. When the amount of these components is reduced or they decompose due to aging, UV irradiation, or the like, the skin becomes less tense and glossy and wrinkles are likely to be formed.

Various anti-aging agents have been studied in order to inhibit such skin aging. Patent Literature 4 discloses an anti-aging agent containing an extract from *Caragana* and/or *Camellia* oleifera as an active ingredient. Patent Literature 5 discloses an anti-aging agent containing an extract of one or more types of plants selected from among Podocarpaceae plants. Patent Literature 6 discloses an anti-aging agent containing a *Thymus quinquefolium* extract as an active ingredient. Patent Literature 7 discloses a collagen production promoting agent, a collagenase inhibitor, and an elastase inhibitor, which contain an extract from carambola leaves as an active ingredient.

On the other hand, glycation is also called the Maillard reaction, which is a non-enzymatic chemical reaction between amino acids or proteins and reducing sugars discovered by the French scientist L. C. Maillard in 1912. Glycation has been focused on in the field of food chemistry such as coloration, fragrance or flavor change that occurs during heating of food.

Glycation in the living body is a reaction in which carbonyl groups of a reducing sugar such as glucose react non-enzymatically with proteins, producing glycated proteins which are irreversible substances through Amadori transfer after formation of a Schiff base, and advanced glycation endproducts (AGEs) are produced through formation of a reaction intermediate mainly including carbonyl compounds such as 3-deoxyglucosone (3DG), glyoxal, methylglyoxal, glyceraldehyde, and glutaraldehyde.

In recent years, various studies regarding the relationship between AGEs, and human skin aging, arteriosclerosis, diabetic diseases, three major diabetes complications (neuropathy, retinopathy, nephropathy), adult diseases and the like have been conducted, and anti-glycation agents are used for treatment and amelioration of these diseases, aging prevention, and preventive measures. Thus, various anti-glycation agents have been proposed so far. For example, Patent Literature 8 discloses an anti-glycation agent containing a Shochu residue concentrated extract as an active ingredient.

On the other hand, allergy is defined as "living body systematic or local disorder based on immune responses." Allergic reactions can be classified into type I to type IV. Among these, types I, II, and III allergies are humoral immunity involving serum antibodies and type IV allergies are cellular immunity with sensitized lymphocytes.

Type I allergies are also called immediate allergies or anaphylactic allergies. Symptoms of type I allergies include, for example, hay fever and urticaria, and since the number of people with these symptoms is relatively large, effective anti-type I allergy agents are required. For example, Patent Literature 9 discloses a cosmetic or skin external preparation having an anti-allergic effect by using a carnitine derivative and/or a carnitine derivative in combination with an effect-promoting agent.

On the other hand, hypertension is a state in which a blood pressure exceeding a normal range is maintained. Hypertension is one lifestyle-related disease and causes complications in major organs such as the brain, heart, and kidneys, which has become a big problem.

In recent years, naturally derived substances having an antihypertensive action have been searched for. For example, Patent Literature 10 discloses a hypotensive agent containing a mung bean decomposition product.

On the other hand, in the related art, flavor improving agents that selectively eliminate or reduce unpleasant flavors of foods and drinks such as bitterness, astringency, sourness, grassy smelling tastes, astringent tastes, irritating tastes, metallic tastes, and retort odors are known. For example, Patent Literature 11 discloses a food and drink flavor improving agent which contains a sugar cane-derived distillate as an active ingredient and which is a fraction obtained by allowing a distillate obtained by distilling a sugar cane juice to pass through a column filled with a synthetic adsorbing agent as a fixed carrier, and eluting a component adsorbed on the synthetic adsorbing agent in a solvent selected from among water, ethanol and a mixture thereof. In addition, Patent Literature 12 discloses a method of adding a sugar cane-derived extract as an active ingredient to foods and drinks and improving flavors of the foods and drinks, and in which a sugar cane-derived extract is a fraction obtained by treating raw materials selected from among sugar cane juice, a sugar cane solvent extract solution and sugar cane-derived molasses through column chromatography using a fixed carrier, and improving of flavors of foods and drinks is any of improving salt flavors of salt-containing foods and drinks, improving egg flavors of egg-containing foods and drinks, and improving fragrance flavors of fragrance-containing foods and drinks.

On the other hand, muscles are formed by differentiation of myocytes. In differentiation of myocytes, myoblasts, which are progenitor cells, proliferate to reach a certain number of cells, move to a scheduled muscle area, and fuse with each other to become differentiated polygonal myotube cells. Then, genes representing muscle-specific properties such as muscle contraction proteins and specific enzymes are expressed in myotube cells to construct a muscle contraction system.

Mitochondria in myocytes are also closely involved in muscle functions. The main function of mitochondria is energy (ATP) production in the TCA cycle. In order to improve a metabolic function of muscle, it is important to increase an amount of mitochondria or their activity.

Since enhancing muscles and improving their functions are important for maintaining and promoting motor functions and maintaining physical health, various muscle enhancing methods are being investigated. For example, Patent Literature 13 discloses a muscle differentiation-inducing promoting agent containing a rice bran and/or rice germ fermented extract as an active ingredient. In addition, Patent Literature 14 discloses a method of activating mitochondria during exercise using glutathione.

On the other hand, bone is reconstructed (bone remodeling) by repeated bone metabolism of "bone formation" with osteoblasts (cells that make bone) and "bone resorption" with osteoclasts (cells that break down bone) and bone mass is maintained by the balance of these two cells. Osteoblasts are derived from mesenchymal stem cells like lipid and muscle cells, but osteoclasts are derived from blood cells like red blood cells and white blood cells.

Bone metabolism starts when membrane proteins called RANKL appear on the surface of osteoblasts. When RANKL binds to a receptor called RANK which is a blood cell, blood cells differentiate into osteoclasts. Differentiated and mature osteoclasts break down bone (bone resorption), and osteoblasts then form the same amount of bone as the amount of osteoblasts absorbed. However, the balance of bone metabolism (balance between bone resorption and bone formation) is destroyed due to factors such as aging and deterioration in ovarian function, and the bone mass (bone density) decreases and thus bone-related diseases such as fracture, osteoporosis, and osteomalacia occur.

Thus, there is a demand for a component useful for inhibiting bone-related diseases by improving bone metabolism including bone formation and bone resorption. For example, Patent Literature 15 discloses a bone formation promoting agent containing at least one of a *Euterpe oleracea* extract and an *Actinidia polygama* extract as an active ingredient.

CITATION LIST

Patent Literature

[Patent Literature 1] Japanese Unexamined Patent Publication No. 2010-503609
[Patent Literature 2] PCT International Publication No. WO2017/078175
[Patent Literature 3] Japanese Unexamined Patent Publication No. 2001-087365
[Patent Literature 4] Japanese Unexamined Patent Publication No. 2010-83786
[Patent Literature 5] Japanese Unexamined Patent Publication No. 2010-70501
[Patent Literature 6] Japanese Unexamined Patent Publication No. H11-79971
[Patent Literature 7] Japanese Unexamined Patent Publication No. 2002-226323
[Patent Literature 8] Japanese Unexamined Patent Publication No. 2013-213021
[Patent Literature 9] Japanese Unexamined Patent Publication No. 2014-114289
[Patent Literature 10] Japanese Unexamined Patent Publication No. 2006-219420
[Patent Literature 11] Japanese Unexamined Patent Publication No. 2001-299264
[Patent Literature 12] Japanese Unexamined Patent Publication No. 2003-265135
[Patent Literature 13] Japanese Unexamined Patent Publication No. 2017-193947
[Patent Literature 14] Japanese Unexamined Patent Publication No. 2018-27983
[Patent Literature 15] Japanese Unexamined Patent Publication No. 2018-150240

Non-Patent Literature

[Non-Patent Literature 1] Folia Pharmacol. Jpn., vol. 130, No. 2, 2007, p 112-p 116

SUMMARY OF INVENTION

Problems to be Solved by the Invention

An object of the present invention is to provide a novel anti-obesity agent, anti-dementia agent, deodorant, anti-aging agent, anti-glycation agent, anti-type I allergy agent, hypotensive agent, flavor improving agent, muscle enhancing agent, and bone metabolism improving agent.

Means for Solving the Problems

The inventors have found by an in vitro test that a bagasse decomposition extract has an obesity inhibiting action, an anti-aging action, an anti-glycation action, an anti-type I allergic action, an antihypertensive action, a muscle enhancing action, and a bone metabolism improving action.

The inventors have found by an in vivo test that a bagasse decomposition extract has an action of improving short-term memory disorders due to accumulation of amyloid β proteins.

The inventors have also found that a bagasse decomposition extract has an excellent deodorant action and particularly a food and drink deodorant action. In addition, the inventors have found that a bagasse decomposition extract has a flavor improving effect on foods and drinks different from components described in Patent Literature 11 and 12.

A first aspect of the present invention provides, as one aspect, an anti-obesity agent comprising a bagasse decomposition extract as an active ingredient. According to the anti-obesity agent of the present invention, it is possible to effectively inhibit obesity.

The anti-obesity agent of the present invention may be based on at least a lipid accumulation inhibitory action. The anti-obesity agent of the present invention has an action of inhibiting accumulation of lipids in at least adipocytes. Since inhibiting excess lipid accumulation can be an effective method for preventing obesity, the anti-obesity agent of the present invention inhibits obesity.

A first aspect of the present invention provides a lipid accumulation inhibiting agent comprising a bagasse decomposition extract as an active ingredient.

A second aspect of the present invention provides an anti-dementia agent comprising a bagasse decomposition extract as an active ingredient.

A second aspect of the present invention provides a short-term memory disorder improving/inhibiting agent comprising a bagasse decomposition extract as an active ingredient.

A third aspect of the present invention provides a deodorant comprising a bagasse decomposition extract as an active ingredient.

A fourth aspect of the present invention provides an anti-aging agent comprising a bagasse decomposition extract as an active ingredient. The anti-aging agent of the present invention contains a bagasse decomposition extract as an active ingredient and thus has an excellent anti-aging effect.

A fourth aspect of the present invention can provide, as another aspect, an extracellular matrix decomposition enzyme inhibitor comprising a bagasse decomposition extract as an active ingredient. The fourth aspect of the present invention can provide, as still another aspect, a fibroblast activator.

A fifth aspect of the present invention relates to an anti-glycation agent comprising a bagasse decomposition extract as an active ingredient. Since the anti-glycation agent of the present invention contains a bagasse decomposition extract as an active ingredient, it has excellent anti-glycation activity.

Since the anti-glycation agent has excellent anti-glycation activity, it can be appropriately used for an anti-glycation food and drink.

A sixth aspect of the present invention provides, as one aspect, an anti-type I allergy agent comprising a bagasse decomposition extract as an active ingredient. According to the anti-type I allergy agent of the present invention, it is possible to inhibit (treat, alleviate or prevent) symptoms of type I allergy.

The anti-type I allergy agent of the present invention may be based on the degranulation inhibitory action of mast cells or basophils.

The mechanism of the type I allergic reaction is as follows.
(1) When an antigen (allergen) such as pollen or a tick enters a living body, helper T cells (Th2 cell) issue a command to differentiate B cells into immunoglobulin E (IgE) antibody-producing cells.
(2) IgE antibodies specific to antigens thereof are produced from IgE antibody-producing cells.
(3) IgE antibodies bind to mast cells or basophils, and antigens bind thereto again and thus chemical mediators such as histamine and leukotriene are secreted (degranulated), and allergic symptoms are exhibited.

The anti-type I allergy agent of the present invention has an action of inhibiting at least mast cell or basophil degranulation. Therefore, according to the anti-type I allergy agent of the present invention, it is possible to effectively inhibit symptoms of type I allergy.

A sixth aspect of the present invention can provide, as another aspect, a mast cell or basophil degranulation inhibiting agent containing a bagasse decomposition extract as an active ingredient.

A seventh aspect of the present invention provides, as one aspect, a hypotensive agent comprising a bagasse decomposition extract as an active ingredient. The hypotensive agent of the present invention contains a bagasse decomposition extract as an active ingredient and thus has an excellent antihypertensive effect.

A seventh aspect of the present invention can provide, as another aspect, an angiotensin converting enzyme inhibitor comprising a bagasse decomposition extract as an active ingredient.

An eighth aspect of the present invention provides a flavor improving agent comprising a bagasse decomposition extract. The flavor improving agent may be a flavor improving agent that enhances preferred flavors of foods and drinks. The flavor improving agent may be a flavor improving agent that reduces unpleasant flavors of foods and drinks.

An eighth aspect of the present invention can provide foods and drinks comprising the above flavor improving agent.

The eighth aspect of the present invention can provide a preferred flavor enhancing agent for foods and drinks, comprising a bagasse decomposition extract. The eighth aspect of the present invention can also provide an unpleasant flavor reducing agent for foods and drinks, comprising a bagasse decomposition extract.

A ninth aspect of the present invention provides a muscle enhancing agent comprising a bagasse decomposition extract as an active ingredient.

The ninth aspect of the present invention can also provide a myotube cell differentiation promoting agent comprising a bagasse decomposition extract as an active ingredient. The ninth aspect of the present invention can also provide a mitochondrial activator comprising a bagasse decomposition extract as an active ingredient.

A tenth aspect of the present invention provides a bone metabolism improving agent comprising a bagasse decomposition extract as an active ingredient.

The tenth aspect of the present invention can also provide a bone formation promoting agent comprising a bagasse decomposition extract as an active ingredient. The tenth aspect of the present invention can also provide a bone resorption inhibiting agent comprising a bagasse decomposition extract as an active ingredient.

The bagasse decomposition extract in the present invention may be a decompoed liquid obtained by at least one decomposition treatment selected from the group consisting of an alkaline treatment, a hydrothermal treatment, an acid treatment, a sub-critical water treatment and a blasting treatment.

The bagasse decomposition extract may be a fraction obtained by allowing a decompoed liquid to pass through a column filled with a fixed carrier. The fixed carrier is preferably a synthetic adsorbing agent or an ion exchange resin.

When the fixed carrier is a synthetic adsorbing agent, the bagasse decomposition extract may be a fraction obtained by eluting a component adsorbed on the synthetic adsorbing agent in at least one solvent selected from the group consisting of water, methanol, ethanol and a mixture thereof.

The synthetic adsorbing agent is preferably an aromatic resin, an acrylic acid-based methacrylic resin, or an acrylonitrile aliphatic resin.

The bagasse decomposition extract may be a fraction obtained by allowing a decompoed liquid to pass through a column filled with a synthetic adsorbing agent as a fixed carrier and eluting a component adsorbed on the synthetic adsorbing agent in a mixed solvent of ethanol and water, and in this case, the synthetic adsorbing agent is an unsubstituted aromatic resin, the temperature of the column is 20 to 60° C., and the volume ratio of ethanol and water in the mixed solvent (ethanol/water) may be 50/50 to 60/40.

Effects of the Invention

According to the present invention, it is possible to provide a novel anti-obesity agent, anti-dementia agent, deodorant, anti-aging agent, anti-glycation agent, anti-type I allergy agent, hypotensive agent, flavor improving agent, muscle enhancing agent, and bone metabolism improving agent.

EMBODIMENTS FOR CARRYING OUT THE INVENTION

Figure 1:
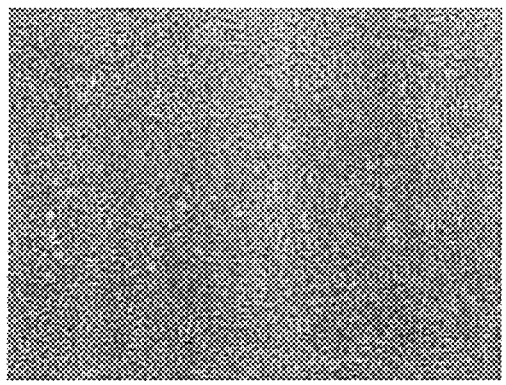
FIG. 1 shows microscopic images of results obtained by staining accumulated lipid droplets in progenitor cells (undifferentiated a1-1), and adipocytes of Positive Control a1-1, Comparative Example a1-1 and Example a1.
Figure 1:
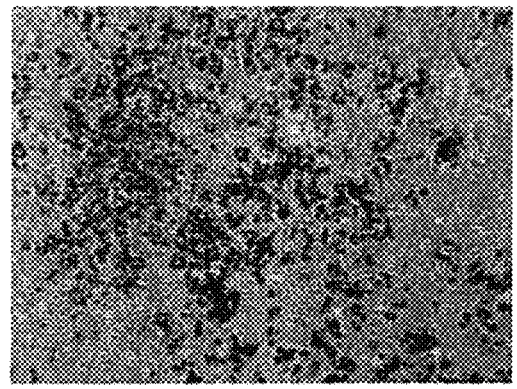
Figure 1:
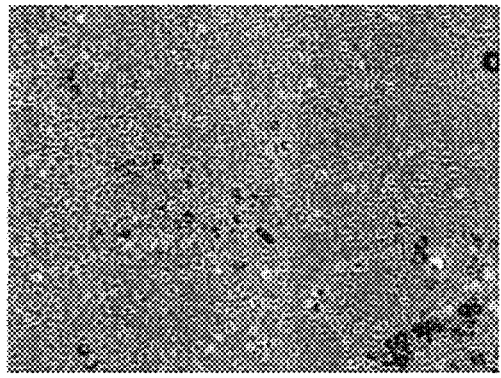
Figure 1:
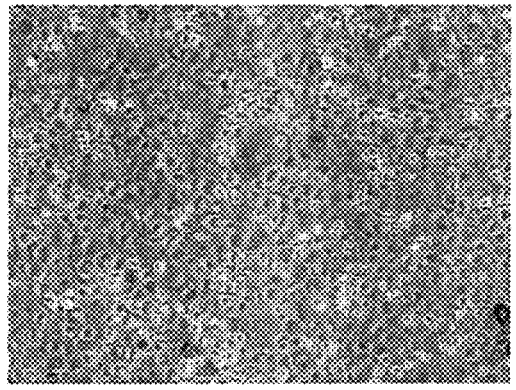

Embodiments of the present invention will be described below. However, the present invention is not limited to the following embodiments.

<Bagasse Decomposition Extract>

"Bagasse" typically refers to bagasse that is discharged during a sugar production procedure in a raw sugar production process. The bagasse discharged in the sugar production procedure in raw sugar factories includes not only final bagasse that has left a final squeezer but also finely divided sugar cane that has been cut into subsequent squeezers including the first squeezer. A suitable bagasse is bagasse that is discharged after sugar juice is squeezed in a squeezing process in raw sugar factories. Bagasses have different water contents, sugar contents and composition ratios thereof depending on the type of sugar cane, a harvesting period, and the like, but in the present invention, these bagasses can be arbitrarily used. In addition, in one embodiment, regarding the raw material bagasse, as in a raw sugar factory, for example, bagasse remaining after sugar cane squeezing discharged in a brown sugar production factory or bagasse after a sugar solution from sugar cane is squeezed according to small-scale laboratory level implementation can be used.

In one embodiment, the bagasse decomposition extract may be a bagasse (and/or its processed product) decompoed liquid. The decompoed liquid can be obtained by at least one decomposition treatment selected from the group consisting of an alkaline treatment, a hydrothermal treatment, an acid treatment, a sub-critical water treatment and a blasting treatment. The bagasse decomposition treatment in this specification requires that a part or all of the chemical structure of lignin, cellulose, and/or hemicellulose be destroyed. The decomposition treatment is preferably an alkaline treatment or a hydrothermal treatment because a bagasse decomposition extract is easily obtained.

The alkaline treatment may be a treatment in which an alkaline solution is brought into contact with bagasse. Examples of a method of bringing into contact with an alkaline solution include a method of sprinkling an alkaline solution on bagasse and a method of immersing bagasse in an alkaline solution. In the method of immersing bagasse in an alkaline solution, a mixture containing bagasse and an alkaline solution may be immersed with stirring.

Examples of alkaline solutions include a sodium hydroxide aqueous solution, a potassium hydroxide aqueous solution, and an ammonia aqueous solution. Regarding the alkaline solution, these solutions may be used alone or two or more thereof may be used in combination. The alkaline solution is preferably a sodium hydroxide aqueous solution because it is inexpensive and easily used in a food producing process.

The temperature (liquid temperature) of the alkaline solution is preferably 40° C. or higher, more preferably 100° C. or higher, and still more preferably 130° C. or higher in order to shorten the treatment time of the decomposition treatment. The temperature of the alkaline solution is preferably 250° C. or lower, more preferably 200° C. or lower, and still more preferably 150° C. or lower in order to prevent polysaccharides from remaining in the decompoed liquid. The temperature of the alkaline solution may be 40 to 250° C., 40 to 200° C., 40 to 150° C., 100 to 250° C., 100 to 200° C., 100 to 150° C., 130 to 250° C., 130 to 200° C., or 130 to 150° C.

The alkaline treatment may be performed under atmospheric pressure or may be performed under pressurization. In the case of pressurizing, the pressure may be 0.1 MPa or more or 0.2 MPa or more, and may be 4.0 MPa or less, 1.6 MPa or less, or 0.5 MPa or less. The pressure may be 0.1 to 4.0 MPa, 0.1 to 1.6 MPa, 0.1 to 0.5 MPa, 0.2 to 4.0 MPa, 0.2 to 1.6 MPa, or 0.2 to 0.5 MPa.

The hydrothermal treatment may be a treatment in which high temperature water or water vapor is brought into contact with bagasse under a high pressure. More specifically, the hydrothermal treatment may be, for example, a method in which water is added so that the solid concentration of the bagasse is 0.1 to 50%, and a decomposition treatment is performed under high temperature and high pressure conditions. The temperature of water or water vapor is preferably 130 to 250° C., and an applied pressure is preferably a pressure 0.1 to 0.5 MPa higher than a saturated water vapor pressure of water at each temperature.

The acid treatment may be a treatment in which an acidic solution is brought into contact with bagasse. Examples of acidic solutions include dilute sulfuric acid. The method of bringing an acidic solution into contact with bagasse, and conditions regarding the temperature of the acid solution in the acid treatment and the pressure in the acid treatment may be the same method and conditions as in the above alkaline treatment.

The sub-critical water treatment may be a treatment in which subcritical water is brought into contact with bagasse. The method of bringing subcritical water into contact with bagasse may be the same as in the above alkaline treatment method. Sub-critical water treatment conditions are not particularly limited, but it is preferable that the temperature of sub-critical water be 160 to 240° C., and the treatment time be 1 to 90 minutes.

The blasting treatment may be a treatment in which insoluble xylan contained in the bagasse is decomposed to some extent in the hydrothermal treatment, and a valve provided in a pressure-resistant reaction container is then opened at once and thus the bagasse is crushed by instantaneously releasing it to atmospheric pressure.

In the decompoed liquid, after the above decomposition treatment, a treatment for separating the solid content and the liquid content may be performed. In this case, the liquid content obtained after separation can be used as a decompoed liquid. A method for separating the solid content and the liquid content may be separation using a strainer, filtration, centrifugation, decantation, or the like.

In the decompoed liquid, polymer components such as polysaccharides may be removed by membrane separation or the like. In this case, the liquid content after membrane separation can be used as a decompoed liquid. The separation membrane is not particularly limited as long as it is an ultrafiltration membrane (UF membrane). The molecular weight cutoff of the ultrafiltration membrane is preferably 2,500 to 50,000 and more preferably 2,500 to 5,000.

Regarding the material for the ultrafiltration membrane, polyimide, polyethersulfone (PES), polysulfone (PS), polyacrylonitrile (PAN), polyvinylidene fluoride (PVDF), regenerated cellulose, cellulose, cellulose esters, sulfonated polysulfone, sulfonated polyethersulfone, polyolefins, polyvinyl alcohol, polymethylmethacrylate, polytetrafluoroethylene, and the like can be used.

An ultrafiltration membrane filtration method may be a dead end filtration or a cross flow filtration. In consideration of membrane fouling inhibition, a cross flow filtration is preferable.

Regarding the membrane form of the ultrafiltration membrane, an appropriate form such as a flat membrane type, a spiral type, a tubular type, and a hollow fiber type can be used. More specific examples thereof include GE series, GH series, GK series, PW type, and HWSUF type (commercially available from SUEZ), HFM-180, HFM-183, HFM-251, HFM-300, HFK-131, HFK-328, MPT-U20, MPS-U20P, and MPS-U20S (commercially available from KOCH), SPE1, SPE3, SPE5, SPE10, SPE30, SPV5, SPV50, and SOW30 (commercially available from Synder), Microza (registered trademark) UF series with a molecular weight cutoff of 3,000 to 10,000 (commercially available from Asahi Kasei Corporation), and NTR7410 and NTR7450 (commercially available from Nitto Denko Corporation).

In another embodiment, the bagasse decomposition extract may be a fraction obtained by allowing the above decompoed liquid to pass through a column filled with a fixed carrier. When the decompoed liquid is allowed to pass through a column, the active ingredient in the decompoed liquid is adsorbed on the fixed carrier and most sugars and inorganic salts flow out directly.

When the above decompoed liquid passes through the column, the decompoed liquid can be passed directly through the column or can be passed through the column after having its concentration adjusted to an arbitrary level with water. In the decompoed liquid, the pH may be adjusted before the liquid passes through the column. In order to improve the adsorption rate, when the fixed carrier is a synthetic adsorbing agent, the pH of the decompoed liquid is preferably adjusted to 6 or less. The pH of the decompoed liquid may be more than 4.5 and 6 or less. When the fixed carrier is an ion exchange resin, the pH of the decompoed liquid is preferably adjusted to 5 or more.

The fixed carrier is preferably either a synthetic adsorbing agent or an ion exchange resin.

The synthetic adsorbing agent is preferably a synthetic porous adsorbing agent. Regarding the synthetic adsorbing agent (synthetic porous adsorbing agent), an organic resin is preferably used. The organic resin is preferably at least one selected from the group consisting of an aromatic resin, an acrylic acid-based methacrylic resin, and an acrylonitrile aliphatic resin.

Examples of aromatic resins include a styrene-divinylbenzene resin. Examples of aromatic resins include porous resins such as an aromatic resin having a hydrophobic substituent, an unsubstituted aromatic resin, and an aromatic resin specially treated to be a non-substituted group type. Among these, an unsubstituted aromatic resin or an aromatic resin specially treated to be a non-substituted group type is preferable.

Examples of commercially available synthetic adsorbing agents include DIAION (trademark) HP-10, HP-20, HP-21, HP-30, HP-40, and HP-50 (which are all unsubstituted aromatic resins, product name, commercially available from Mitsubishi Chemical Corporation); SP-825, SP-800, SP-850, SP-875, SP-70, and SP-700 (which are all aromatic resins specially treated to be a non-substituted group type, product name, commercially available from Mitsubishi Chemical Corporation); SP-900 (aromatic resin, product name, commercially available from Mitsubishi Chemical Corporation); Amberlite (trademark) XAD-2, XAD-4, XAD-16, and XAD-2000 (which are all aromatic resins, product name, commercially available from Organo Corporation); DIAION (trademark) SP-205, SP-206, and SP-207 (which are all aromatic resins having a hydrophobic substituent, product name, commercially available from Mitsubishi Chemical Corporation); HP-2MG and EX-0021 (which are all aromatic resins having a hydrophobic substituent, product name, commercially available from Mitsubishi Chemical Corporation); Amberlite (trademark) XAD-7 and XAD-8 (which are all acrylic acid ester resins, product name, commercially available from Organo Corporation); DIAION (trademark) HP1MG and HP2MG (which are all acrylic acid methacrylic resins, product name, commercially available from Mitsubishi Chemical Corporation); and Sephadex (trademark) LH20 and LH60 (which are all crosslinked dextran derivatives, product name, commercially available from Pharmacia Biotech Co., Ltd.). Among these, an unsubstituted aromatic resin (for example, HP-20) or an aromatic resin specially treated to be a non-substituted group type (for example, SP-850) is preferable.

The amount of the synthetic adsorbing agent filled into the column can be appropriately determined depending on the size of the column, the type of the synthetic adsorbing agent, and the like.

When the synthetic adsorbing agent is used as a fixed carrier, the liquid flow velocity when the decompoed liquid passes through can be appropriately changed depending on the size of the column, the type of the elution solvent, the type of the synthetic adsorbing agent, and the like, and SV=1 to 30 hours$^{-1}$ is preferable. Here, SV (space velocity, space rate) is a unit of how many times the amount of the liquid in the resin capacity is passed per hour.

The adsorbed component (active ingredient) adsorbed on the synthetic adsorbing agent can be eluted in a solvent (elution solvent). In order to collect the adsorbed component more efficiently, sugars and inorganic salts remaining in the column are preferably washed off with water before the adsorbed component is eluted. In this case, the eluted component can be used as a bagasse decomposition extract.

When the synthetic adsorbing agent is used as a fixed carrier, the elution solvent may be at least one selected from the group consisting of water, methanol, ethanol and a mixture thereof. The elution solvent is preferably a mixed solvent of an alcohol and water, and more preferably a mixed solvent of ethanol and water, and in order for the adsorbed component to be eluted more efficiently at room temperature, a mixed solvent of ethanol and water having a volume ratio of 50/50 to 60/40 (ethanol/water) is still more preferable.

When the synthetic adsorbing agent is used as a fixed carrier, the temperature of the column during elution (column temperature) may be room temperature, but when the column temperature is raised to a temperature higher than room temperature, the mixing proportion of ethanol in the mixed solvent of ethanol and water can be reduced, and the adsorbed component can be eluted more efficiently. The temperature is preferably 20 to 60° C. and more preferably 40 to 60° C. The inside of the column may be under an atmospheric pressure condition or under a pressure condition.

When the synthetic adsorbing agent is used as a fixed carrier, the elution rate can be appropriately set depending on the size of the column, the type of the elution solvent, the type of the synthetic adsorbing agent, and the like, and SV=0.1 to 10 hours' is preferable.

Ion exchange resins are classified into a gel type resin and a porous resin such as a porous type, a microporous type or high porous type based on the form of the resin, and the ion exchange resin is not particularly limited. The ion exchange resin is preferably an anion exchange resin. Regarding the anion exchange resin, a strongly basic anion exchange resin or a weakly basic anion exchange resin may be used. When an alkaline treatment liquid is used as a raw material, a strongly basic anion exchange resin is preferably used, but when a decompoed liquid is used as a raw material in other treatments, there is no particular limitation.

Examples of commercially available strongly basic anion exchange resins include DIAION (trademark) PA306, PA308, PA312, PA316, PA318L, HPA25, SA10A, SA12A, SA11A, SA20A, and UBA120 (which are commercially available from Mitsubishi Chemical Corporation), Amberlite (trademark) IRA400J, IRA402B1, IRA404J, IRA900J, IRA904, IRA458RF, IRA958, IRA410J, IRA411, and IRA910CT (which are commercially available from Organo Corporation), and DOWEX (trademark) Marathon A, Marathon MSA, MONOSPHERE 550A, and Marathon A2 (which are commercially available from Dow Chemical Japan Co., Ltd.).

The amount of the ion exchange resin filled into the column can be appropriately determined depending on the size of the column, the type of the ion exchange resin, and the like, and is preferably 2 to 10,000 times the wet volume, and more preferably 5 to 500 times the wet volume with respect to the solid content of the decompoed liquid.

The liquid passing conditions can be appropriately set depending on the type of the pretreatment liquid, the type of the ion exchange resin, and the like. Preferably, the flow rate is SV=0.3 to 30 hours$^{-1}$, and the amount of liquid to be passed is 100 to 300 volume % of the ion exchange resin, and the column temperature is 40 to 90° C. The inside of the column may be at atmospheric pressure or in a pressurized state.

When the ion exchange resin is used as a fixed carrier, the bagasse decomposition extract may be a fraction obtained by allowing a liquid to pass through a column filled with an ion exchange resin and eluting it in an eluent such as an aqueous solution containing a salt, an acid, an alcohol or a mixture thereof. In this case, the eluent may be degassed.

In one embodiment, the bagasse decomposition extract may be a concentrate obtained by concentrating the above decompoed liquid or fraction. The concentration method may be a known method, for example, a method such as solvent distillation under a reduced pressure and freeze-drying. During concentrating, the decompoed liquid or fraction can be concentrated 15 to 30 times, and the concentrated component can be used as a bagasse decomposition extract.

The bagasse decomposition extract can be obtained, for example, as follows. A 1 mass % sodium hydroxide aqueous solution is added to the bagasse so that the solid concentration is 0.1 to 50%, and boiling is performed at 100° C. to obtain a decompoed liquid (alkaline treatment liquid). The decompoed liquid is ultrafiltered with an UF membrane with a molecular weight cutoff of 2,500 to 5,000, adjustment is performed such that the obtained filtrate becomes acidic and it is then passed through the column filled with an unsubstituted aromatic resin at a column temperature of 20 to 60° C. Then, components adsorbed on the column are eluted at a column temperature of 20 to 60° C. in a mixed solvent of ethanol and water (elution solvent) having a volume ratio of 50/50 to 60/40 (ethanol/water), and an eluted fraction in which the amount of eluate recovered from when elution in a mixed solvent of ethanol and water starts is within the amount 45 times the wet volume of the aromatic resin is collected. The collected fraction (fraction containing components having a bone metabolism improving action) can be recovered and concentrated by a general method (solvent distillation under a reduced pressure, freeze-drying, and the like) to obtain the bagasse decomposition extract. The bagasse decomposition extract obtained in this manner can be stored as a liquid or powder extract that is concentrated so that the solid content is 30 mass % or more. When the extract is a liquid, the extract is preferably stored in a refrigerator.

As another example, the bagasse decomposition extract can be obtained, for example, as follows. That is, water is added to the bagasse so that the solid concentration is 0.1 to 50%, a hydrothermal treatment is performed using water at 130 to 250° C. under a pressure of 0.2 to 4.0 MPa, and a decompoed liquid (hydrothermal treatment liquid) is obtained by solid-liquid separation by filtration. The obtained hydrothermal treatment liquid is caused to pass through a column filled with an aromatic resin specially treated to be a non-substituted group type at a temperature of 20 to 60° C., and components adsorbed on the column are then eluted at a column temperature of 20 to 60° C. in a mixed solvent of ethanol and water (elution solvent) having a volume ratio of 50/50 to 60/40 (ethanol/water), and an eluted fraction in which the amount of eluate recovered from when elution in a mixed solvent of ethanol and water starts is within the amount 5 times the wet volume of the aromatic resin is collected. The collected fraction (fraction containing components having a bone metabolism improving action) can be recovered and concentrated by a general method (solvent distillation under a reduced pressure, freeze-drying, and the like) to obtain the bagasse decomposition extract. The bagasse decomposition extract obtained in this manner can be stored as a liquid or powder extract that is concentrated so that the solid content is 30 mass % or more. When the extract is a liquid, the extract is preferably stored in a refrigerator.

The bagasse decomposition extracts in the above embodiments may be a liquid or powder. The powder bagasse decomposition extract can be produced using, for example, a liquid bagasse decomposition extract by using a spray drying method, a freeze-drying method, a fluidized bed granulation method, a powdering method using an excipient, or the like.

The bagasse decomposition extract preferably contains phenylpropanoids such as p-coumaric acid, ferulic acid, caffeic acid and vanillin, and at least one selected from the group consisting of lignin and a decomposition product thereof.

First Embodiment: Anti-Obesity Agent

The anti-obesity agent in this specification is a composition having an obesity inhibiting action. The obesity inhibiting action may be, for example, an action of inhibiting lipid accumulation in adipocytes (lipid accumulation inhibitory action), an action of promoting decomposition of lipids accumulated in adipocytes (lipid decomposition promoting action), or an action of inhibiting proliferation of adipocytes (adipocyte proliferation inhibitory action). That is, the anti-obesity agent in this specification may be a lipid accumulation inhibiting agent, a lipid decomposition promoting agent, an adipocyte proliferation inhibiting agent, or the like.

The anti-obesity agent according to one embodiment contains the above bagasse decomposition extract as an active ingredient.

The anti-obesity agent according to the present embodiment may be composed of only the bagasse decomposition extract as an active ingredient, and may further contain a material that can be used for foods, quasi-drugs or pharmaceuticals. The material that can be used for foods, quasi-drugs or pharmaceuticals is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents.

Examples of proteins include milk casein, whey, soy proteins, wheat proteins, and egg white. Examples of carbohydrates include corn starch, cellulose, pregelatinized starch, wheat starch, rice starch, and potato starch. Examples of oils and fats include salad oil, corn oil, soybean oil, safflower oil, olive oil, and palm oil. Examples of sweeteners include sugars such as glucose, sucrose, fructose, high-fructose corn syrup, and fructose-glucose corn syrup, sugar alcohols such as xylitol, erythritol, and maltitol, artificial sweeteners such as sucralose, aspartame, saccharin, and acesulfame K, and Stevia sweeteners. Examples of minerals include calcium, potassium, phosphorus, sodium, manganese, iron, zinc, magnesium, and salts thereof. Examples of vitamins include vitamin E, vitamin C, vitamin A, vitamin D, B vitamins, biotin, and niacin. Examples of excipients include dextrin, starch, lactose, and crystalline cellulose. Examples of binders include polyvinyl alcohols, gelatin, hydroxypropyl methyl cellulose, hydroxypropyl methyl cellulose, carboxymethyl cellulose sodium, and polyvinylpyrrolidone. Examples of lubricants include magnesium stearate, calcium stearate, and talc. Examples of disintegrants include crystalline cellulose, agar, gelatin, calcium carbonate, sodium hydrogen carbonate, and dextrin. Examples of emulsifiers or surfactants include sucrose fatty acid esters, citric acid, lactic acid, glycerin fatty acid esters, polyglycerin fatty acid esters, sorbitan fatty acid esters, propylene glycol fatty acid esters, and lecithin. Examples of bases include cetostearyl alcohol, lanolin, and polyethylene glycol. Examples of dissolution adjuvants include polyethylene glycol, propylene glycol, sodium carbonate, and sodium citrate. Examples of suspension agents include glycerin monostearate, polyvinyl alcohol, polyvinylpyrrolidone, methyl cellulose, hydroxymethyl cellulose, and sodium alginate. These may be used alone or two or more thereof may be used in combination.

When the anti-obesity agent contains other materials, the content of the bagasse decomposition extract as an active ingredient may be appropriately set depending on the form of the anti-obesity agent to be described below, the purpose of use, and the like. However, in order to more easily inhibit accumulation of lipids in adipocytes, the content is preferably 100 µg/g or more, more preferably 250 µg/g or more, and still more preferably 400 µg/g or more or preferably 10 mg/g or less, more preferably 7.5 mg/g or less, and still more preferably 5 mg/g or less with respect to a total amount of the anti-obesity agent.

The anti-obesity agent may be in any form such as a solid (a powder, a granule, etc.), a liquid (a solution, a suspension, etc.), and a paste, and may be in any dosage form such as a powder, a pill, a granule, a tablet, a capsule, a lozenge, a liquid, and a suspension.

One aspect of the mechanism of obesity is that adipocytes are subjected to lipid synthesis to accumulate lipids and cause hypertrophy. Particularly, the anti-obesity agent of the present embodiment has an action of inhibiting accumulation of lipids in adipocytes. Therefore, when the anti-obesity agent of the present embodiment is ingested, accumulation of lipids in adipocytes is inhibited, and as a result, obesity is inhibited. This anti-obesity agent is beneficial because it can effectively inhibit or solve obesity without relying on excessive exercise or dietary restrictions.

It can be confirmed whether the anti-obesity agent has a lipid accumulation inhibitory action, for example, by staining accumulated lipid droplets when adipose progenitor cells are induced to differentiate into adipocytes with a lipophilic pigment, performing observation under a microscope, and observing whether the number of lipid droplets in a specimen to which a lipid inhibiting agent is added is reduced compared with a specimen to which no lipid inhibiting agent is added. In addition, a determination of whether the anti-obesity agent has a lipid accumulation inhibitory action can be confirmed by extracting the lipophilic pigment staining lipid droplets, measuring the absorbance, and calculating the degree of lipid accumulation from the change in the absorbance resulting from addition of the lipid inhibiting agent.

The anti-obesity agent can be used as foods, quasi-drugs or pharmaceuticals. Foods may be provided in the form of, for example, health foods, specific health foods, functional foods, nutritionally functional foods, and supplements.

The anti-obesity agent may be administered parenterally such as intravenous administration or may be orally administered. The anti-obesity agent is preferably orally administered.

When the anti-obesity agent is administered parenterally, for example, the dose is preferably administered so that there is 50 µg/kg (body weight) or more of the bagasse decomposition extract at one time, more preferably administered so that there is 150 µg/kg (body weight) or more of the bagasse decomposition extract at one time, and still more preferably administered so that there is 250 µg/kg (body weight) or more of the bagasse decomposition extract at one time. In addition, the dose is preferably administered so that there is 100 µg/kg (body weight) or more of the bagasse decomposition extract per day, more preferably administered so that there is 300 µg/kg (body weight) or more of the bagasse decomposition extract per day, and still more preferably administered so that there is 500 µg/kg (body weight) or more of the bagasse decomposition extract per day. In addition, the dose is preferably administered so that there is 2,000 mg/kg (body weight) or less of the bagasse decomposition extract at one time, more preferably administered so that there is 1,500 mg/kg (body weight) or less of the bagasse decomposition extract at one time, and still more preferably administered so that there is 1,000 mg/kg (body weight) or less of the bagasse decomposition extract at one time. In addition, the dose is preferably administered so that there is 4,000 mg/kg (body weight) or less of the bagasse decomposition extract per day, more preferably administered so that there is 3,000 mg/kg (body weight) or less of the bagasse decomposition extract per day, and still more preferably administered so that there is 2,000 mg/kg (body weight) or less of the bagasse decomposition extract per day. Within this range, it is possible to achieve a sufficient concentration in the blood and it is possible to exhibit the obesity inhibiting action more efficiently.

When the anti-obesity agent is orally administered, the dose is preferably administered so that there is 60 µg/kg (body weight) or more of the bagasse decomposition extract at one time, more preferably administered so that there is 120 µg/kg (body weight) or more of the bagasse decomposition extract at one time, and still more preferably administered so that there is 180 µg/kg (body weight) or more of the bagasse decomposition extract at one time. In addition, the dose is preferably administered so that there is 180 µg/kg (body weight) or more of the bagasse decomposition extract per day, more preferably administered so that there is 360 µg/kg (body weight) or more of the bagasse decomposition extract per day, and still more preferably administered so that there is 540 µg/kg (body weight) or more of the bagasse decomposition extract per day. In addition, the dose is preferably administered so that there is 1,000 mg/kg (body weight) or less of the bagasse decomposition extract at one time, more preferably administered so that there is 800 mg/kg (body weight) or less of the bagasse decomposition extract at one time, and still more preferably administered so that there is 600 mg/kg (body weight) or less of the bagasse decomposition extract at one time. In addition, the dose is preferably administered so that there is 3,000 mg/kg (body weight) or less of the bagasse decomposition extract per day, more preferably administered so that there is 2,000 mg/kg (body weight) or less of the bagasse decomposition extract per day, and still more preferably administered so that there is 1,000 mg/kg (body weight) or less of the bagasse decomposition extract per day. Within this range, it is possible to achieve a sufficient concentration in the blood and it is possible to exhibit the obesity inhibiting action more efficiently.

Since the anti-obesity agent of the present embodiment has the above action, it can be used for patients diagnosed with obesity and for people with normal body weights who want to prevent obesity before it happens.

A specific mode of the lipid accumulation inhibiting agent according to one embodiment may be the same mode as that of the above anti-obesity agent. That is, for the lipid accumulation inhibiting agent according to one embodiment, in the above description of the anti-obesity agent, "anti-obesity agent" may be read as "lipid accumulation inhibiting agent."

One embodiment of the present invention can also provide a method of inhibiting obesity or lipid accumulation including a step of administering an effective amount of an anti-obesity agent or a lipid accumulation inhibiting agent containing the above bagasse decomposition extract as an active ingredient to subject in need thereof. In addition, one embodiment of the present invention can provide a bagasse decomposition extract used for a method of inhibiting obesity or lipid accumulation. The subjects in the above method may be mammals and are preferably humans. A mode, an administration method, a dose (intake), and the like of the anti-obesity agent or the lipid accumulation inhibiting agent may be the same as those described above.

Another embodiment of the present invention can provide use of a bagasse decomposition extract for producing an anti-obesity agent or a lipid accumulation inhibiting agent. In addition, one embodiment of the present invention can also provide use of a bagasse decomposition extract for inhibiting obesity or lipid accumulation. A mode of the anti-obesity agent or the lipid accumulation inhibiting agent may be the same as that described above.

Second Embodiment: Anti-Dementia Agent

An anti-dementia agent of the present invention has an anti-dementia action. "Anti-dementia action" in the present invention is a concept including an action of preventing onset of dementia before it happens, an action of delaying onset of dementia, and an action of recovering from dementia once it has developed from the state at the time of onset. Dementia to which the anti-dementia agent of the present invention will be applied may be Alzheimer's type dementia. Alzheimer's type dementia includes a pathological condition (cholinergic hypothesis) caused by loss of acetylcholinergic neurons in Meynert nuclei in the basal forebrain and a pathological condition (amyloid hypothesis) caused by accumulation of amyloid β proteins. The two cases indicate different pathological conditions, and are not the same pathological condition viewed from different angles. Dementia to which the anti-dementia agent of the present invention will be applied may be Alzheimer's type dementia based on any hypothesis, and is preferably Alzheimer's type dementia based on the amyloid hypothesis. That is, dementia to which the anti-dementia agent of the present invention will be applied may be Alzheimer's type dementia caused by accumulation of amyloid β proteins. In other words, the present invention can also provide an anti-dementia agent for Alzheimer's type dementia, an anti-dementia agent for Alzheimer's type dementia based on the amyloid hypothesis, or an anti-dementia agent for Alzheimer's type dementia caused by accumulation of amyloid β proteins.

In Alzheimer's type dementia based on the amyloid hypothesis, it is thought that cognitive function is impaired because tau proteins are accumulated in the brain in addition to amyloid β proteins and thus death of brain nerve cells is caused. Accumulation of amyloid β proteins starts in an early stage, and accumulation of tau proteins starts after about 10 years. Then, accumulation of amyloid β proteins and tau proteins continues and thus brain nerve cells are killed and dementia develops after about 25 years from the early stage. In another aspect, the anti-dementia agent of the present invention can have an action of inhibiting accumulation of amyloid β proteins in the brain and an action of reducing an amount of amyloid β proteins accumulated in the brain, and also an action of inhibiting accumulation of tau proteins in the brain and an action of reducing an amount of tau proteins accumulated in the brain.

The present invention can also provide a memory disorder improving/inhibiting agent. The memory disorder improving/inhibiting agent of the present invention has an action of improving or inhibiting memory disorders. "Memory disorder improving/inhibiting" in the present invention is a concept including an action of preventing onset of memory disorders before it happens, an action of delaying onset of memory disorders, and an action of recovering from memory disorders once they have developed from the state at the time of onset. Memory disorders to which the memory disorder improving/inhibiting agent of the present invention will be applied may be long-term memory disorders or short-term memory disorders, and are preferably short-term memory disorders. That is, the present invention can provide a short-term memory disorder improving/inhibiting agent and also provide an agent for improving/inhibiting short-term memory disorders caused by accumulation of amyloid β proteins.

The anti-dementia agent according to one embodiment contains the above bagasse decomposition extract as an active ingredient.

The anti-dementia agent may be composed of only the bagasse decomposition extract as an active ingredient, and may further contain a material that can be used for foods, quasi-drugs or pharmaceuticals. The material that can be used for foods, quasi-drugs or pharmaceuticals is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents. Regarding proteins, carbohydrates, oils and fats, sweeteners, minerals, vitamins, fragrances, excipients, binders, lubricants, disintegrants, emulsifiers, surfactants, bases, dissolution adjuvants, and suspension agents, the same components as used for the above anti-obesity agent may be used.

When the anti-dementia agent contains other materials, the content of the bagasse decomposition extract as an active ingredient may be appropriately set depending on the form of the anti-dementia agent to be described below, the purpose of use, and the like. However, in order to exhibit the anti-dementia effect more effectively, the following range with respect to a total amount of the anti-dementia agent is preferable. The content of the bagasse decomposition extract as a solid content excluding monosaccharides and oligosaccharides is preferably 1 mass % or more, more preferably 3 mass % or more, and still more preferably 5 mass % or more or preferably 50 mass % or less, more preferably 40 mass % or less, and still more preferably 30 mass % or less.

The anti-dementia agent can be used as foods, quasi-drugs or pharmaceuticals. Foods may be provided in the form of, for example, health foods, specific health foods, functional foods, nutritionally functional foods, and supplements.

The anti-dementia agent can be used as feeds and feed additives. Examples of feeds include companion animal feeds such as dog food and cat food, livestock feeds, poultry feeds, and feeds for farmed fish and shellfish. "Feed" includes anything that animals ingest orally for nutritional purposes. More specifically, if classified according to the nutrient content, it includes all of roughages, concentrated feeds, inorganic feeds, and special feeds, and if classified according to official standards, it includes all of formulated feeds, mixed feeds, and single feeds. In addition, if classified according to feeding methods, it includes all of feeds that are directly fed, feeds that are fed by mixing with other feeds, and feeds that are added to drinking water to supplement nutrients.

The anti-dementia agent may be in any form such as a solid (a powder, a granule, etc.), a liquid (a solution, a suspension, etc.), and a paste, and may be in any dosage form such as a powder, a pill, a granule, a tablet, a capsule, a lozenge, a liquid, and a suspension.

The anti-dementia agent may be administered parenterally such as intravenous administration or may be orally administered. The anti-dementia agent is preferably orally administered.

When the anti-dementia agent is administered parenterally, for example, the dose is preferably administered so that there is 100 µg/kg (body weight) or more of the bagasse decomposition extract at one time, more preferably administered so that there is 150 µg/kg (body weight) or more of the bagasse decomposition extract at one time, and still more preferably administered so that there is 200 µg/kg (body weight) or more of the bagasse decomposition extract at one time. In addition, the dose is preferably administered so that there is 200 µg/kg (body weight) or more of the bagasse decomposition extract per day, more preferably administered so that there is 300 µg/kg (body weight) or more of the bagasse decomposition extract per day, and still more preferably administered so that there is 400 µg/kg (body weight) or more of the bagasse decomposition extract per day. In addition, the dose is preferably administered so that there is 2,000 mg/kg (body weight) or less of the bagasse decomposition extract at one time, more preferably administered so that there is 1,500 mg/kg (body weight) or less of the bagasse decomposition extract at one time, and still more preferably administered so that there is 1,000 mg/kg (body weight) or less of the bagasse decomposition extract at one time. In addition, the dose is preferably administered so that there is 4,000 mg/kg (body weight) or less of the bagasse decomposition extract per day, more preferably administered so that there is 3,000 mg/kg (body weight) or less of the bagasse decomposition extract per day, and still more preferably administered so that there is 2,000 mg/kg (body weight) or less of the bagasse decomposition extract per day. Within this range, it is possible to achieve a sufficient concentration in the blood and it is possible to exhibit the anti-dementia action more efficiently.

When the anti-dementia agent is orally administered, if the product containing the anti-dementia agent is intensively ingesting, the intake (daily intake or dose) of the product is preferably 50 to 3,000 mg/kg (body weight) and more preferably 100 to 2,000 mg/kg (body weight) with respect to a total amount of the bagasse decomposition extract (solid content) excluding monosaccharides and oligosaccharides. For daily ingestion for long periods, the intake (daily intake) of the product is preferably 1 to 1,000 mg/kg (body weight)

with respect to a total amount of the bagasse decomposition extract (solid content) excluding monosaccharides and oligosaccharides.

The anti-dementia agent of the present embodiment can be used for humans or animals in which amyloid β proteins are accumulated. In addition, the anti-dementia agent of the present embodiment can be used for humans or animals with dementia (or Alzheimer's type dementia) and humans or animals with memory disorders (or short-term memory disorders). The dementia and memory disorders may be caused by accumulation of amyloid β proteins.

A specific mode of the short-term memory disorder improving/inhibiting agent according to one embodiment may be the same mode as that of the above anti-dementia agent. That is, for the short-term memory disorder improving/inhibiting agent according to one embodiment, in the above description of the anti-dementia agent, "anti-dementia agent" may be read as "short-term memory disorder improving/inhibiting agent."

One embodiment of the present invention can also provide a method of improving/inhibiting dementia or short-term memory disorders including a step of administering an effective amount of an anti-dementia agent or a short-term memory disorder improving/inhibiting agent containing the above bagasse decomposition extract as an active ingredient to subject in need thereof. In addition, one embodiment of the present invention can provide a bagasse decomposition extract used for a method of improving/inhibiting dementia or short-term memory disorders. The subjects in the above method may be mammals and are preferably humans. A mode, an administration method, a dose (intake), and the like of the anti-dementia agent or the short-term memory disorder improving/inhibiting agent may be the same as those described above.

Another embodiment of the present invention can also provide use of a bagasse decomposition extract for producing the anti-dementia agent or the short-term memory disorder improving/inhibiting agent. In addition, one embodiment of the present invention can also provide use of a bagasse decomposition extract for improving/inhibiting dementia or short-term memory disorders. A mode of the anti-dementia agent or the short-term memory disorder improving/inhibiting agent may be the same as that described above.

Third Embodiment: Deodorant

A "deodorant" in this specification contains a component (active ingredient) having a deodorizing effect. The deodorant may exhibit a deodorizing effect by eliminating or inhibiting an odor of an object to be deodorized and may exhibit a deodorizing effect by masking an odor of an object to be deodorized (masking agent).

The deodorant according to one embodiment contains the above bagasse decomposition extract as an active ingredient. The bagasse decomposition extract contained in the deodorant may be a decompoed liquid obtained by at least one decomposition treatment selected from the group consisting of an alkaline treatment, a hydrothermal treatment, an acid treatment and a sub-critical water treatment.

The deodorant of the present embodiment may further contain other components as long as the effects of the present invention are not impaired. Examples of other components include other deodorants, fragrances, alcohols, surfactants, antibacterial agents, stabilizers, viscosity adjusting agents, pH adjusting agents, preservatives, and coloring agents.

The deodorant of the present embodiment can be used as a material for food (food deodorant), etiquette deodorants, pet deodorants, environmental deodorants, detergents, fabric softeners, hair coloring agents, perm agents or cosmetics. That is, deodorants may be used for deodorizing unpleasant odors generated from food materials such as meat, seafood, garlic chives, and vegetables such as garlic; odors (body odor) generated from humans such as bad breath, armpit odor, foot odor, and hair odor; odors absorbed on the hair or body (grilled meat smell, cigarette odor, etc.); odors generated from animals such as animal bad breath, body odor, and excrement odor; bad odors of household waste or industrial waste (generation sources) generated in household waste or industrial waste storage, household waste or industrial waste recovery sites, household waste or industrial waste collection sites, waste collection sites, and the like; and unpleasant odors from sewage processing plants, manure processing plants, crematoriums, slaughterhouses, dead animal processing plants, hospitals, clinics, inspection centers, wet areas such as toilets, bathrooms, and kitchens, general indoor, indoor building materials and wallpaper (bad odors of treatment agents used for processing such as formalin), curtains, coatings, furniture (bad odors of paints, treatment agents for processing, and moldy odors in closets and the like), shoe shelves, air conditioners, inside automobiles or trucks, gases generated from automobiles or trucks, and trains, aircrafts, factories, restaurants, photo shops or photo labs, gas stations, propane gas refilling stations, laundries or laundry factories, inns or hotels, beauty shops or barber shops, car repair shops, livestock barns, construction work sites, and the like.

The deodorant of the present embodiment can be more appropriately used for deodorizing odors containing isovaleric acid, acetic acid, methyl mercaptan, trimethylamine, diacetyl, acetaldehyde, formaldehyde, hydrogen sulfide, ammonia, nonenal, thioglycolic acid, thioglycolic acid salts (ammonium thioglycolate, monoethanolamine thioglycolate, sodium thioglycolate, etc.), cysteine or derivatives thereof, thioglycerin, sulfites, lactone thiol, cysteamine, or the like as a main component and cigarette odors. Examples of odors containing a component selected from among isovaleric acid, acetic acid, methyl mercaptan, trimethylamine, diacetyl, acetaldehyde, formaldehyde, hydrogen sulfide, ammonia and nonenal as a main component include body odors (including body odors due to aging) from sweat, feet, bad breath, farts, and the like, animal manure odors, rancid or spoiled food odors, and odors released from chemical substances used in building materials for buildings, wallpaper, furniture, and the like. Examples of odors containing a component selected from among thioglycolic acid, thioglycolic acid salts, cysteine or derivatives thereof, thioglycerin, sulfites, lactone thiol, and cysteamine as a main component include odors of perm agents including reducing agents.

The deodorant of the present embodiment can be more appropriately used for deodorizing odors containing at least one component selected from the group consisting of isovaleric acid, acetic acid, methyl mercaptan, trimethylamine, diacetyl, nonenal, ammonium thioglycolate, and monoethanolamine thioglycolate as a main component, and cigarette odors.

The form of use of the deodorant of the present embodiment is not particularly limited. For example, the deodorant of the present embodiment can be used by spraying or applying it. Examples of deodorants used by spraying include an aerosol spray type deodorant, a mist spray type deodorant, and a liquid product for sprinklers. The mist spray type deodorant is used, for example, for pet odors in homes, toilets, kitchen garbage, and cooking utensils. The deodorant of the present embodiment is added to water, and a surfactant, ethanol, an antibacterial agent, and the like are added as necessary, and the mixture is filled into a mist spray bottle to obtain a mist spray type deodorant. The aerosol type deodorant is used, for example, for bad odors in garbage and toilets which are strong bad odors in the home. The aerosol type deodorant is obtained by, for example, diluting the deodorant of the present embodiment in water or an ethanol aqueous solution, and filling the diluted deodorant into an aerosol container together with an injection agent (injection gas), for example, LPG and carbon dioxide. The deodorant used by spraying is distributed indoors by being formed into a fine mist and thus is mainly used to deodorize rooms. In addition, the deodorant may be intermittently or continuously sprayed in places in which bad odors are easily generated such as dairy farms and fish markets, and can deodorize bad odors generated in these places.

Examples of deodorants used by applying include a liquid deodorant, a gel deodorant, and a paste deodorant. The liquid deodorant, the gel deodorant, and the paste deodorant may be in the form of emulsion such as cream or milk. The deodorant used by applying can be used for deodorizing body odors, for example, by applying it to the human body.

The deodorant of the present embodiment can be used as sheet-like deodorants impregnated into cloths, paper, or non-woven fabrics; deodorants absorbed on powders or granules; deodorants kneaded or adsorbed on a granular type, pellet type, block type, or tablet gel (for example, space deodorants to be described below); deodorants adsorbed on porous carriers such as a ceramic, activated carbon, and bentonite; deodorants which have a deodorizing effect when a liquid deodorant is put into a container, a part of a component which the liquid penetrates such as a piece of sponge, cloth, and ceramic is brought into contact with the deodorant in the container, and the penetrating deodorant is vaporized; deodorants which have a deodorizing effect when a deodorant is put into a porous container such as a ceramic one, and the deodorant that has penetrated to the outside of the container vaporizes and deodorants that are in a liquid state and added to bad odor sources directly; and deodorants impregnated into films or filters, or wallpaper, building materials, diapers, sanitary products, shoe insoles, deodorant fibers (cloths), or deodorant leathers containing a deodorant on the surface or therein.

The deodorant of the present embodiment can also be used as a space deodorant. Since a component (active ingredient) having a deodorizing effect gradually evaporates (volatilizes), the space deodorant has a deodorizing effect that is maintained for a long time. The space deodorant is obtained by, for example, adsorbing or kneading the deodorant of the present embodiment into a gel or an appropriate carrier. More specifically, the space deodorant can be obtained by adding the deodorant of the present embodiment to a combination of one or two or more of gelling agents (for example, carrageenan, agar, locust bean gum, polyvinyl alcohols, gum arabic, gellan gum, gelatin, carboxymethyl cellulose, chitin, chitosan, sodium alginate, and polyacrylamide) and solidifying it.

In addition, a pet excrement treatment agent having a strong deodorizing effect can be produced using the deodorant of the present embodiment. The pet excrement treatment agent can be produced by preparing bentonite, zeolite, wood powder, paper powder, or the like as a main material, adding sodium polyacrylate, other sodium compounds, magnesium compounds, or the like thereto as necessary, adding the deodorant of the present embodiment thereto, adding an appropriate amount of water, and performing mixing, molding and drying. The result is put into toilets for pets such as cats, cats defecate on the treatment agent, and an excrement treatment agent having an excellent deodorizing effect can be obtained.

In the above form of use, the amount of the deodorant used according to the present embodiment is not particularly limited. In the case of the mist spray type deodorant, the content of the deodorant of the present embodiment may be, for example, 0.01 to 50% (volume/volume) with respect to a total amount of the mist spray type deodorant. In the case of the aerosol type deodorant, the content of the deodorant of the present embodiment may be 0.2 to 70% (volume/volume) with respect to a total amount of the aerosol type deodorant. In the case of the space deodorant, the content of the deodorant of the present embodiment may be, for example, 0.5 to 20% (volume/volume) with respect to a total amount of the space deodorant.

An article having a deodorizing effect can be obtained by a method of mixing other materials with the deodorant of the present embodiment, and performing molding and drying. In addition, an article having a deodorizing effect can also be obtained by mixing two or more materials other than the deodorant of the present embodiment in advance, performing molding and drying, and absorbing the deodorant of the present embodiment on the obtained molded product.

One aspect of the present invention can provide a deodorant producing method. That is, the deodorant producing method includes a process of obtaining a bagasse decomposition extract. In one embodiment, the process of obtaining a bagasse decomposition extract may include at least one decomposition treatment process selected from the group consisting of an alkaline treatment, a hydrothermal treatment, an acid treatment and a sub-critical water treatment. The process of obtaining a bagasse decomposition extract may further include a process of allowing the decompoed liquid obtained in the decomposition treatment process to pass through a column filled with a fixed carrier to obtain a fraction. The detailed conditions for the decomposition treatment process and the process of obtaining a fraction are the same as described above.

One embodiment of the present invention can also provide a deodorizing method including a step of applying an effective amount of a deodorant containing the above bagasse decomposition extract as an active ingredient to an object to be deodorized. In addition, one embodiment of the present invention can provide a bagasse decomposition extract for deodorizing an object to be deodorized. A mode, a use method, a usage amount and the like of the deodorant may be the same as those described above.

Another embodiment of the present invention can also provide use of a bagasse decomposition extract for producing a deodorant. In addition, one embodiment of the present invention can also provide use of a bagasse decomposition extract for deodorizing an object to be deodorized. A mode of the deodorant may be the same as that described above.

Fourth Embodiment: Anti-Aging Agent

An anti-aging agent of the present invention has an anti-aging action. The anti-aging action may be an action of inhibiting skin aging, and more specifically, an action of inhibiting and/or improving functional deterioration of the skin due to aging, UV irradiation, or the like. The anti-aging action may be an action of inhibiting and/or improving skin wrinkles, sagging, hardening and the like.

Components such as type I collagen, elastin, hyaluronic acid, and the like contained in the dermis are also called extracellular matrix components. Extracellular matrix components are produced from fibroblasts. One cause of skin aging is decomposition or reduction of extracellular matrix components.

Decomposition of extracellular matrix components is caused by extracellular matrix decomposition enzymes. For example, type I collagen is decomposed by matrix metalloproteinase (MMP-1) which is one of extracellular matrix decomposition enzymes. With MMP-1, the amount of proteins is increased due to UV irradiation and the activity is enhanced. As a result of MMP-1 production and enhanced activity, collagen is reduced and denatured, the skin loses elasticity, which can cause the occurrence of skin wrinkles or sagging. On the other hand, elastin is decomposed with an elastase which is one of extracellular matrix decomposition enzymes. Although elastin acts like a spring that connects collagen fibers, elastin is decomposed due to the elastase, and thus the skin loses elasticity, which can cause the occurrence of skin wrinkles or sagging.

The anti-aging agent of the present invention has an action of inhibiting extracellular matrix decomposition enzymes (an action of inhibiting production of extracellular matrix decomposition enzymes, and an action of decreasing activity of extracellular matrix decomposition enzyme), and for example, has an action of inhibiting MMP-1 that decomposes type I collagen and/or an action of inhibiting an elastase that decomposes elastin. Accordingly, skin aging is inhibited. That is, the anti-aging agent of the present invention may be based on the action of inhibiting extracellular matrix decomposition enzymes, and more specifically, based on the MMP-1 inhibiting action or the elastase inhibiting action. In addition, the present invention can also provide an extracellular matrix decomposition enzyme inhibitor, and more specifically, an MMP-1 inhibitor or an elastase inhibitor.

More specifically, the action of inhibiting MMP-1 may be an action of inhibiting production of MMP-1 or an action of inhibiting activity of MMP-1. More specifically, the action of inhibiting an elastase may be an action of inhibiting production of an elastase or an action of inhibiting activity of an elastase. That is, the anti-aging agent of the present invention may be based on at least one action among the action of inhibiting production of MMP-1, the action of inhibiting activity of MMP-1, the action of inhibiting production of an elastase and the action of inhibiting activity of an elastase. The anti-aging agent of the present invention may be based on the action of inhibiting production of MMP-1 and/or the action of inhibiting activity of an elastase. In addition, the present invention can provide an MMP-1 production inhibitor, an MMP-1 activity inhibitor, an elastase production inhibitor, or an elastase activity inhibitor. The present invention can also provide an MMP-1 production inhibitor or an elastase activity inhibitor.

On the other hand, the amount of extracellular matrix components produced decreases due to decline of the number of fibroblasts with age, UV irradiation, and the like. When fibroblasts are activated, it is possible to minimize a decrease in the amount of extracellular matrix components produced. Since the anti-aging agent of the present invention also has an action of activating fibroblasts, skin aging is further inhibited. That is, the anti-aging agent of the present invention may be based on the fibroblast activation action. In addition, the present invention can also provide a fibroblast activator.

The anti-aging agent according to one embodiment contains the above bagasse decomposition extract as an active ingredient.

The anti-aging agent can be used as cosmetics, food compositions, pharmaceuticals or quasi-drugs. The food composition may be provided in the form of, for example, health foods, specific health foods, functional foods, nutritionally functional foods, and supplements.

The anti-aging agent may be composed of only the bagasse decomposition extract as an active ingredient, and may further contain a material that can be used for cosmetics, food compositions, quasi-drugs or pharmaceuticals. The material that can be used for cosmetics, food compositions, quasi-drugs or pharmaceuticals is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents Regarding proteins, carbohydrates, oils and fats, sweeteners, minerals, vitamins, fragrances, excipients, binders, lubricants, disintegrants, emulsifiers, surfactants, bases, dissolution adjuvants, and suspension agents, the same components as used for the above anti-obesity agent may be used.

When the anti-aging agent contains other materials, the content of the bagasse decomposition extract as an active ingredient may be appropriately set depending on the form of the anti-aging agent to be described below, the purpose of use, and the like. However, in order to exhibit the anti-aging effect more effectively, the following range with respect to a total amount of the anti-aging agent is preferable. The content of the bagasse decomposition extract as a solid content is preferably 0.5 mass % or more, more preferably 1 mass % or more, and still more preferably 3 mass % or more or preferably 50 mass % or less, more preferably 40 mass % or less, and still more preferably 30 mass % or less.

The form of the anti-aging agent is not limited, and may be any form such as a solid (a powder, a granule, etc.), a liquid (a solution, a suspension, etc.), and a paste, and may be in any dosage form such as a powder, a pill, a granule, a tablet, a capsule, a lozenge, a liquid, and a suspension.

When the anti-aging agent is used as cosmetics, the cosmetics may include basic cosmetics such as cosmetic liquids, emulsions, lotions, creams, beauty liquids, oils, packs, and lip creams, hair styling products such as hair tonics and hair liquids, hair cosmetics such as hair restorer and hair nourishers, and makeup cosmetics such as foundations, lipsticks, blushes, eye shadows, eyeliners, mascara, and eyebrow liners.

The anti-aging agent may be orally administered or may be administered parenterally.

When the anti-aging agent is orally administered, for example, the dose is preferably administered so that there is 50 μg/kg (body weight) or more of the bagasse decomposition extract at one time, more preferably administered so that there is 100 μg/kg (body weight) or more of the bagasse decomposition extract at one time, and still more preferably administered so that there is 150 μg/kg (body weight) or more of the bagasse decomposition extract at one time. In addition, the dose is preferably administered so that there is 150 μg/kg (body weight) or more of the bagasse decomposition extract per day, more preferably administered so that there is 300 μg/kg (body weight) or more of the bagasse decomposition extract per day, and still more preferably administered so that there is 450 μg/kg (body weight) or more of the bagasse decomposition extract per day. In addition, the dose is preferably administered so that there is 1,000 mg/kg (body weight) or less of the bagasse decomposition extract at one time, more preferably administered so that there is 800 mg/kg (body weight) or less of the bagasse decomposition extract at one time, and still more preferably administered so that there is 600 mg/kg (body weight) or less of the bagasse decomposition extract at one time. In addition, the dose is preferably administered so that there is 3,000 mg/kg (body weight) or less of the bagasse decomposition extract per day, more preferably administered so that there is 2,000 mg/kg (body weight) or less of the bagasse decomposition extract per day, and still more preferably administered so that there is 1,000 mg/kg (body weight) or less of the bagasse decomposition extract per day. Within this range, the anti-aging agent can act on the dermis at a sufficient concentration and it is possible to exhibit the anti-aging action more efficiently.

When the anti-aging agent is applied to the skin through parenteral administration, for example, the amount applied to the skin is preferably applied so that there is 5 $\mu g/cm^2$ or more of the bagasse decomposition extract at one time, more preferably applied so that there is 10 $\mu g/cm^2$ or more of the bagasse decomposition extract at one time, and still more preferably applied so that there is 30 $\mu g/cm^2$ or more of the bagasse decomposition extract at one time. In addition, the amount applied to the skin is preferably applied so that there is 10 $\mu g/cm^2$ or more of the bagasse decomposition extract per day, more preferably applied so that there is 20 $\mu g/cm^2$ or more of the bagasse decomposition extract per day, and still more preferably applied so that there is 60 $\mu g/cm^2$ or more of the bagasse decomposition extract per day. In addition, the amount applied to the skin is preferably applied so that there is 500 $\mu g/cm^2$ or less of the bagasse decomposition extract at one time, more preferably applied so that there is 400 $\mu g/cm^2$ or less of the bagasse decomposition extract at one time, and still more preferably applied so that there is 300 $\mu g/cm^2$ or less of the bagasse decomposition extract at one time. In addition, the amount applied to the skin is preferably applied so that there is 1,000 $\mu g/cm^2$ or less of the bagasse decomposition extract per day, more preferably applied so that there is 800 $\mu g/cm^2$ or less of the bagasse decomposition extract per day, and still more preferably applied so that there is 600 $\mu g/cm^2$ or less of the bagasse decomposition extract per day. Within this range, the anti-aging agent can act on the dermis at a sufficient concentration and it is possible to exhibit the anti-aging action more efficiently The anti-aging agent can be used as feeds and feed additives. Examples of feeds include companion animal feeds such as dog food and cat food, livestock feeds, poultry feeds, and feeds for farmed fish and shellfish. "Feed" includes anything that animals ingest orally for nutritional purposes. More specifically, if classified according to the nutrient content, it includes all of roughages, concentrated feeds, inorganic feeds, and special feeds, and if classified according to official standards, it includes all of formulated feeds, mixed feeds, and single feeds. In addition, if classified according to feeding methods, it includes all of feeds that are directly fed, feeds that are fed by mixing with other feeds, and feeds that are added to drinking water to supplement nutrients.

A specific mode of the extracellular matrix decomposition enzyme inhibitor or fibroblast activator according to one embodiment may be the same mode as that of the above anti-aging agent. That is, for the extracellular matrix decomposition enzyme inhibitor or fibroblast activator according to one embodiment, in the above description of the anti-aging agent, "anti-aging agent" may be read as "extracellular matrix decomposition enzyme inhibitor" or "fibroblast activator."

One embodiment of the present invention can also provide an anti-aging method, an extracellular matrix decomposition enzyme inhibiting method or a fibroblast activation method including a step of administering an effective amount of an anti-aging agent, an extracellular matrix decomposition enzyme inhibitor, or a fibroblast activator containing the above bagasse decomposition extract as an active ingredient to subject in need thereof. In addition, one embodiment of the present invention can provide a bagasse decomposition extract used for the anti-aging method, the extracellular matrix decomposition enzyme inhibiting method or the fibroblast activation method. The subjects in the above method may be mammals and are preferably humans. A mode, an administration method, a dose (intake), and the like of the anti-aging agent, the extracellular matrix decomposition enzyme inhibitor, or the fibroblast activator may be the same as those described above.

Another embodiment of the present invention can also provide use of a bagasse decomposition extract for producing an anti-aging agent, an extracellular matrix decomposition enzyme inhibitor, or a fibroblast activator. In addition, one embodiment of the present invention can also provide use of a bagasse decomposition extract for anti-aging, for inhibiting an extracellular matrix decomposition enzyme or activating fibroblasts. A mode, an administration method, a dose (intake), and the like of the anti-aging agent, the extracellular matrix decomposition enzyme inhibitor, or the fibroblast activator may be the same as those described above.

Fifth Embodiment: Anti-Glycation Agent

An anti-glycation agent in this specification has an anti-glycation activity, and specifically, may have a production inhibitory action (glycation reaction inhibiting action), an accumulation inhibitory action or a decomposition action for advanced glycation endproducts (AGEs). In other words, the anti-glycation agent of the present embodiment may be, for example, a production inhibiting agent (glycation reaction inhibitor), an accumulation inhibiting agent or a decomposing agent (decomposition promoting agent) for advanced glycation endproducts.

The advanced glycation endproduct is a general term for products produced according to a glycation reaction (Maillard reaction). Examples of advanced glycation endproducts include CML ($N^\varepsilon$-(carboxymethyl)lysine), pentosidine, pyrraline and crossline. In addition, the anti-glycation agent of the present embodiment has a production inhibitory action, an accumulation inhibitory action or a decomposition promoting action for reaction intermediates in the glycation reaction, and as a result, may have the above anti-glycation activity. Specific examples of reaction intermediates in the glycation reaction include glyoxal (GO), 3-deoxyglucosone (3DG), and methylglyoxal (MGO).

The anti-glycation agent of the present embodiment contains the above bagasse decomposition extract as an active ingredient.

The content of the bagasse decomposition extract in the anti-glycation agent may be 0.01 to 100 mass % or 0.1 to 100 mass % with respect to a total amount of the anti-glycation agent.

The anti-glycation agent of the present embodiment may contain an excipient other than the bagasse decomposition extract.

When the anti-glycation agent is used for animals, examples of excipients include various starches such as corn starch and wheat starch, various rice brans such as dextrin, various glutens, wheat flour, bran, and defatted rice bran, soybeans such as soybean meal and soybean flour, sugars such as glucose and lactose, oils and fats such as vegetable oils and animal oils, fish meals, yeasts, silicon compounds, minerals such as various phosphates, diatomaceous earth and bentonite, and excipients that can be used to produce feed and feed additive formulations. In addition, when the anti-glycation agent is used for humans, examples of excipients include sugars such as lactose, starch, and maltose and excipients that can be used to produce other formulations for humans. Among these, corn starch, dextrin and defatted rice bran can be used as carriers for formulation, and when this is mixed with a bagasse decomposition extract, the anti-glycation agent can be formed into, for example, a powder, granule, or tablet solid formulation.

The anti-glycation agent of the present embodiment may be administered (administered orally or administered parenterally) to humans or animals, and thus exhibit an anti-glycation effect.

When the anti-glycation agent is administered parenterally, for example, the dose is preferably administered so that there is 100 μg or more of the bagasse decomposition extract at one time per 1 kg of body weight, more preferably administered so that there is 150 μg or more of the bagasse decomposition extract at one time per 1 kg of body weight, and still more preferably administered so that there is 200 μg or more of the bagasse decomposition extract at one time per 1 kg of body weight. In addition, the dose is preferably administered so that there is 200 μg or more of the bagasse decomposition extract per day per 1 kg of body weight, more preferably administered so that there is 300 μg or more of the bagasse decomposition extract per day per 1 kg of body weight, and still more preferably administered so that there is 400 μg or more of the bagasse decomposition extract per day per 1 kg of body weight. In addition, the dose is preferably administered so that there is 2,000 mg or less of the bagasse decomposition extract at one time per 1 kg of body weight, more preferably administered so that there is 1,500 mg or less of the bagasse decomposition extract at one time per 1 kg of body weight, and still more preferably administered so that there is 1,000 mg or less of the bagasse decomposition extract at one time per 1 kg of body weight. In addition, the dose is preferably administered so that there is 4,000 mg or less of the bagasse decomposition extract per day per 1 kg of body weight, more preferably administered so that there is 3,000 mg or less of the bagasse decomposition extract per day per 1 kg of body weight, and still more preferably administered so that there is 2,000 mg or less of the bagasse decomposition extract per day per 1 kg of body weight. Within this range, it is possible to achieve a sufficient concentration in the blood and it is possible to exhibit the anti-glycation activity more efficiently.

When the anti-glycation agent is orally administered, the dose of the anti-glycation agent may be more appropriately determined depending on the degree of purification and form of the bagasse decomposition extract, the type of subject animals, health conditions, the degree of growth, and the like. In particular, the mode of administration, for example, either intensive administration or long-term administration, is an important factor for determining the dose. In the case of intensive administration, the dose of the anti-glycation agent may be 50 to 3,000 mg or 100 to 2,000 mg per day per 1 kg of body weight with respect to a total amount of the bagasse decomposition extract (solid content). In addition, in the case of intensive administration, the administration period may be 1 to 20 days. In the case of long-term administration on a daily basis, the dose of the anti-glycation agent may be 1 to 500 mg or 1 to 100 mg per day per 1 kg of body weight with respect to a total amount of the bagasse decomposition extract (solid content). In the case of long-term administration, the administration period may be, for example, several weeks to several months (for example, 20 to 180 days). Within this range, it is possible to achieve a sufficient concentration in the blood and it is possible to exhibit the anti-glycation activity more efficiently.

The anti-glycation agent of the present embodiment can be used as a component for products such as pharmaceuticals, quasi-drugs, foods and drinks (food compositions), feeds, feed additives, and the like. Examples of foods and drinks (beverages and foods) include health foods, functional foods, special purpose foods, nutritional supplement foods, supplements and specific health foods. In addition, the anti-glycation agent can be used as a component in foods such as seasonings (soy source, miso, etc.) and confectionery or beverages such as water, soft drinks, fruit juice drinks, and alcohol drinks.

Examples of feed include companion animal feeds such as dog food and cat food, livestock feeds, poultry feeds, and feeds for farmed fish and shellfish. "Feed" includes anything that animals ingest orally for nutritional purposes. Specifically, if classified according to the nutrient content, it includes all of roughages, concentrated feeds, inorganic feeds, and special feeds, and if classified according to official standards, it includes all of formulated feeds, mixed feeds, and single feeds. In addition, if classified according to feeding methods, it includes all of feeds that are directly fed, feeds that are fed by mixing with other feeds, and feeds that are added to drinking water to supplement nutrients.

The product (for example, food and drink) composed of the anti-glycation agent of the present embodiment or containing the anti-glycation agent may be used for anti-glycation. That is, foods and drinks containing the anti-glycation agent of the present embodiment can be appropriately used as anti-glycation foods and drinks or a food composition for anti-glycation. The form of the product containing the anti-glycation agent may be either a solid or liquid form.

The content of the anti-glycation agent contained in the product may be appropriately determined depending on the type and ingesting method of the product. In order to exhibit the anti-glycation effect more effectively, the product preferably contains an amount of 0.001 mass % or more of the bagasse decomposition extract as a solid content. When the product containing the anti-glycation agent is intensively ingested, the intake (daily intake) of the product is preferably 50 to 3,000 mg/kg (body weight) and more preferably 100 to 2,000 mg/kg (body weight) with respect to a total amount of the bagasse decomposition extract (solid content). For daily ingestion for long periods, the intake (daily intake) of the product is preferably 1 to 500 mg/kg (body weight) with respect to a total amount of the bagasse decomposition extract (solid content).

One embodiment of the present invention can also provide an anti-glycation method including a step of administering an effective amount of an anti-glycation agent containing the above bagasse decomposition extract as an active ingredient to subject in need thereof. In addition, one embodiment of the present invention can provide a bagasse decomposition extract used for the anti-glycation method. The subjects in the above method may be mammals and are preferably humans. A mode, an administration method, a dose (intake), and the like of the anti-glycation agent may be the same as those described above.

Another embodiment of the present invention can also provide use of a bagasse decomposition extract for producing an anti-glycation agent. In addition, one embodiment of the present invention can also provide use of a bagasse decomposition extract for anti-glycation. A mode, an administration method, a dose (intake), and the like of the anti-glycation agent may be the same as those described above.

Sixth Embodiment: Anti-Type I Allergy Agent

An anti-type I allergic agent in this specification is a composition having an action of inhibiting type I allergic symptoms. The action of inhibiting type I allergic symptoms may be, for example, an action of alleviating, treating or preventing symptoms caused by type I allergy such as hay fever, urticaria, allergic rhinitis, and bronchial asthma. In addition, the action of inhibiting type I allergic symptoms may be an action of inhibiting degranulation of mast cells or basophils in the type I allergic reaction mechanism. That is, the anti-type I allergy agent in this specification may be a mast cell or basophil degranulation inhibiting agent.

The anti-type I allergy agent according to one embodiment contains the bagasse decomposition extract as an active ingredient.

The anti-type I allergy agent according to the present embodiment may be composed of only the bagasse decomposition extract as an active ingredient, and may further contain a material that can be used for foods, quasi-drugs or pharmaceuticals. The material that can be used for foods, quasi-drugs or pharmaceuticals is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents. Regarding proteins, carbohydrates, oils and fats, sweeteners, minerals, vitamins, fragrances, excipients, binders, lubricants, disintegrants, emulsifiers, surfactants, bases, dissolution adjuvants, and suspension agents, the same components as used for the above anti-obesity agent may be used.

When the anti-type I allergy agent contains other materials, the content of the bagasse decomposition extract as an active ingredient may be appropriately set depending on the form of the anti-type I allergy agent to be described below, the purpose of use, and the like. However, in order to more easily inhibit degranulation of adipocytes or basophils, the content is preferably 100 μg/g or more, more preferably 25 μg/g or more, and still more preferably 400 μg/g or more, or preferably 10 mg/g or less, more preferably 7.5 mg/g or less, and still more preferably 5 mg/g or less with respect to a total amount of the anti-type I allergy agent.

The anti-type I allergy agent may be in any form such as a solid (a powder, a granule, etc.), a liquid (a solution, a suspension, etc.), and a paste, and may be in any dosage form such as a powder, a pill, a granule, a tablet, a capsule, a lozenge, a liquid, and a suspension.

Particularly, the anti-type I allergy agent of the present embodiment has an action of inhibiting release (degranulation) of granules containing a chemical mediator such as histamine and leukotriene from mast cells or basophils to the outside of cells in the type I allergic reaction (degranulation inhibitory action). Therefore, according to the anti-type I allergy agent of the present embodiment, it is possible to effectively inhibit, treat or prevent symptoms caused by the type I allergic reaction.

It can be confirmed whether the anti-type I allergy agent has a degranulation inhibitory action, for example, such that, using cells in which IgE bound to the surface of cells such as rat basophilic leukemia cells (RBL-2H3 cells) is cross-linked with an antigen and thus granulocytes containing histamine and the like are released to the outside of the cells, and when the cells are stimulated with an antigen, compared to a specimen to which no anti-type I allergy agent is added, an inhibition degree of degranulation of the specimen to which the anti-type I allergy agent is added is calculated.

The anti-type I allergy agent can be used as foods, quasi-drugs or pharmaceuticals. Foods may be provided in the form of, for example, health foods, specific health foods, functional foods, nutritionally functional foods, and supplements.

The anti-type I allergic agent may be administered parenterally such as intravenous administration or may be orally administered. The anti-type I allergic agent is preferably orally administered.

When the anti-type I allergy agent is administered parenterally, for example, the dose is preferably administered so that there is 50 μg/kg (body weight) or more of the bagasse decomposition extract at one time, more preferably administered so that there is 150 μg/kg (body weight) or more of the bagasse decomposition extract at one time, and still more preferably administered so that there is 250 μg/kg (body weight) or more of the bagasse decomposition extract at one time. In addition, the dose is preferably administered so that there is 100 μg/kg (body weight) or more of the bagasse decomposition extract per day, more preferably administered so that there is 300 μg/kg (body weight) or more of the bagasse decomposition extract per day, and still more preferably administered so that there is 500 μg/kg (body weight) or more of the bagasse decomposition extract per day. In addition, the dose is preferably administered so that there is 2,000 mg/kg (body weight) or less of the bagasse decomposition extract at one time, more preferably administered so that there is 1,500 mg/kg (body weight) or less of the bagasse decomposition extract at one time, and still more preferably administered so that there is 1,000 mg/kg (body weight) or less of the bagasse decomposition extract at one time. In addition, the dose is preferably administered so that there is 4,000 mg/kg (body weight) or less of the bagasse decomposition extract per day, more preferably administered so that there is 3,000 mg/kg (body weight) or less of the bagasse decomposition extract per day, and still more preferably administered so that there is 2,000 mg/kg (body weight) or less of the bagasse decomposition extract per day. Within this range, it is possible to achieve a sufficient concentration in the blood and it is possible to exhibit the anti-type I allergic action more efficiently.

When the anti-type I allergy agent is orally administered, the dose is preferably administered so that there is 50 μg/kg (body weight) or more of the bagasse decomposition extract at one time, more preferably administered so that there is 100 μg/kg (body weight) or more of the bagasse decomposition extract at one time, and still more preferably administered so that there is 150 μg/kg (body weight) or more of the bagasse decomposition extract at one time. In addition, the dose is preferably administered so that there is 150 μg/kg (body weight) or more of the bagasse decomposition extract per day, more preferably administered so that there is 300 μg/kg (body weight) or more of the bagasse decomposition extract per day, and still more preferably administered so that there is 450 μg/kg (body weight) or more of the bagasse decomposition extract per day. In addition, the dose is preferably administered so that there is 1,000 mg/kg (body weight) or less of the bagasse decomposition extract at one time, more preferably administered so that there is 800 mg/kg (body weight) or less of the bagasse decomposition extract at one time, and still more preferably administered so that there is 600 mg/kg (body weight) or less of the bagasse decomposition extract at one time. In addition, the dose is preferably administered so that there is 3,000 mg/kg (body weight) or less of the bagasse decomposition extract per day, more preferably administered so that there is 2,000 mg/kg (body weight) or less of the bagasse decomposition extract per day, and still more preferably administered so that there is 1,000 mg/kg (body weight) or less of the bagasse decomposition extract per day. Within this range, it is possible to achieve a sufficient concentration in the blood and it is possible to exhibit the anti-type I allergic action more efficiently.

Since the anti-type I allergy agent of the present embodiment has the above action, it can be used for patients with symptoms of type I allergy or for people who have not developed allergies but want to prevent the type I allergy before it happens.

A specific mode of the mast cell or basophil degranulation inhibiting agent according to one embodiment may be the same mode as that of the above anti-type I allergy agent. That is, for the mast cell or basophil degranulation inhibiting agent according to one embodiment, in the above description of the anti-type I allergy agent, "anti-type I allergy agent" may be read as "mast cell or basophil degranulation inhibiting agent."

One embodiment of the present invention can also provide an anti-type I allergy method or a method of inhibiting degranulation of mast cells or basophils including a step of administering an effective amount of an anti-type I allergy agent or a mast cell or basophil degranulation inhibiting agent containing the above bagasse decomposition extract as an active ingredient to subject in need thereof. In addition, one embodiment of the present invention can provide a bagasse decomposition extract used for the anti-type I allergy method or the method of inhibiting degranulation of mast cells or basophils. The subjects in the above method may be mammals and are preferably humans. A mode, an administration method, a dose (intake), and the like of the anti-type I allergy agent or the mast cell or basophil degranulation inhibiting agent may be the same as those described above.

Another embodiment of the present invention can also provide use of a bagasse decomposition extract for producing an anti-type I allergy agent or a mast cell or basophil degranulation inhibiting agent. In addition, one embodiment of the present invention can also provide use of a bagasse decomposition extract for anti-type I allergy or for inhibiting degranulation of mast cells or basophils. A mode of the anti-type I allergy agent or the mast cell or basophil degranulation inhibiting agent may be the same as that described above.

Seventh Embodiment: Hypotensive Agent

A hypotensive agent of the present invention has an antihypertensive action. The antihypertensive action may be an action of minimizing an increase in blood pressure.

The body has various blood pressure adjusting mechanisms. Angiotensin II has an action of constricting blood vessels, an action of inhibiting excretion of sodium or water in the kidneys and increasing the blood volume, and has a function of increasing the blood pressure. Angiotensin II is produced by conversion of angiotensin I with angiotensin converting enzymes (ACE). Therefore, ACE is inhibited, production of angiotensin II is curbed and an increase in the blood pressure can be minimized.

Since the hypotensive agent of the present invention has an action of inhibiting ACE, production of angiotensin II is curbed, and as a result, an increase in the blood pressure is minimized. That is, the hypotensive agent of the present invention may be based on an angiotensin converting enzyme inhibiting action or based on an angiotensin II production inhibiting action. In addition, the present invention can also provide an angiotensin converting enzyme inhibitor.

The hypotensive agent according to one embodiment contains the above bagasse decomposition extract as an active ingredient.

The hypotensive agent can be used as food compositions, pharmaceuticals or quasi-drugs. The food composition may be provided in the form of, for example, health foods, specific health foods, functional foods, nutritionally functional foods, and supplements.

The hypotensive agent may be composed of only the bagasse decomposition extract as an active ingredient, and may further contain a material that can be used for food compositions, quasi-drugs or pharmaceuticals. The material that can be used for food compositions, quasi-drugs or pharmaceuticals is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents. Regarding proteins, carbohydrates, oils and fats, sweeteners, minerals, vitamins, fragrances, excipients, binders, lubricants, disintegrants, emulsifiers, surfactants, bases, dissolution adjuvants, and suspension agents, the same components as used for the above anti-obesity agent may be used.

When the hypotensive agent contains other materials, the content of the bagasse decomposition extract as an active ingredient may be appropriately set depending on the form of the hypotensive agent to be described below, the purpose of use, and the like. However, in order to exhibit the antihypertensive effect more effectively, the content as a solid content is preferable 1 mass % or more, more preferably 3 mass % or more, and still more preferably 5 mass % or more or preferably 50 mass % or less, more preferably 40 mass % or less, and still more preferably 30 mass % or less.

The form of the hypotensive agent is not limited, and may be any form such as a solid (a powder, a granule, etc.), a liquid (a solution, a suspension, etc.), and a paste, and may be in any dosage form such as a powder, a pill, a granule, a tablet, a capsule, a lozenge, a liquid, and a suspension.

The hypotensive agent may be orally administered or may be administered parenterally such as intravenous administration.

When the hypotensive agent is orally administered, for example, the dose is preferably administered so that there is 50 μg/kg (body weight) or more of the bagasse decomposition extract at one time, more preferably administered so that there is 100 μg/kg (body weight) or more of the bagasse decomposition extract at one time, and still more preferably administered so that there is 150 μg/kg (body weight) or more of the bagasse decomposition extract at one time. In addition, the dose is preferably administered so that there is 150 μg/kg (body weight) or more of the bagasse decomposition extract per day, more preferably administered so that there is 300 μg/kg (body weight) or more of the bagasse decomposition extract per day, and still more preferably administered so that there is 450 μg/kg (body weight) or more of the bagasse decomposition extract per day. In addition, the dose is preferably administered so that there is 1,000 mg/kg (body weight) or less of the bagasse decomposition extract at one time, more preferably administered so that there is 800 mg/kg (body weight) or less of the bagasse decomposition extract at one time, and still more preferably administered so that there is 600 mg/kg (body weight) or less of the bagasse decomposition extract at one time. In addition, the dose is preferably administered so that there is 3,000 mg/kg (body weight) or less of the bagasse decomposition extract per day, more preferably administered so that there is 2,000 mg/kg (body weight) or less of the bagasse decomposition extract per day, and still more preferably administered so that there is 1,000 mg/kg (body weight) or less of the bagasse decomposition extract per day. Within this range, it is possible to achieve a sufficient concentration in the blood and it is possible to exhibit the antihypertensive action more efficiently.

When the hypotensive agent is administered parenterally, for example, the dose is preferably administered so that there is 100 μg/kg (body weight) or more of the bagasse decomposition extract at one time, more preferably administered so that there is 150 μg/kg (body weight) or more of the bagasse decomposition extract at one time, and still more preferably administered so that there is 200 μg/kg (body weight) or more of the bagasse decomposition extract at one time. In addition, the dose is preferably administered so that there is 200 μg/kg (body weight) or more of the bagasse decomposition extract per day, more preferably administered so that there is 300 μg/kg (body weight) or more of the bagasse decomposition extract per day, and still more preferably administered so that there is 400 μg/kg (body weight) or more of the bagasse decomposition extract per day. In addition, the dose is preferably administered so that there is 2,000 mg/kg (body weight) or less of the bagasse decomposition extract at one time, more preferably administered so that there is 1,500 mg/kg (body weight) or less of the bagasse decomposition extract at one time, and still more preferably administered so that there is 1,000 mg/kg (body weight) or less of the bagasse decomposition extract at one time. In addition, the dose is preferably administered so that there is 4,000 mg/kg (body weight) or less of the bagasse decomposition extract per day, more preferably administered so that there is 3,000 mg/kg (body weight) or less of the bagasse decomposition extract per day, and still more preferably administered so that there is 2,000 mg/kg (body weight) or less of the bagasse decomposition extract per day. Within this range, it is possible to achieve a sufficient concentration in the blood and it is possible to exhibit the antihypertensive action more efficiently.

The hypotensive agent can be used as feeds and feed additives. Examples of feeds include companion animal feeds such as dog food and cat food, livestock feeds, poultry feeds, and feeds for farmed fish and shellfish. "Feed" includes anything that animals ingest orally for nutritional purposes. More specifically, if classified according to the nutrient content, it includes all of roughages, concentrated feeds, inorganic feeds, and special feeds, and if classified according to official standards, it includes all of formulated feeds, mixed feeds, and single feeds. In addition, if classified according to feeding methods, it includes all of feeds that are directly fed, feeds that are fed by mixing with other feeds, and feeds that are added to drinking water to supplement nutrients.

A specific mode of the angiotensin converting enzyme inhibitor according to one embodiment may be the same mode as that of the above hypotensive agent. That is, for the angiotensin converting enzyme inhibitor according to one embodiment, in the above description of the hypotensive agent, "hypotensive agent" may be read as "angiotensin converting enzyme inhibitor."

One embodiment of the present invention can also provide an anti-hypertension method or an angiotensin converting enzyme inhibiting method including a step of administering an effective amount of a hypotensive agent or an angiotensin converting enzyme inhibitor containing the above bagasse decomposition extract as an active ingredient to subject in need thereof. In addition, one embodiment of the present invention can provide a bagasse decomposition extract used for the anti-hypertension method or the angiotensin converting enzyme inhibiting method. The subjects in the above method may be mammals and are preferably humans. A mode, an administration method, a dose (intake), and the like of the hypotensive agent or the angiotensin converting enzyme inhibitor may be the same as those described above.

Another embodiment of the present invention can also provide use of a bagasse decomposition extract for producing a hypotensive agent or an angiotensin converting enzyme inhibitor. In addition, one embodiment of the present invention can also provide use of a bagasse decomposition extract for antihypertension or for inhibiting an angiotensin converting enzyme. A mode of the hypotensive agent or the angiotensin converting enzyme inhibitor may be the same as that described above.

Eighth Embodiment: Flavor Improving Agent

A flavor improving agent of the present invention has an action of improving flavors of foods and drinks. Flavor includes all sensations felt when taste and odor are present separately, or when taste and odor are present in combination, and sensations felt when taste and throat stimulation are present in combination.

Preferred flavors are flavors that people find preferable, and examples thereof include a delicious taste, a pure taste, a refreshing taste, ease of eating, ease of drinking, mellowness, smoothness, and an original material flavor.

Unpleasant flavors are flavors that people do not find preferable, and examples thereof include sourness, bitterness, odors, astringent tastes, miscellaneous tastes, unpleasant aftertastes, deterioration odors, retort sterilization odors, dry odors, oily odors, egg odors, animal odors of meat, fishy odors, green smells of beans and vegetables, oily sensations, irritating sensations, powdery feelings, stickiness of taste, and metallic tastes.

In one embodiment, the flavor improving agent of the present invention has an action of enhancing preferred flavors of foods and drinks. The action of enhancing preferred flavors of foods and drinks may be that the above preferred flavors are felt more strongly. That is, the flavor improving agent according to one embodiment may be based on an action of enhancing preferred flavors of foods and drinks. In addition, the present invention can also provide a preferred flavor enhancing agent for foods and drinks.

In another embodiment, the flavor improving agent of the present invention has an action of reducing unpleasant flavors of foods and drinks. The action of reducing unpleasant flavors of foods and drinks may be that the above unpleasant flavors of foods and drinks are less likely to be felt. That is, the flavor improving agent according to one embodiment may be based on the action of reducing unpleasant flavors of foods and drinks. In addition, the present invention can also provide an unpleasant flavor reducing agent for foods and drinks.

The flavor improving agent may have any or both of an action of enhancing preferred flavors of foods and drinks and an action of reducing unpleasant flavors.

The flavor improving agent according to one embodiment contains the above bagasse decomposition extract.

The flavor improving agent may be composed of only the bagasse decomposition extract and may further contain a material that can be used for food compositions (foods and drinks). The material that can be used for food compositions is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents. Regarding proteins, carbohydrates, oils and fats, sweeteners, minerals, vitamins, fragrances, excipients, binders, lubricants, disintegrants, emulsifiers, surfactants, bases, dissolution adjuvants, and suspension agents, the same components as used for the above anti-obesity agent may be used.

When the flavor improving agent contains other materials, the content of the bagasse decomposition extract may be appropriately set depending on the purpose of use of the flavor improving agent, and the like. However, in order to exhibit the flavor improving effect more effectively, the content as a solid content is preferably 0.1 mass % or more, more preferably 0.3 mass % or more, and still more preferably 0.5 mass % or more or preferably 90 mass % or less, more preferably 80 mass % or less, and still more preferably 70 mass % or less.

The above flavor improving agent is added to various foods and drinks and thus can improve flavors of foods and drinks. More specifically, when the flavor improving agent is added to foods and drinks, it is possible to enhance preferred flavors of foods and drinks and/or reduce unpleasant flavors of foods and drinks. Adding of the flavor improving agent to foods and drinks includes attaching or impregnating the flavor improving agent to and into foods and drinks. Therefore, foods and drinks contain the flavor improving agent. That is, foods and drinks according to one embodiment are foods and drinks which contain the flavor improving agent containing a bagasse decomposition extract and have improved flavors. The foods and drinks containing the flavor improving agent include foods and drinks to which the flavor improving agent is attached and foods and drinks with which the flavor improving agent is impregnated.

Foods and drinks include health foods, specific health foods, functional foods, nutritionally functional foods, and supplements in addition to general foods and drinks. Examples of foods and drinks include beverages such as milk beverages, lactic acid bacteria beverages, soy milk beverages, vegetable beverages, fruit beverages, teas, coffee beverages, alcohol drinks, and other soft drinks (beverages containing vinegar, etc.); and foods such as noodles, breads, vegetable processed products, fruit processed products, meat products, processed seafood, dairy products, bean formulations, soups, and seasoning. Foods and drinks whose flavors can be improved by the flavor improving agent are preferably soy milk beverages, beverages containing vinegar, lactic acid bacteria beverages, meat products, or processed seafood.

For example, when foods and drinks are soy milk beverages, the flavor improving agent can enhance preferred flavors of the soy milk beverages. Preferred flavors of soy milk beverages may be a pure taste, delicious tastes, a refreshing taste, ease of drinking, or the like. The flavor improving agent can reduce unpleasant flavors of soy milk beverages. The unpleasant flavors of soy milk beverages may be green smells of beans, unpleasant aftertastes, astringent tastes, miscellaneous tastes or the like.

When foods and drinks are beverages containing vinegar (vinegar-containing beverages), the flavor improving agent can enhance preferred flavors of the vinegar-containing beverages. Preferred flavors of vinegar-containing beverages may be ease of drinking, delicious tastes, a refreshing taste, mellowness, mouthfeel, and the like. The flavor improving agent can reduce unpleasant flavors of vinegar-containing beverages. Unpleasant flavors of vinegar-containing beverages may be sourness, unpleasant aftertastes, and the like.

When foods and drinks are lactic acid bacteria beverages, the flavor improving agent can enhance preferred flavors of the lactic acid bacteria beverage. Preferred flavors of lactic acid bacteria beverages may be a refreshing taste, a pure taste, ease of drinking, delicious tastes, elimination of aftertastes, and the like. The flavor improving agent can reduce unpleasant flavors of the lactic acid bacteria beverage. The unpleasant flavors of lactic acid bacteria beverages may be offensive tastes and the like.

When foods and drinks are meat products, the flavor improving agent can enhance preferred flavors of the meat products. Preferred flavors of meat products may be original flavors of meat, delicious tastes, ease of eating, a refreshing taste and the like. The flavor improving agent can reduce unpleasant flavors of meat products. The unpleasant flavors of meat products may be unpleasant aftertastes, meat smells, oily tastes, and the like.

When foods and drinks are processed seafood, the flavor improving agent can enhance preferred flavors of the processed seafood. The preferred flavors of processed seafood may be original flavors of seafood, delicious tastes, ease of eating, a refreshing taste and the like. The flavor improving agent can reduce unpleasant flavors of processed seafood. The unpleasant flavors of processed seafood may be unpleasant aftertastes, seafood odors, oily tastes, and the like.

The amount of the flavor improving agent added to foods and drinks can be appropriately selected depending on the type of foods and drinks added. The addition amount of the bagasse decomposition extract contained in the flavor improving agent may be 0.3 ppm by mass or more, 0.6 ppm by mass or more, 0.8 ppm by mass or more, 3 ppm by mass or more, or 5 ppm by mass or more, or may be 10 ppm by mass or more, 50 ppm by mass or less, 40 ppm by mass or less, or 30 ppm by mass or less with respect to a total amount of the foods and drinks. If the addition amount is within this range, a sufficient flavor improving effect can be obtained.

A specific mode of the preferred flavor enhancing agent for foods and drinks and the unpleasant flavor reducing agent for foods and drinks according to one embodiment may be the same mode as that of the above flavor improving agent. That is, for the preferred flavor enhancing agent for foods and drinks and the unpleasant flavor reducing agent for foods and drinks according to one embodiment, in the above description of the flavor improving agent, "flavor improving agent" may be read as "preferred flavor enhancing agent for foods and drinks" or "unpleasant flavor reducing agent for foods and drinks."

One embodiment of the present invention can also provide a flavor improving method, a food and drink preferred flavor enhancing method, or a food and drink unpleasant flavor reducing method including a step of adding an effective amount of a flavor improving agent, a preferred flavor enhancing agent for foods and drinks or an unpleasant flavor reducing agent for foods and drinks containing the above bagasse decomposition extract as an active ingredient to subject in need thereof. In addition, one embodiment of the present invention can provide a bagasse decomposition extract used for the flavor improving method, the food and drink preferred flavor enhancing method, or the food and drink unpleasant flavor reducing method. The objects in the method may be foods and drinks. A mode, an administration method, a dose (intake), and the like of the flavor improving agent, the preferred flavor enhancing agent for foods and drinks, or the unpleasant flavor reducing agent for foods and drinks may be the same as those described above.

Another embodiment of the present invention can also provide use of a bagasse decomposition extract for producing a flavor improving agent, a preferred flavor enhancing agent for foods and drinks, or an unpleasant flavor reducing agent for foods and drinks. In addition, one embodiment of the present invention can also provide use of a bagasse decomposition extract for improving flavors of foods and drinks, for enhancing preferred flavors of foods and drinks, or for reducing unpleasant flavors of foods and drinks. A mode of the flavor improving agent, the preferred flavor enhancing agent for foods and drinks, or the unpleasant flavor reducing agent for foods and drinks may be the same as that described above.

Ninth Embodiment: Muscle Enhancing Agent

The muscle enhancing agent of the present invention has a muscle enhancing action. The muscle enhancing action in this specification includes a myotube cell differentiation promoting action that promotes differentiation from myoblasts to myotube cells and a mitochondria activation action that activates mitochondria in muscle. That is, the present invention can provide a myotube cell differentiation promoting agent or a mitochondrial activator.

The mitochondria activation action includes an action of increasing the amount of mitochondria (the amount of mitochondria per cell) present in cells (myocytes) in muscle and also an action of increasing activity of mitochondria (mitochondrial activity per cell) present in myocytes. That is, the present invention can also provide a mitochondria bulking agent in myocytes or a mitochondrial activator in myocytes.

The muscle enhancing agent according to one embodiment contains the above bagasse decomposition extract as an active ingredient.

The muscle enhancing agent can be used as food compositions, pharmaceuticals or quasi-drugs. The food composition may be provided in the form of, for example, health foods, specific health foods, functional foods, nutritionally functional foods, and supplements. That is, according to the present invention, it is possible to provide a food composition for muscle enhancement, a pharmaceutical for muscle enhancement, or a quasi-drug for muscle enhancement.

The muscle enhancing agent may be composed of only the bagasse decomposition extract as an active ingredient, and may further contain a material that can be used for food compositions, quasi-drugs or pharmaceuticals. The material that can be used for food compositions, quasi-drugs or pharmaceuticals is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents.

Regarding proteins, carbohydrates, oils and fats, sweeteners, minerals, vitamins, fragrances, excipients, binders, lubricants, disintegrants, emulsifiers, surfactants, bases, dissolution adjuvants, and suspension agents, the same components as used for the above anti-obesity agent may be used.

When the muscle enhancing agent contains other materials, the content of the bagasse decomposition extract as an active ingredient may be appropriately set depending on the form of the muscle enhancing agent to be described below, the purpose of use, and the like. However, in order to exhibit the muscle enhancing effect more effectively, the content as a solid content is preferably 0.5 mass % or more, more preferably 1 mass % or more, and still more preferably 3 mass % or more or preferably 50 mass % or less, more preferably 40 mass % or less, and still more preferably 30 mass % or less.

The form of the muscle enhancing agent is not limited, and may be any form such as a solid (a powder, a granule, etc.), a liquid (a solution, a suspension, etc.), and a paste, and may be in any dosage form such as a powder, a pill, a granule, a tablet, a capsule, a lozenge, a liquid, and a suspension.

The muscle enhancing agent may be orally administered or may be administered parenterally such as intravenous administration.

When the muscle enhancing agent is orally administered, for example, the dose is preferably administered so that there is 50 µg/kg (body weight) or more of the bagasse decomposition extract at one time, more preferably administered so that there is 100 µg/kg (body weight) or more of the bagasse decomposition extract at one time, and still more preferably administered so that there is 150 µg/kg (body weight) or more of the bagasse decomposition extract at one time. In addition, the dose is preferably administered so that there is 150 µg/kg (body weight) or more of the bagasse decomposition extract per day, more preferably administered so that there is 300 µg/kg (body weight) or more of the bagasse decomposition extract per day, and still more preferably administered so that there is 450 µg/kg (body weight) or more of the bagasse decomposition extract per day. In addition, the dose is preferably administered so that there is 1,000 mg/kg (body weight) or less of the bagasse decomposition extract at one time, more preferably administered so that there is 800 mg/kg (body weight) or less of the bagasse decomposition extract at one time, and still more preferably administered so that there is 600 mg/kg (body weight) or less of the bagasse decomposition extract at one time. In addition, the dose is preferably administered so that there is 3,000 mg/kg (body weight) or less of the bagasse decomposition extract per day, more preferably administered so that there is 2,000 mg/kg (body weight) or less of the bagasse decomposition extract per day, and still more preferably administered so that there is 1,000 mg/kg (body weight) or less of the bagasse decomposition extract per day. Within this range, it is possible to achieve a sufficient concentration in the blood and it is possible to exhibit the muscle enhancing action more effectively.

When the muscle enhancing agent is administered parenterally, for example, the dose is preferably administered so that there is 50 µg/kg (body weight) or more of the bagasse decomposition extract at one time, more preferably administered so that there is 150 µg/kg (body weight) or more of the bagasse decomposition extract at one time, and still more preferably administered so that there is 250 µg/kg (body weight) or more of the bagasse decomposition extract at one time. In addition, the dose is preferably administered so that there is 100 µg/kg (body weight) or more of the bagasse decomposition extract per day, more preferably administered so that there is 300 μg/kg (body weight) or more of the bagasse decomposition extract per day, and still more preferably administered so that there is 500 μg/kg (body weight) or more of the bagasse decomposition extract per day. In addition, the dose is preferably administered so that there is 2,000 mg/kg (body weight) or less of the bagasse decomposition extract at one time, more preferably administered so that there is 1,500 mg/kg (body weight) or less of the bagasse decomposition extract at one time, and still more preferably administered so that there is 1,000 mg/kg (body weight) or less of the bagasse decomposition extract at one time. In addition, the dose is preferably administered so that there is 4,000 mg/kg (body weight) or less of the bagasse decomposition extract per day, more preferably administered so that there is 3,000 mg/kg (body weight) or less of the bagasse decomposition extract per day, and still more preferably administered so that there is 2,000 mg/kg (body weight) or less of the bagasse decomposition extract per day. Within this range, it is possible to achieve a sufficient concentration in the blood and it is possible to exhibit the muscle enhancing action more effectively.

The muscle enhancing agent of the present embodiment can be used for humans or animals. When the muscle enhancing agent is used for animals, it can be used as feeds or feed additives. Examples of feed include companion animal feeds such as dog food and cat food, livestock feeds, poultry feeds, and feeds for farmed fish and shellfish. "Feed" includes anything that animals ingest orally for nutritional purposes. More specifically, if classified according to the nutrient content, it includes all of roughages, concentrated feeds, inorganic feeds, and special feeds, and if classified according to official standards, it includes all of formulated feeds, mixed feeds, and single feeds. In addition, if classified according to feeding methods, it includes all of feeds that are directly fed, feeds that are fed by mixing with other feeds, and feeds that are added to drinking water to supplement nutrients.

The muscle enhancing agent according to the present embodiment may be used for promoting formation of muscle, for promoting recovery of damaged muscle, or for activating the function of the formed muscle.

A specific mode of the mitochondrial activator or the myotube cell differentiation promoting agent according to one embodiment may be the same mode as that of the above muscle enhancing agent. That is, for the mitochondrial activator or the myotube cell differentiation promoting agent according to one embodiment, in the above description of the muscle enhancing agent, "muscle enhancing agent" may be read as "mitochondrial activator" or "myotube cell differentiation promoting agent."

One embodiment of the present invention can also provide a muscle enhancing method, a mitochondria activation method, or a myotube cell differentiation promoting method including a step of administering an effective amount of a muscle enhancing agent, a mitochondrial activator, or a myotube cell differentiation promoting agent containing the above bagasse decomposition extract as an active ingredient to subject in need thereof. In addition, one embodiment of the present invention can provide a bagasse decomposition extract used for the muscle enhancing method, the mitochondria activation method, or the myotube cell differentiation promoting method. The subjects in the above method may be mammals and are preferably humans. A mode, an administration method, a dose (intake), and the like of the muscle enhancing agent, the mitochondrial activator, or the myotube cell differentiation promoting agent may be the same as those described above.

Another embodiment of the present invention can also provide use of a bagasse decomposition extract for producing a muscle enhancing agent, mitochondrial activator or a myotube cell differentiation promoting agent. In addition, one embodiment of the present invention can also provide use of a bagasse decomposition extract for enhancing muscles, for activating mitochondria or for promoting differentiation into myotube cells. A mode of the muscle enhancing agent, the mitochondrial activator, or the myotube cell differentiation promoting agent may be the same as that described above.

Tenth Embodiment: Bone Metabolism Improving Agent

A bone metabolism improving agent of the present invention has a bone metabolism improving action. The bone metabolism improving action may be at least one of an action of promoting bone formation (formation of new bone) and an action of inhibiting excess bone resorption (bone destruction). Therefore, it is possible to appropriately adjust the balance between bone formation and bone resorption, and as a result, it is possible to easily facilitate bone reconstruction. That is, the present invention can provide a bone formation promoting agent and a bone resorption inhibiting agent and can also provide an agent for adjusting balance between bone formation and bone resorption.

Promotion of bone formation in the bone formation promoting agent may be based on an action of promoting differentiation of osteoblasts. That is, the bone formation promoting agent in this specification can also be referred to as an osteoblast differentiation promoting agent. In addition, inhibition of bone resorption of the bone resorption inhibiting agent may be based on an action of inhibiting differentiation of osteoclasts. That is, the bone resorption inhibiting agent in this specification can also be referred to as an osteoclast differentiation inhibiting agent.

The bone formation promoting agent according to one embodiment contains the above bagasse decomposition extract as an active ingredient.

The bone metabolism improving agent can be used as food compositions, pharmaceuticals or quasi-drugs. The food composition may be provided in the form of, for example, health foods, specific health foods, functional foods, nutritionally functional foods, and supplements. That is, according to the present invention, it is also possible to provide a food composition for improving bone metabolism, a pharmaceutical for improving bone metabolism or a quasi-drug for improving bone metabolism.

The bone metabolism improving agent may be composed of only the bagasse decomposition extract as an active ingredient and may further contain a material that can be used for food compositions, quasi-drugs or pharmaceuticals. The material that can be used for food compositions, quasi-drugs or pharmaceuticals is not particularly limited, and examples thereof include amino acids, proteins, carbohydrates, oils and fats, sweeteners, minerals, vitamins, fragrances, excipients, binders, lubricants, disintegrants, emulsifiers, surfactants, bases, dissolution adjuvants, and suspension agents. Regarding proteins, carbohydrates, oils and fats, sweeteners, minerals, vitamins, fragrances, excipients, binders, lubricants, disintegrants, emulsifiers, surfactants, bases, dissolution adjuvants, and suspension agents, the same components as used for the above anti-obesity agent may be used.

The form of the bone metabolism improving agent is not limited, and may be any form such as a solid (a powder, a granule, etc.), a liquid (a solution, a suspension, etc.), and a paste, and may be in any dosage form such as a powder, a pill, a granule, a tablet, a capsule, a lozenge, a liquid, and a suspension.

The bone metabolism improving agent may be orally administered or may be administered parenterally such as intravenous administration.

When the bone metabolism improving agent is orally administered, for example, the dose is preferably administered so that there is 50 μg/kg (body weight) or more of the bagasse decomposition extract at one time, more preferably administered so that there is 100 μg/kg (body weight) or more of the bagasse decomposition extract at one time, and still more preferably administered so that there is 150 μg/kg (body weight) or more of the bagasse decomposition extract at one time. In addition, the dose is preferably administered so that there is 150 μg/kg (body weight) or more of the bagasse decomposition extract per day, more preferably administered so that there is 300 μg/kg (body weight) or more of the bagasse decomposition extract per day, and still more preferably administered so that there is 450 μg/kg (body weight) or more of the bagasse decomposition extract per day. In addition, the dose is preferably administered so that there is 1,000 mg/kg (body weight) or less of the bagasse decomposition extract at one time, more preferably administered so that there is 800 mg/kg (body weight) or less of the bagasse decomposition extract at one time, and still more preferably administered so that there is 600 mg/kg (body weight) or less of the bagasse decomposition extract at one time. In addition, the dose is preferably administered so that there is 3,000 mg/kg (body weight) or less of the bagasse decomposition extract per day, more preferably administered so that there is 2,000 mg/kg (body weight) or less of the bagasse decomposition extract per day, and still more preferably administered so that there is 1,000 mg/kg (body weight) or less of the bagasse decomposition extract per day. Within this range, it is possible to achieve a sufficient concentration in the blood and it is possible to exhibit the bone metabolism improving action more effectively.

When the bone metabolism improving agent is administered parenterally, for example, the dose is preferably administered so that there is 50 μg/kg (body weight) or more of the bagasse decomposition extract at one time, more preferably administered so that there is 150 μg/kg (body weight) or more of the bagasse decomposition extract at one time, and still more preferably administered so that there is 250 μg/kg (body weight) or more of the bagasse decomposition extract at one time. In addition, the dose is preferably administered so that there is 100 μg/kg (body weight) or more of the bagasse decomposition extract per day, more preferably administered so that there is 300 μg/kg (body weight) or more of the bagasse decomposition extract per day, and still more preferably administered so that there is 500 μg/kg (body weight) or more of the bagasse decomposition extract per day. In addition, the dose is preferably administered so that there is 2,000 mg/kg (body weight) or less of the bagasse decomposition extract at one time, more preferably administered so that there is 1,500 mg/kg (body weight) or less of the bagasse decomposition extract at one time, and still more preferably administered so that there is 1,000 mg/kg (body weight) or less of the bagasse decomposition extract at one time. In addition, the dose is preferably administered so that there is 4,000 mg/kg (body weight) or less of the bagasse decomposition extract per day, more preferably administered so that there is 3,000 mg/kg (body weight) or less of the bagasse decomposition extract per day, and still more preferably administered so that there is 2,000 mg/kg (body weight) or less of the bagasse decomposition extract per day. Within this range, it is possible to achieve a sufficient concentration in the blood and it is possible to exhibit the bone metabolism improving action more effectively.

The bone metabolism improving agent of the present embodiment can be used for humans or animals. When the bone metabolism improving agent is used for animals, it can be used as feeds or feed additives. Examples of feed include companion animal feeds such as dog food and cat food, livestock feeds, poultry feeds, and feeds for farmed fish and shellfish. "Feed" includes anything that animals ingest orally for nutritional purposes. More specifically, if classified according to the nutrient content, it includes all of roughages, concentrated feeds, inorganic feeds, and special feeds, and if classified according to official standards, it includes all of formulated feeds, mixed feeds, and single feeds. In addition, if classified according to feeding methods, it includes all of feeds that are directly fed, feeds that are fed by mixing with other feeds, and feeds that are added to drinking water to supplement nutrients.

Since the above bone metabolism improving agent can improve bone metabolism of humans or animals other than humans, it can be used for preventing and treating bone-related diseases such as fracture, osteoporosis, and osteomalacia.

A specific mode of the bone formation promoting agent and the bone resorption inhibiting agent according to one embodiment may be the same mode as that of the above bone metabolism improving agent. That is, for the bone formation promoting agent or the bone resorption inhibiting agent according to one embodiment, in the above description of the bone metabolism improving agent, "bone metabolism improving agent" may be read as "bone formation promoting agent" or "bone resorption inhibiting agent."

One embodiment of the present invention can also provide a bone metabolism improving method, a bone formation promoting method, or a bone resorption inhibiting method including a step of administering an effective amount of a bone metabolism improving agent, a bone formation promoting agent, or a bone resorption inhibiting agent containing the above bagasse decomposition extract as an active ingredient to subject in need thereof. In addition, one embodiment of the present invention can provide a bagasse decomposition extract used for the bone metabolism improving method, the bone formation promoting method, or the bone resorption inhibiting method. The subjects in the above method may be mammals and are preferably humans. A mode, an administration method, a dose (intake), and the like of the bone metabolism improving agent, the bone formation promoting agent, or the bone resorption inhibiting agent may be the same as those described above.

Another embodiment of the present invention can also provide use of a bagasse decomposition extract for producing a bone metabolism improving agent, a bone formation promoting agent, or a bone resorption inhibiting agent. In addition, one embodiment of the present invention can also provide use of a bagasse decomposition extract for improving bone metabolism, for promoting bone formation or for inhibiting bone resorption. A mode of the bone metabolism improving agent, the bone formation promoting agent, or the bone resorption inhibiting agent may be the same as that described above.

EXAMPLES

While the present invention will be described below with reference to examples, the present invention is not limited to these examples. Hereinafter, the bagasse decomposition extract will be simply referred to as an "extract" in some cases.

Production of Bagasse Decomposition Extract

Production Example 1

15 kg of bagasse (water content 50 mass %) as a sugarcane promace and 100 L of a 0.5% (w/w) sodium hydroxide aqueous solution were mixed and subjected to an alkaline treatment under a condition of 150° C. The mixed solution after the alkaline treatment was separated into a solid content and a liquid content to obtain about 100 L of the liquid content. Ultrafiltration was performed using a UF membrane with a molecular weight cutoff of 2,500 (commercially available from SUEZ, GH8040F30) to obtain 80 L of a filtrate. 1 L of a synthetic adsorbing agent (HP-20 commercially available from Mitsubishi Chemical Corporation) was filled into a resin column (with an inner diameter of 80 mm and a height of 400 mm), and the above filtrate was caused to pass therethrough at a flow rate of 10 L/hour ($SV=10.0$ ($hour^{-1}$)) after the pH was adjusted to 6.

Then, 5 L of purified water was caused to pass through the resin column at a flow rate of 10 L/hour ($SV=10.0$ ($hour^{-1}$)) for washing. Next, 2 L of a 60% ethanol aqueous solution (ethanol/water=60/40 (volume/volume)) as an elution solvent was caused to pass through the resin column at a flow rate of 2 L/hour ($SV=2.0$ ($hour^{-1}$)). Subsequently, 2 L of purified water was caused to pass through the resin column at a flow rate of 2 L/hour ($SV=2.0$ ($hour^{-1}$)), and components adsorbed on the synthetic adsorbing agent were eluted. A fraction eluted from the resin column was concentrated under a reduced pressure to a concentration of about 10 times in a rotary evaporator and then freeze-dried overnight to obtain 20 g of a brown powder as a bagasse decomposition extract. This was used as an extract A.

Production Example 2

30 kg of bagasse (water content 50 mass %) as a sugarcane promace was hydrothermally treated with 100 L of hot water at 200° C. and 1.8 MPa. The mixed solution after the pretreatment was separated into a solid content and a liquid content to obtain about 88 L of the liquid content. Ultrafiltration was performed using a UF membrane with a molecular weight cutoff of 2,500 (commercially available from SUEZ, GH8040F30) to obtain 70 L of a filtrate. 1 L of a synthetic adsorbing agent (SP-850 commercially available from Mitsubishi Chemical Corporation) was filled into a resin column (with an inner diameter of 80 mm and a height of 400 mm), and 25 L of the above filtrate was caused to pass therethrough at a flow rate of 20 L/hour ($SV=20.0$ ($hour^{-1}$)).

Then, 3.3 L of purified water was caused to pass through the resin column at a flow rate of 20 L/hour ($SV=20.0$ ($hour^{-1}$)) for washing. Next, 2 L of a 60% ethanol aqueous solution (ethanol/water=60/40 (volume/volume)) as an elution solvent was caused to pass through the resin column at a flow rate of 2 L/hour ($SV=2.0$ ($hour^{-1}$)). Subsequently, 2 L of purified water was caused to pass through the resin column at a flow rate of 2 L/hour ($SV=2.0$ ($hour^{-1}$)), and components adsorbed on the synthetic adsorbing agent were eluted. A fraction eluted from the resin column was concentrated under a reduced pressure to a concentration of about 10 times in a rotary evaporator and then freeze-dried overnight to obtain 40 g of a brown powder as a bagasse decomposition extract. This was used as an extract W.

<Test A: Test for Anti-Obesity Agent>

Test Example A1: Test for Inhibiting Obesity Using Extract A

[Preparation of Test Solution]

The extract A was dissolved in water to prepare 50 mg/mL of a test solution stock solution. The test solution stock solution was diluted with a DMEM culture medium to prepare a test solution with a specimen concentration of 2,000 μg/mL.

[3T3-L1 Cell Lipid Accumulation Inhibition Test]

(Culture of Cells)

3T3-L1 cells (National Institute of Biomedical Innovation, Health and Nutrition) as mouse adipose progenitor cells were seeded on a 24-well plate, and cultured in a DMEM culture medium containing a newborn calf serum (10 vol %, with respect to a total amount of the culture medium) and a penicillin-streptomycin solution (1 vol %, with respect to a total amount of the culture medium) for 4 days. After the culturing, the medium was replaced with a DMEM culture medium containing a fetal bovine serum (10 vol %, with respect to a total amount of the culture medium) and a penicillin-streptomycin solution (1 vol %, with respect to a total amount of the culture medium), and 3T3-L1 cells were differentiated into adipocytes using an Adipogenesis Assay Kit (commercially available from Cayman Chemical Company). In this case, 2,000 μg/mL of the prepared test solution was added so that the final concentration was 1,000 μg/mL (Example a1). After culturing for 3 days, the medium was replaced with a newly prepared test solution-added culture. In addition, the same test was performed on progenitor cells in which differentiation induction using an Adipogenesis Assay Kit was not performed (undifferentiated a1-1), an untreated control to which no test solution was added (Comparative Example a1-1), and a positive control in which berberine chloride (commercially available from Wako Pure Chemical Corporation) was added so that the final concentration was 1 μg/mL (Positive Control a1-1). These were additionally cultured for 4 days.

(Staining of Cells)

After the culturing, the culture supernatant was removed, cells were fixed according to the procedure for the Adipogenesis Assay Kit, and the cells were then stained with Oil Red 0 solution serving a as a lipophilic pigment for staining lipid droplets.

[Observation of Lipid Droplets]

The results of the stained lipid droplets accumulated in adipocytes were observed using an inverted phase contrast microscope. The observation results of respective samples are shown in FIG. 1. FIG. 1(a) shows the observation results of the progenitor cells (undifferentiated a1-1), FIG. 1(b) shows the observation results of Comparative Example a1-1, FIG. 1(c) shows the observation results of Positive Control a1-1, and FIG. 1(d) shows the observation results of Example a1. As a result, in the adipocytes of Comparative Example a1-1, accumulation of lipid droplets stained with Oil Red 0 was observed, but in the adipocytes of Example a1, the number of accumulated lipid droplets was smaller than that of the adipocytes of Comparative Example a1-1.

[Measurement of Lipid Accumulation Rate]

After the lipid droplets were observed, a pigment extract solution contained in the Adipogenesis Assay Kit was added to samples of Example a1, Comparative Example a1-1, and Positive Control a1-1, and Oil Red O incorporated into the lipid droplets was extracted. The absorbance of the extracted Oil Red O at 520 nm was measured using a microplate reader (SpectraMax M2e, commercially available from Molecular Devices, LLC.).

The lipid accumulation rate was calculated from the absorbance of respective samples according to the following formula.

$$\text{Lipid accumulation rate (\%)} = \{(Sa - BL_{Avr})/(CN - BL_{Avr})_{Avr}\} \times 100$$

Sa: Absorbance of respective samples $BL_{Avr}$: average value of absorbances of progenitor cells (undifferentiated a1-1) (n=3)

CN: absorbance of Comparative Example a1-1 (untreated control)

$(CN-BL_{Avr})_{Avr}$: average value of values obtained by subtracting $BL_{Avr}$ from CN (n=3)

Figure 2:
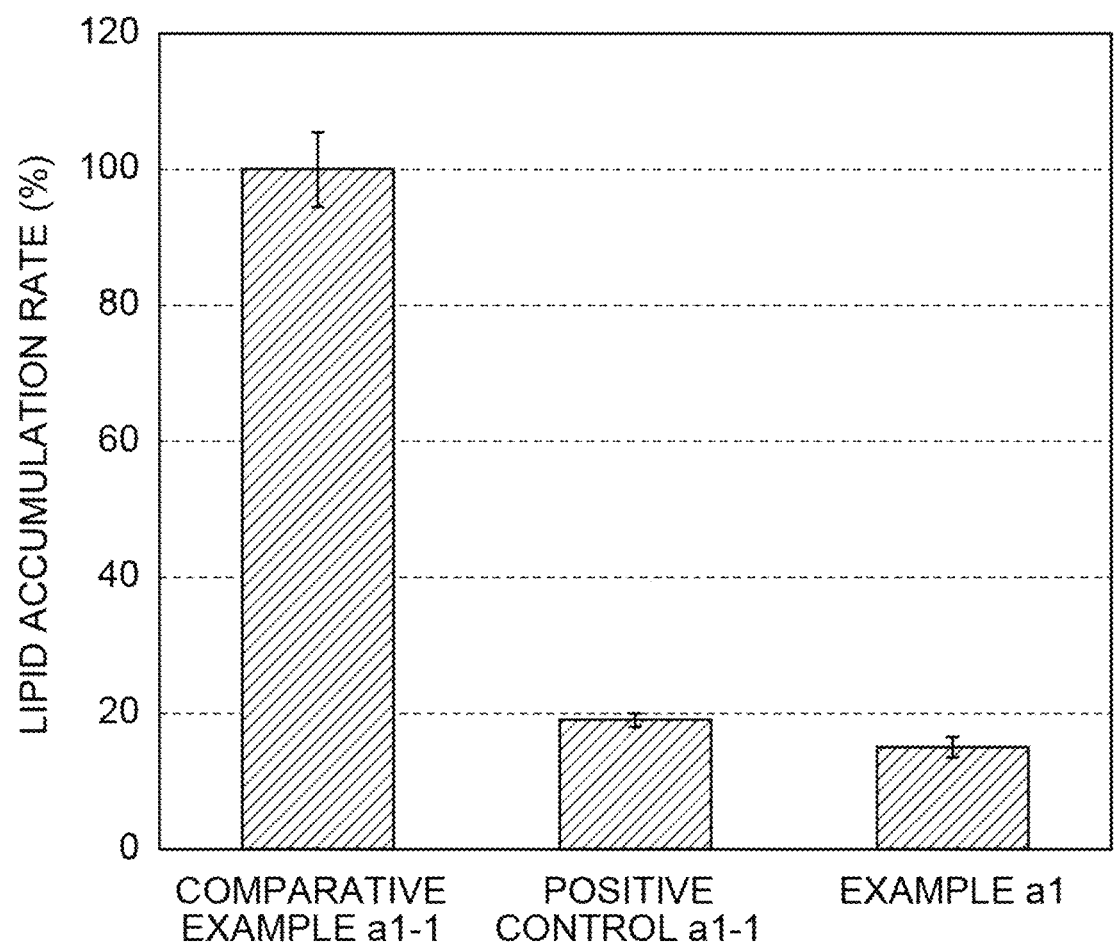
FIG. 2 is a graph showing lipid accumulation rates of Comparative Example a1-1, Positive Control a1-1 and Example a1.

The calculation results of lipid accumulation rates are shown in FIG. 2. The lipid accumulation rate was 100±5.5% for Comparative Example a1-1, 19±1.0 for Positive Control a1-1, and 15±1.5 for Example a1.

Test Example a2: Obesity Inhibition Test Using Extract W

[Preparation of Test Solution]

The extract W was dissolved in ethanol to prepare 50 mg/mL of a test solution stock solution. The test solution stock solution was diluted with a DMEM culture medium to prepare a test solution with a specimen concentration of 500 μg/mL.

[3T3-L1 Cell Lipid Accumulation Inhibition Test]

A lipid accumulation inhibition test was performed in the same method as in Test Example a1 except that the test solution containing the extract W prepared in the method in Test Example a1 was added so that the final concentration was 250 μg/mL (Example a2). As in Test Example a1, the same test was performed on progenitor cells in which differentiation induction using an Adipogenesis Assay Kit was not performed (undifferentiated a1-2), and an untreated control to which no test solution was added (Comparative Example a1-2).

[Observation of Lipid Droplets]

Figure 3:
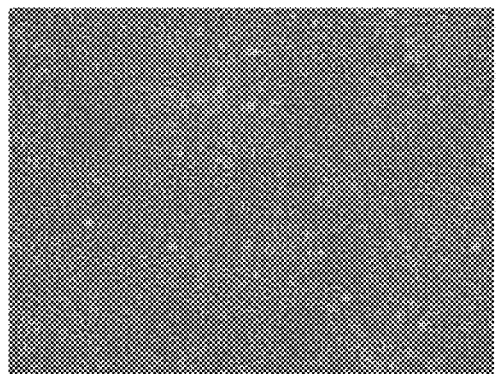
FIG. 3 shows microscopic images of results obtained by staining accumulated lipid droplets in progenitor cells (undifferentiated a1-2) and adipocytes in Comparative Example a1-2 and Example a2.
Figure 3:
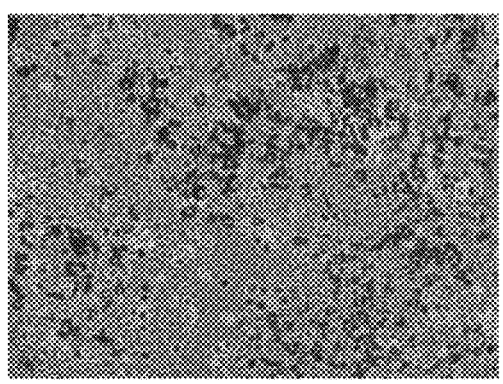
Figure 3:
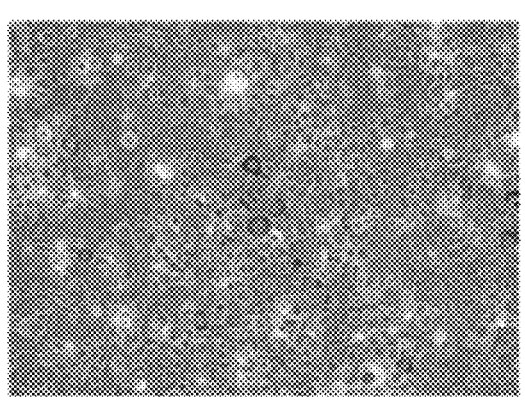

According to the same method as in Test Example a1, the results of the stained lipid droplets accumulated in adipocytes were observed. The observation results of respective samples are shown in FIG. 3. FIG. 3(a) shows the observation results of the progenitor cells (undifferentiated a1-2), FIG. 3(b) shows the observation results of Comparative Example a1-2, and FIG. 3(c) shows the observation results of Example a2. As a result, in the adipocytes of Comparative Example a1-2, accumulation of lipid droplets stained with Oil Red O was observed, but in the adipocytes of Example a2, the number of accumulated lipid droplets was smaller than that of the adipocytes of Comparative Example a1-2.

[Measurement of Lipid Accumulation Rate]

Figure 4:
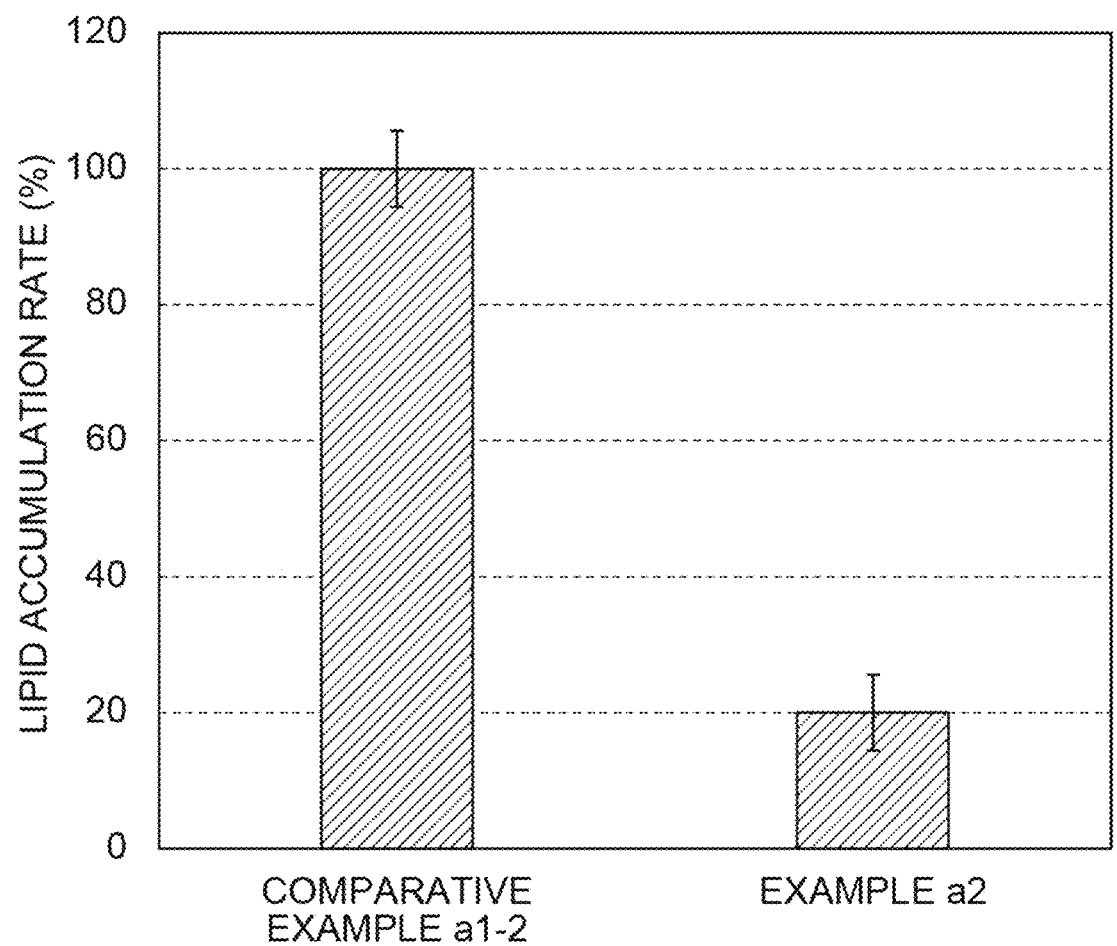
FIG. 4 is a graph showing lipid accumulation rates of Comparative Example a1-2 and Example a2.

After the lipid droplets were observed, lipid accumulation rates for Example a2 and Comparative Example a1-2 were calculated according to the same method as in Test Example a1. The results are shown in FIG. 4. The lipid accumulation rate was 100±5.6% for Comparative Example a1-2 and 20±5.6 for Example a2.

<Test b: Test for Anti-Dementia Agent>

[Preparation of Test Solution]

The above extract A and extract W in a powder state were stored at room temperature (controlled temperature: 18.0 to 28.0° C.) until they were subjected to the test. Water for injection (Otsuka distilled water, commercially available from Otsuka Pharmaceutical Factory, Inc.) was prepared as a medium in which the extract was dissolved. The required amount of the extract was weighed and dissolved in water for injection and then diluted to a predetermined concentration, and the result was used as a test solution.

[Preparation of Amyloid β Solution]

Amyloid β (Amyloid-βProtein (25-35), commercially available from Polypeptide Laboratories) used in an amyloid β solution was frozen (controlled temperature: −30° C. to −20° C. (measured value: −27.1° C. to −24.0° C.)) and stored until it was subjected to the test. Amyloid β was dissolved in water for injection to a concentration of 2 mM to prepare an amyloid β solution.

[Test Animals]

For test animals, male Slc: ddY mice (SPF, commercially available from Japan SLC, Inc.) were used. 5-week-old mice were acquired. Mice are an animal species generally used for behavioral pharmacology tests, and their strain maintenance is clear. The range of the body weight of the mice one day after acquisition was 23.8 to 30.0 g. A 5-day preliminary breeding period was set for the acquired mice.

(Breeding Conditions)

The mice were bred in an animal breeding room in which a controlled temperature of 20.0 to 26.0° C., a controlled humidity of 40.0 to 70.0%, light for 12 hours and dark for 12 hours (lighting: 6 am to 6 pm), and a ventilation frequency of 12 times/hour (fresh air that passed through a filter) were maintained.

Until the grouping date from the preliminary breeding period, 10 mice per cage were group-bred using a plastic cage (W: 310×D: 360×H: 175 mm), and after the grouping, 5 mice per cage were group-bred. Solid feed (MF, commercially available from Oriental Yeast Co., Ltd.) as feed and tap water as drinking water were freely ingested.

(Grouping Method and Solid Identification Method)

The grouping was performed on the day when administration of the test solution started so that the average body weight of each group was almost uniform according to a random sampling method. The groups were composed of four groups: pseudo-operation group, medium control group, extract A-administered group and extract W-administered group. In the extract A-administered group, the liquid dose was calculated at 10 mL/kg based on the body weight on the day of administration so that the dose of the extract A was 500 mg/kg per mouse. Similarly, in the extract W-administered group, the liquid dose was calculated at 10 mL/kg based on the body weight on the day of administration so that the dose of the extract W was 500 mg/kg per mouse. 10 mL/kg of a 0.5% (w/v) methyl cellulose solution was administered to the pseudo-operation group and the medium control group.

(Experiment Schedule)

The day when administration of the test solution started was set as the $1^{st}$ day of administration, the test solution was administered once a day, and the amyloid β solution was injected to the mice on the $8^{th}$ day of administration. Then, a Y-shaped maze test was performed on the $14^{th}$ day of administration. Respective procedures will be described below.

(Route of Administration of Test Solution and Administration Method)

The route of administration was oral administration. Regarding an administration method, the test solution was orally administered according to a general method used for a test instrument using a polypropylene disposable injection syringe (commercially available from Terumo Corporation) attached to a disposable oral sonde for mice (commercially available from Fuchigami Kikai Co., Ltd.). During the administration operation, the test solution was inverted and mixed whenever it was administered to each mouse and then aspired into the injection syringe. Here, on the day when the amyloid β solution was injected, the test solution was administered after the amyloid β solution was injected, and on the day when the Y-shaped maze test was performed, the test solution was administered 30 minutes before the measurement.

(Amyloid β Injection Method)

40 mg/kg of pentobarbital sodium (commercially available from Tokyo Chemical Industry Co., Ltd.) was intraperitoneally administered (liquid dose: 10 mL/kg) to mice and thus the mice were anesthetized. After the anesthesia, levobupivacaine hydrochloride (Popscaine (registered trademark) 0.25% injection, commercially available from Maruishi Pharmaceutical Co., Ltd.) was subcutaneously administered (0.1 mL) to the scalp. The scalp was incised to expose the skull, and a hole for inserting a stainless steel pipe was made in the skull at 1 mm (right side) lateral to and 0.2 mm posterior to bregma using a dental drill. A silicon tube with an outer diameter of 0.5 mm and a stainless steel pipe connected to a microsyringe were vertically inserted to a depth of 2.5 mm from the surface of the bone. In the SCE1-administered group and the medium control group, 3 μL (6 nmol/3 μL) of the amyloid β solution was injected into the ventricle using a micro syringe pump over 3 minutes. On the other hand, in the pseudo-operation group, 3 μL of water for injection was injected according to the same method. After the injection, the stainless steel pipe that was inserted was left for 3 minutes, and the stainless steel pipe was slowly removed. Then, the hole in the skull was covered with a non-absorbable bone marrow hemostatic agent (Nestop (registered trademark), commercially available from Alfresa Pharma Corporation) and the scalp was sutured.

(Evaluation According to Y-Shaped Maze Test)

A Y-shaped maze test (for example, Non-Patent Literature 1), which is a learning and memory behavior evaluation method and is particularly known as a short-term memory evaluation method, was performed. In the test, a plastic Y-shaped maze in which the length of one arm was 39.5 cm, the width of the floor was 4.5 cm, the height of the wall was 12 cm, and three arms were branched at 120 degrees (commercially available from Unicom Co., Ltd.) was used.

Before evaluation, the illuminance on the floor of the device was adjusted to 10 to 40 lux. The evaluation was performed 30 minutes after the test solution was administered. Mice were placed on any arm of the Y-shaped maze, and allowed to freely explore the maze for 8 minutes. The order of the arms that the mice moved within a measurement time was recorded, the number of times the mice moved to the arms was determined, and this was used as a total number of entries. Next, among these, a combination in which three different arms were selected in succession was examined, and this was used as a number of spontaneous alternation. Then, the spontaneous alternation rate was calculated using the following formula.

Spontaneous alternation rate (%)=[number of spontaneous alternation/(total number of entries−2)]×100

Figure 5:
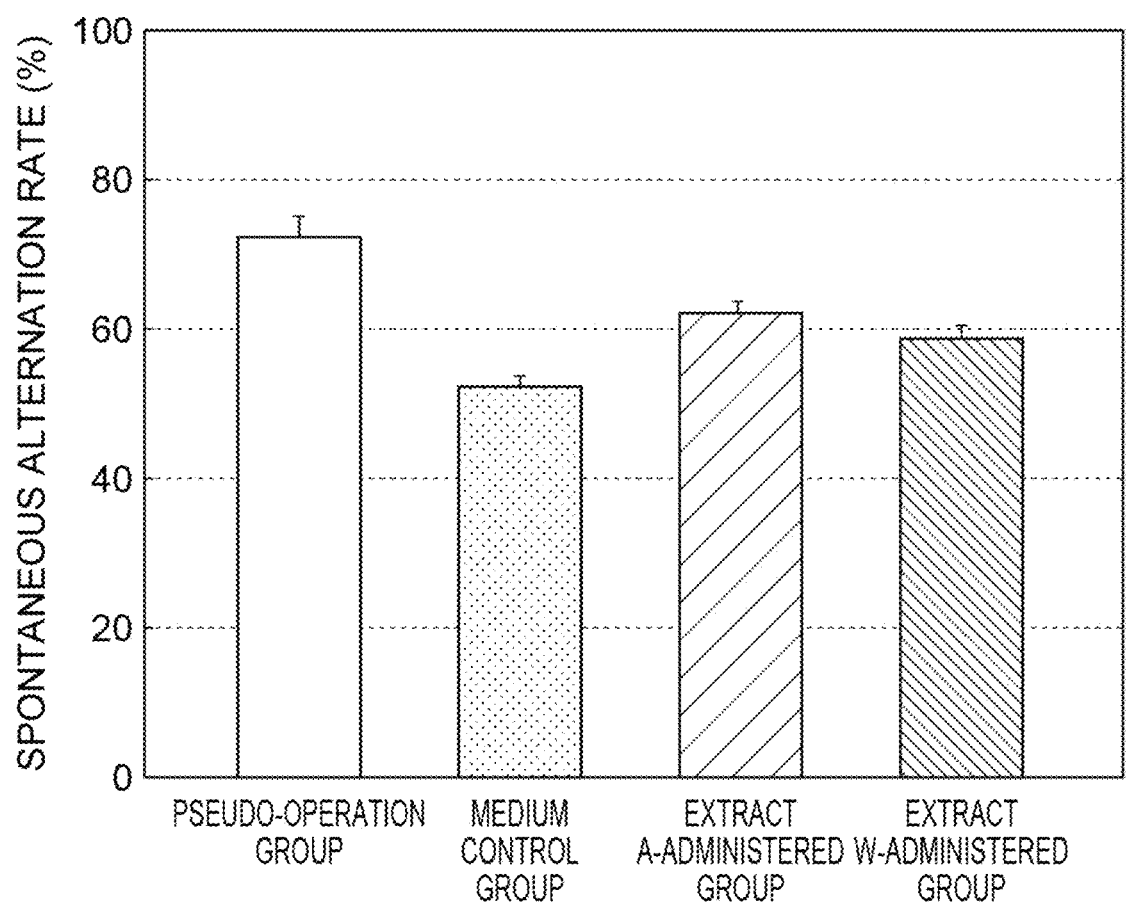
FIG. 5 is a graph showing the evaluation results in a Y-shaped maze test.

The Y-shaped maze test was performed on mice in each group, and a total number of entries, a number of spontaneous alternation, and an average value and a standard error of spontaneous alternation rates were calculated. Here, in the significance test, two-group comparison was performed for the pseudo-operation group and the medium control group, and the medium control group and the extract-administered group. In the two-group comparison test, the homogeneity test was performed according to the F test, and in the case of homogeneity, the Student's t-test was performed, and in the case of heteroscedasticity, the Aspin-Welch test was performed. The significance level was a risk rate of 1%. In the significance test, commercially available statistical program (SAS system, commercially available from SAS Institute Japan) was used. The results are shown in Table 1 and FIG. 5. As shown in Table 1 and FIG. 5, the medium control group had a lower value of the spontaneous alternation rate than the pseudo-operation group, and a significant difference was observed (p<0.01). The extract A-administered group had a higher value of the spontaneous alternation rate than the medium control group, and a significant difference was observed (p<0.01). In addition, the extract W-administered group had a higher value of the spontaneous alternation rate than the medium control group, and a significant difference was observed (p<0.05).

TABLE 1

|  | Pseudo-operation group | Medium control group | Extract A-administered group | Extract W-administered group |
| --- | --- | --- | --- | --- |
| Total number of entries | 34.2 ± 1.6 | 37.0 ± 2.1 | 38.8 ± 2.6 | 46.25 ± 4.4 |
| Number of spontaneous alternation | 23.1 ± 1.1 | 18.3 ± 1.1 | 22.9 ± 1.8 | 25.75 ± 2.3 |
| Spontaneous alternation rate (%) | 72.3 ± 2.8 | 52.3 ± 1.4 | 62.1 ± 1.6 | 58.7 ± 1.8 |

<Test c: Test for Deodorant>
<Preparation of Extract Solution>

The above extract A was dissolved in 20% ethanol to prepare an extract solution A having a solid content of 30% (w/w).

Test Example c1: Deodorizing Effect on Isovaleric Acid 0.17 g of the extract solution A was dissolved in 1 mL of 20% ethanol and 1 mL of water was then added thereto, and additionally dissolved. 9 mL of water was added to 1 mL of the solution after dissolution to prepare a dissolved solution containing the extract solution A (dissolved solution (A1)).

10 mL of an aqueous solution containing 1 ppm (w/v) of isovaleric acid and 0.2 mL of the dissolved solution (A1) were put into a 15 mL centrifuge tube to prepare a sample solution (1) (the extract solution A with a final concentration of 0.017% (w/v)).

As a control, a mixed solution containing 10 mL of an aqueous solution containing 1 ppm (w/v) of isovaleric acid and 0.2 mL of water was prepared (control (1)).

10 panelists evaluated the degree of odor of the sample solution (1) and the control (1) based on the following evaluation criteria.
  0: No odor
  1: Barely noticeable
  2: Clearly noticeable
  3: Slightly strong odor
  4: Strong odor As a result of calculating the average value of the evaluation points, the result was 2.8 for the control (1) and 1.2 for the sample solution (1). The multiple comparison test according to the Bonferroni method was performed, and a significant difference was observed in the difference between these evaluation points.

Test Example c2: Deodorizing Effect on Acetic Acid 10 mL of 0.1% acetic acid and 0.2 mL of the above dissolved solution (A1) were put into a 15 mL centrifuge tube to prepare a sample solution (2) (the extract solution A with a final concentration of 0.017% (w/v)).

As a control, a mixed solution containing 10 mL of 0.1% acetic acid and 0.2 mL of water was prepared (control (2)).

9 panelists evaluated the degree of odor of the sample solution (2) and the control (2) based on the same evaluation criteria as in Test Example c1.

When the average value of the evaluation points was calculated, the average value was 2.78 for the control (2) and 1.8 for the sample solution (2). The multiple comparison test according to the Bonferroni method was performed, and a significant difference was observed in the difference between these evaluation points.

Test Example c3: Deodorizing Effect on Methyl Mercaptan 10 mL of an aqueous solution containing 0.1 ppm of methyl mercaptan and 0.2 mL of the above dissolved solution (A1) were put into a 15 mL centrifuge tube to prepare a sample solution (3) (the extract solution A with a final concentration of 0.017% (w/v)).

As a control, a mixed solution containing 10 mL of 0.1 ppm (w/v) methyl mercaptan and 0.2 mL of water was prepared (control (3)).

9 panelists evaluated the degree of odor of the sample solution (3) and the control (3) based on the same evaluation criteria as in Test Example c1.

When the average value of the evaluation points was calculated, the average value was 3.11 for the control (3) and 2.41 for the sample solution (2). The multiple comparison test according to the Bonferroni method was performed, and a significant difference was observed in the difference between these evaluation points.

Test Example c4: Deodorizing Effect on Trimethylamine 10 mL of an aqueous solution containing 1 ppm (w/v) of trimethylamine and 0.2 mL of the above dissolved solution (A1) were put into a 15 mL centrifuge tube to prepare a sample solution (4) (the extract solution A with a final concentration of 0.017% (w/v)).

As a control, a mixed solution containing 10 mL of an aqueous solution containing 1 ppm (w/v) of trimethylamine and 0.2 mL of water was prepared (control (4)).

10 panelists evaluated the degree of odor of the sample solution (4) and the control (4) based on the same evaluation criteria as in Test Example c1.

When the average value of the evaluation points was calculated, the average value was 2.25 for the control (4) and 1.28 for the sample solution (4). The multiple comparison test according to the Bonferroni method was performed, and a significant difference was observed in the difference between these evaluation points.

Test Example c5: Deodorizing Effect on Diacetyl 10 mL of an aqueous solution containing 2 ppm (w/v) of diacetyl and 0.2 mL of the above dissolved solution (A1) were put into a 15 mL centrifuge tube to prepare a sample solution (5) (the extract solution A with a final concentration of 0.017% (w/v)).

As a control, a mixed solution containing 10 mL of an aqueous solution containing 2 ppm (w/v) of diacetyl and 0.2 mL of water was prepared (control (5)).

9 panelists evaluated the degree of odor of the sample solution (5) and the control (5) based on the same evaluation criteria as in Test Example c1.

When the average value of the evaluation points was calculated, the average value was 2.78 for the control (5) and 1.67 for the sample solution (5). The multiple comparison test according to the Bonferroni method was performed, and a significant difference was observed in the difference between these evaluation points.

Test Example c6: Deodorizing Effect on Nonenal 10 mL of an aqueous solution containing 0.01 ppm (w/v) of nonenal and 0.4 mL of the above dissolved solution (A1) were put into a 15 mL centrifuge tube to prepare a sample solution (6) (the extract solution A with a final concentration of 0.034% (w/v)).

As a control, a mixed solution containing 10 mL of an aqueous solution containing 0.01 ppm (w/v) of nonenal and 0.4 mL of water was prepared (control (6)).

11 panelists evaluated the degree of odor of the sample solution (6) and the control (6) based on the same evaluation criteria as in Test Example c1.

When the average value of the evaluation points was calculated, the average value was 2.42 for the control (6) and 1.45 for the sample solution (6). The multiple comparison test according to the Bonferroni method was performed, and a significant difference was observed in the difference between these evaluation points.

Test Example c7: Deodorizing Effect on Ammonium Thioglycolate 10 mL of an aqueous solution containing 0.85% (w/v) of ammonium thioglycolate and 0.4 mL of the above dissolved solution (A1) were put into a 15 mL centrifuge tube to prepare a sample solution (7) (the extract solution A with a final concentration of 0.034% (w/v)).

As a control, a mixed solution containing 10 mL of an aqueous solution containing 0.85% (w/v) of ammonium thioglycolate and 0.4 mL of water was prepared (control (7)).

10 panelists evaluated the degree of odor of the sample solution (7) and the control (7) based on the same evaluation criteria as in Test Example c1.

When the average value of the evaluation points was calculated, the average value was 3.08 for the control (7) and 1.83 for the sample solution (7). The multiple comparison test according to the Bonferroni method was performed, and a significant difference was observed in the difference between these evaluation points.

Test Example c8: Deodorizing Effect on Monoethanolamine Thioglycolate 10 mL of an aqueous solution containing 0.085% (w/v) of monoethanolamine thioglycolate and 0.4 mL of the above dissolved solution (A1) were put into a 15 mL centrifuge tube to prepare a sample solution (8) (the extract solution A with a final concentration of 0.034% (w/v)).

As a control, a mixed solution containing 10 mL of an aqueous solution containing 0.085% (w/v) of monoethanolamine thioglycolate and 0.4 mL of water was prepared (control (8)).

10 panelists evaluated the degree of odor of the sample solution (8) and the control (8) based on the same evaluation criteria as in Test Example c1.

When the average value of the evaluation points was calculated, the average value was 3.3 for the control (8) and 2.38 was for the sample solution (8). The multiple comparison test according to the Bonferroni method was performed, and a significant difference was observed in the difference between these evaluation points.

Test Example c9: Deodorizing Effect on Cigarette Odor 0.17 g of the extract solution A was dissolved in 1 mL of 20% ethanol and 1 mL of water was then added thereto, and additionally dissolved. 30 mL of water was added to 0.3 mL of the solution after dissolution to prepare a dissolved solution containing the extract solution A (dissolved solution (A2)).

A 5 L Erlenmeyer flask was turned upside down, a lit cigarette was put about 5 cm into the mouth of the Erlenmeyer flask, and cigarette smoke was collected for about 30 to 40 seconds. Three 10 cm×10 cm fabric (cotton towel) pieces were put into the Erlenmeyer flask in which smoke was collected and the flask was quickly sealed, the fabric pieces were allowed to absorb smoke while shaking the flask. After 5 minutes, the towel was removed and used as a test fabric.

The dissolved solution (A2) was sprayed onto the test fabric 5 times (0.15 mL×5 times=about 0.75 mL) and the test fabric was then rubbed well and made uniform to obtain a sample (9).

As a control, a test fabric onto which water was sprayed 5 times (about 0.75 mL) was prepared (control (9)).

9 panelists evaluated the degree of odor of the sample (9) and the control (9) based on the same evaluation criteria as in Test Example c1.

When the average value of the evaluation points was calculated, the average value was 1.89 for the control (9) and 0.61 for the sample (9). The multiple comparison test according to the Bonferroni method was performed, and a significant difference was observed in the difference between these evaluation points.

<Test d: Test for Anti-Aging Agent>

Test Example d1: MMP-1 Production Inhibition Test

The production inhibitory effect of the extract A and the extract W on MMP-1 was examined by evaluating an inhibiting action of MMP-1 on normal human fibroblasts.

Test Example d1-1

As a culture medium for culturing normal human fibroblasts, a Dulbecco's modified MEM culture medium containing a 5% calf serum (commercially available from Kurabo Industries Ltd., hereinafter referred to as a "5% FBS-DMEM culture medium") was used. A culture medium in which the extract A with a concentration shown in Table 2 was contained in a 5% FBS-DMEM culture medium was prepared, and this was used as a culture medium containing a test sample.

Normal human fibroblasts (commercially available from Kurabo Industries Ltd.) were seeded in a 96-well microplate at a density of $2.0 \times 10^4$ cells/well together with a 5% FBS-DMEM culture medium. After 24 hours from the seeding, the 5% FBS-DMEM culture medium in the microplate was replaced with the culture medium containing the test sample including the extract A. After the culture medium was replaced, culturing was additionally performed for 24 hours, and the culture medium containing the test sample was then replaced with a Hanks' buffer solution (containing $Ca^{2+}$ and $Mg^{2+}$, HBS (+)). Immediately thereafter, the medium was replaced with a culture medium containing a fresh test sample, and culturing was additionally performed for 24 hours. After the culturing, the culture supernatant was collected and subjected to ELISA.

ELISA was performed according to the sandwich method and performed according to the following method. Anti-human MMP-1 antibodies were added to a high adsorption type ELISA plate, and then coated at room temperature overnight, and then blocked with a 1% bovine albumin (BSA) for 1 hour. After blocking, a culture supernatant and MMP-1 for calibration curves were added and the mixture was incubated at room temperature for 2 hours, and anti-human MMP-1 biotinylated antibodies were then added, and the mixture was then incubated at room temperature for 1.5 hours. In addition, streptavidin HRP was added thereto and the mixture was incubated at room temperature for 30 minutes. Next, a phosphoric acid-citric acid buffer solution (0.1 mol/L, pH 4.0) containing 0.3 mg/mL of 2,2'-azinobis (3-ethylbenzothiazolin-6-sulfonic acid)-diammonium salt (ABTS) and 0.03% (V/V) of hydrogen peroxide was added thereto and the mixture was reacted for 20 minutes. The absorbance at 405 nm in the microplate reader was measured.

The amount of MMP-1 in the culture supernatant was calculated from the calibration curve created with commercially available MMP-1. On the other hand, the cultured cells were lysed in a 0.5% (V/V) Triton X-100 buffer solution, and a total protein amount was quantified by the BCA method. The amount of MMP-1 produced per unit protein amount was calculated by dividing the amount of MMP-1 in the culture supernatant by the total protein amount in the cells. The results are shown in Table 2.

Test Example d1-2

The amount of MMP-1 produced per unit protein amount was calculated in the same method as in Test Example d1-1 except that, in Test Example d1-1, the culture medium containing the test sample was replaced with a Hanks' buffer solution (containing $Ca^{2+}$ and $Mg^{2+}$, HBS (+)), and ultraviolet A waves (UVA) with a dose of 4 $J/cm^2$ were then emitted, and the medium was then immediately replaced with a culture medium containing a fresh test sample. The results are shown in Table 2.

Test Example d1-3

The amount of MMP-1 produced per unit protein amount was calculated in the same method as in Test Example d1-2 except that, in Test Example d1-2, the extract W was used in place of the extract A, and the dose of ultraviolet A waves was changed to 5 $J/cm^2$. The results are shown in Table 2.

TABLE 2

| Concentration of extract (with respect to total amount of culture medium containing test sample, μg/mL) | Amount of MMP-1 produced (ng/μg proteins) | | Total amount of proteins (μg/well) |
|---|---|---|---|
| | Average ± standard deviation | p value (t test)[1] | Average ± standard deviation |
| Test Example d1-1 (Extract A) | | | |
| 0 | 113.7 ± 7.6 | 1.000 | 8.6 ± 0.2 |
| 4.68 | 104.6 ± 8.5 | 0.159 | 8.5 ± 0.1 |
| 18.75 | 92.6 ± 12.6 | 0.029* | 8.8 ± 0.2 |
| 75 | 57.7 ± 5.2 | 0.000* | 9.5 ± 0.2 |
| 300 | 26.7 ± 2.9 | 0.000* | 9.5 ± 0.1 |
| Test Example d1-2 (Extract A) | | | |
| 0 | 133.1 ± 11.4 | 1.000 | 8.0 ± 0.3 |
| 4.68 | 114.2 ± 9.9 | 0.046* | 8.4 ± 0.4 |
| 18.75 | 90.8 ± 7.5 | 0.001* | 8.7 ± 0.2 |
| 75 | 75.7 ± 7.3 | 0.000* | 7.9 ± 0.3 |
| 300 | 2.3 ± 0.2 | 0.000* | 2.4 ± 0.2 |
| Test Example d1-3 (Extract W) | | | |
| 0 | 25.1 ± 5.1 | 1.000 | 7.3 ± 0.3 |
| 3.75 | 20.1 ± 1.5 | 0.070 | 7.7 ± 0.2 |
| 7.5 | 20.0 ± 3.3 | 0.098 | 7.6 ± 0.5 |
| 15 | 17.3 ± 2.2 | 0.014* | 7.6 ± 0.5 |
| 30 | 16.3 ± 0.8 | 0.005* | 7.3 ± 0.3 |

[1] significant difference with respect to test examples in which the concentration of the extract A or the extract W was 0 μg/mL
*p < 0.05, significant decrease

Test Example d2: Elastase Activity Inhibition Test

The elastase activity inhibitory effect of the extract A and the extract W was examined by evaluating an activity inhibiting action of a normal human fibroblast-derived elastase.

Test Example d2-1

A 0.5% (V/V) Triton X-100 buffer solution (1 mmol/L PMSF, 100 mmol/L tris hydrochloric acid buffer solution, pH 8.0) was added to normal human fibroblasts maintained in a confluence in a 10 cm² petri dish, and the cells were lysed, and this was used as a crude enzyme solution containing a fibroblast-derived elastase. Succinyl-L-alanyl-L-alanyl-L-alanine p-nitroanilide (Suc-Ala-Ala-Ala-pNA, 5 mmol/L, commercially available from BACHEM AG) was used as a substrate for the elastase. As a test solution, the extract A was dissolved in a tris buffer solution to prepare a test solution with a predetermined concentration. 6.25 mmol/L of EDTA was used as a positive control.

50 μL of the test solution was added to each well of a 96-well microplate. In addition, a 100 mmol/L tris hydrochloric acid buffer solution (pH 8.0) containing 5 mmol/L of Suc-Ala-Ala-Ala-pNA was prepared, and 100 μL each of the solution was added. Here, 50 μL of the elastase crude enzyme solution was added to each well to obtain a reaction solution. In the reaction solution immediately after the elastase crude enzyme solution was added, the absorbance at 405 nm was measured as an absorbance before the reaction (blank absorbance). Then, in the reaction solution after it was left at 37° C. for 2 hours and reacted, the absorbance at 405 nm was measured (the absorbance after the reaction). Using the value obtained by subtracting the blank absorbance from the absorbance after the reaction, the absorbance when no test solution was added was set as C', and the absorbance when the test solution was added was set as S,' the elastase activity inhibition rate (%) was determined according to the following formula. The results are shown in Table 3. The extract A exhibited a significant elastase activity inhibitory effect at p<0.05.)

Elastase inhibition rate (%)=(1−(S'/C'))×100

Test Example d2-2

The elastase activity inhibition rate of the extract W was determined in the same method as in Test Example d2-1 except that the extract W was used in place of the extract A. Here, 12.25 mmol/L of EDTA was used as a positive control. The elastase activity inhibitory effect was also observed in the extract W.

TABLE 3

| | Concentration of extract (with respect to total amount of reaction solution, μg/mL) | Elastase activity inhibition rate %) | |
|---|---|---|---|
| | | Average ± standard deviation | p value (t test)[2] |
| Test Example d2-1 (Extract A) | 0 | 0.00 ± 1.64 | 1.000 |
| | 37.5 | 9.44 ± 2.10 | 0.000* |
| | 75 | 13.48 ± 1.92 | 0.000* |
| | 150 | 20.88 ± 1.79 | 0.000* |
| | 300 | 30.92 ± 2.20 | 0.000* |
| | Positive control | 47.74 ± 0.27 | 0.000* |
| Test Example d2-2 (Extract W) | 0 | 0.00 ± 1.09 | 1.000 |
| | 75 | 1.74 ± 2.00 | 0.178 |
| | 150 | 7.51 ± 1.78 | 0.000* |
| | 300 | 17.96 ± 2.07 | 0.000* |
| | Positive control | 48.80 ± 0.48 | 0.000* |

[2] significant difference with respect to test examples in which the concentration of the extract A was 0 μg/mL
*p < 0.05, significant decrease

Test Example d3: Fibroblast Activation Test

The activation action of the extract A on fibroblasts was examined by the MTT method.

The same medium as in Test Example d1 was used as a culture medium for culturing normal human fibroblasts. The extract A was dissolved in water to prepare a culture medium in which the extract A with a concentration shown in Table 4 was contained in a 1% FBS-DMEM culture medium and this was used as a culture medium containing a test sample. A 5% FBS-DMEM culture medium was used as a positive control.

Normal human fibroblasts (commercially available from Kurabo Industries Ltd.) were seeded in a 96-well microplate at a density of 2.0×10⁴ cells/well together with a 5% FBS-DMEM culture medium. After 24 hours from the seeding, the 5% FBS-DMEM culture medium in the microplate was replaced with the culture medium containing the test sample including the extract A. After the culture medium was replaced, culturing was additionally performed for 48 hours, the medium was then replaced with a 1% FBS-DMEM culture medium containing 0.4 mg/mL of 3-(4,5-dimethyl-thiazolyl-2-yl)-2,5-diphenyltetrazolium bromide (MTT), and culturing was performed for 2 hours. The culture medium was removed, and 2-propanol was added to extract the produced blue formazan. The absorbance at 550 nm of the extract solution was measured and this was used as an amount of the blue formazan. A ratio (percentage) of the amount of blue formazan when the extract A was used to the amount of blue formazan produced when the concentration of the extract A (with respect to a total amount of the culture medium containing the test sample) was 0 μg/mL was calculated and used as a cell activation rate. A higher value of the cell activation rate indicated a stronger cell activation action. The results are shown in Table 4.

TABLE 4

| Concentration of extract A (with respect to total amount of culture medium containing test sample, μg/mL) | Cell activation rate (%) | |
|---|---|---|
| | Average ± standard deviation | p value (t test)[3] |
| 0 | 100 ± 10.5 | 1.000 |
| 37.5 | 110.5 ± 1.6 | 0.057 |
| 75 | 119.2 ± 1.4 | 0.004* |
| 150 | 128.0 ± 2.3 | 0.000* |
| 300 | 122.4 ± 7.8 | 0.005* |
| Positive control | 155.8 ± 6.5 | 0.000* |

[3]significant difference with respect to test examples in which the concentration of the extract A was 0 μg/mL
*p < 0.05, significant decrease <Test e: Test for Anti-Glycation Agent>
<Evaluation of Anti-Glycation Activity of Extract a (Test Examples e1 to e2)>

Test Example e1: Evaluation of Anti-Glycation Activity in Human Serum Albumin Model The anti-glycation activity (AGEs production inhibitory action) of the bagasse decomposition extract (the extract A) with respect to AGEs produced by the reaction of glucose-human serum albumin (HSA) was examined.
(Sample Preparation)
The extract A as a bagasse decomposition extract was dissolved in distill water to a concentration of 100 mg/mL to prepare a test solution stock solution. The test stock solution was diluted with distill water to prepare a 0.01 to 100 mg/mL solution. This solution was used as a test sample. As a positive control, an aqueous solution (concentration of 3.0 mg/mL) containing aminoguanidine as a glycation reaction inhibitor was prepared.
(Glycation Reaction Conditions)
The prepared sample with each concentration was added to a reaction solution containing a 0.1 mol/L phosphate buffer solution (pH 7.4), 8 mg/mL human serum albumin (HSA, commercially available from Sigma-Aldrich), and a 0.2 mol/L glucose aqueous solution to a concentration of 1/10 (final reaction concentration), and incubated at 60° C. for 40 hours. As a negative control, a solution to which distilled water was added was used in place of the sample. As a positive control, the above aminoguanidine aqueous solution was used. Here, as a blank for the positive control, a solution to which distilled water was added in place of glucose was used.
(Measurement of Anti-Glycation Activity)
After the glycation reaction was completed, fluorescent AGEs produced in the reaction solution were measured using a microplate reader (SpectraMax i3, commercially available from Molecular Devices, LLC.) (an excitation wavelength of 370 nm and a fluorescence wavelength of 440 nm). The inhibition rate of AGEs production (hereinafter simply referred to as an "inhibition rate") was calculated according to the following formula when the fluorescence intensity of the reaction solution in which the sample was added in the glycation reaction was set as $F_1$, the fluorescence intensity of the reaction solution incubated after distilled water was added in place of the glucose aqueous solution was set as $F_2$, the fluorescence intensity of the reaction solution incubated without adding the bagasse decomposition extract or aminoguanidine was set as $F_3$, and the fluorescence intensity of the reaction solution incubated without adding the bagasse decomposition extract or aminoguanidine while adding distilled water in place of the glucose aqueous solution as a blank was set as F4.

Fluorescent AGEs inhibition rate (%)=$(1-(F_1-F_2)/(F_3-F_4))\times 100$

Figure 6:
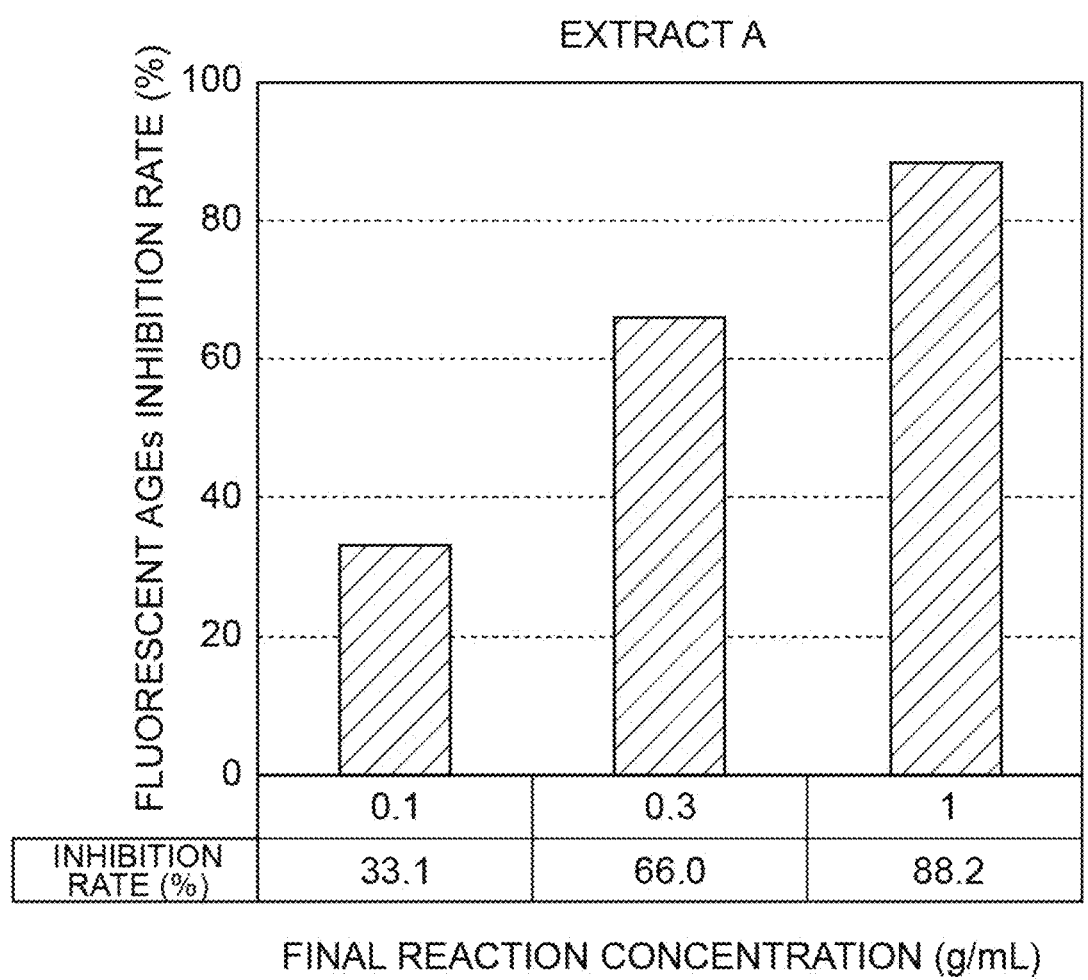
FIG. 6 is a graph showing the results in Test Example e1.

The inhibition rates of fluorescent AGEs (HSA) in the bagasse decomposition extract (the extract A) with each final reaction concentration (0.1 mg/mL, 0.3 mg/mL, or 1 mg/mL) are shown in FIG. 6. As shown in FIG. 6, the extract A had an inhibition rate that increased in a concentration-dependent manner and exhibited the anti-glycation activity (fluorescent AGEs (HSA) production inhibitory action). The inhibition rate of fluorescent AGEs (HSA) with 0.3 mg/mL of aminoguanidine as a positive control was 81.2±1.4%. It was confirmed that aminoguanidine had an anti-glycation activity (fluorescent AGEs (HSA) production inhibitory action). $IC_{50}$ (50% production inhibition concentration) calculated from the inhibition rate of the sample at each concentration of the extract A was 0.19 mg/mL, and in the human serum albumin model, the extract A exhibited the anti-glycation activity.

Test Example e2: AGEs Crosslinking Cutting Test (Evaluation of AGEs Decomposition Activity)

Next, according to the AGEs crosslinking cutting test, the AGEs decomposition activity of the bagasse decomposition extract (the extract A) was evaluated. The AGEs decomposition activity (AGEs crosslinking cutting action) was evaluated by a method using a reaction system in which 1-phenyl-1,2-propanedione (1-phenyl-1,2-propanedione: PPD) having an α-diketone structure was used as a model substrate, which is a known method (for example, Glycative Stress Research 2015, Vol. 2 (No. 2), pp. 58-66).
(Sample Preparation)
The extract A as a bagasse decomposition extract was dissolved in distill water to a concentration of 20 mg/mL to prepare a test sample.
(Crosslinking Cutting Reaction Conditions)
The above prepared sample was added to a reaction solution containing a 0.16 mol/L phosphate buffer solution (pH 7.4), and a 2 mmol/mL PPD composition to a concentration of ½ (10 mg/mL) and incubated at 37° C. for 8 hours. As a negative control, a solution to which distilled water was added was used in place of the sample. As a positive control, PTB (N-phenacylthiazoliumbromide) was used. The reaction solution was centrifuged at 20° C. and 3,000×g, for 10 minutes to obtain a supernatant. The amount of benzoic acid in the supernatant was analyzed through reversed phase HPLC. The amount of benzoic acid in the reaction solution was determined by subtracting the amount of benzoic acid in the sample that was separately measured. Since 1 mol of PPD produced 1 mol of benzoic acid, the crosslinking cutting rate was calculated according to the following formula.

Crosslinking cutting rate (%)=$\{(A-B)/C\}\times 100$

A: the amount of benzoic acid in the reaction solution
B: the amount of benzoic acid in the sample
C: the amount of PPD used in the reaction (the amount of the substrate)
(Crosslinking Cutting Test Results)
When the crosslinking cutting rate in the sample and the PTB solution (5 mmol/L) and the value of the crosslinking cutting rate (a relative value of the cutting rate) in the sample when PTB (5 mmol/L) was set as 100% were determined, the crosslinking cutting rate of the sample was 8.50, the crosslinking cutting rate of PTB was 20.1, and the relative value of the cutting rate of the sample was 42.29%. Therefore, the extract A exhibited the AGEs decomposition activity.

<Evaluation of Anti-Glycation Activity of Extract W (Test Examples e3 to e4)>

Figure 7:
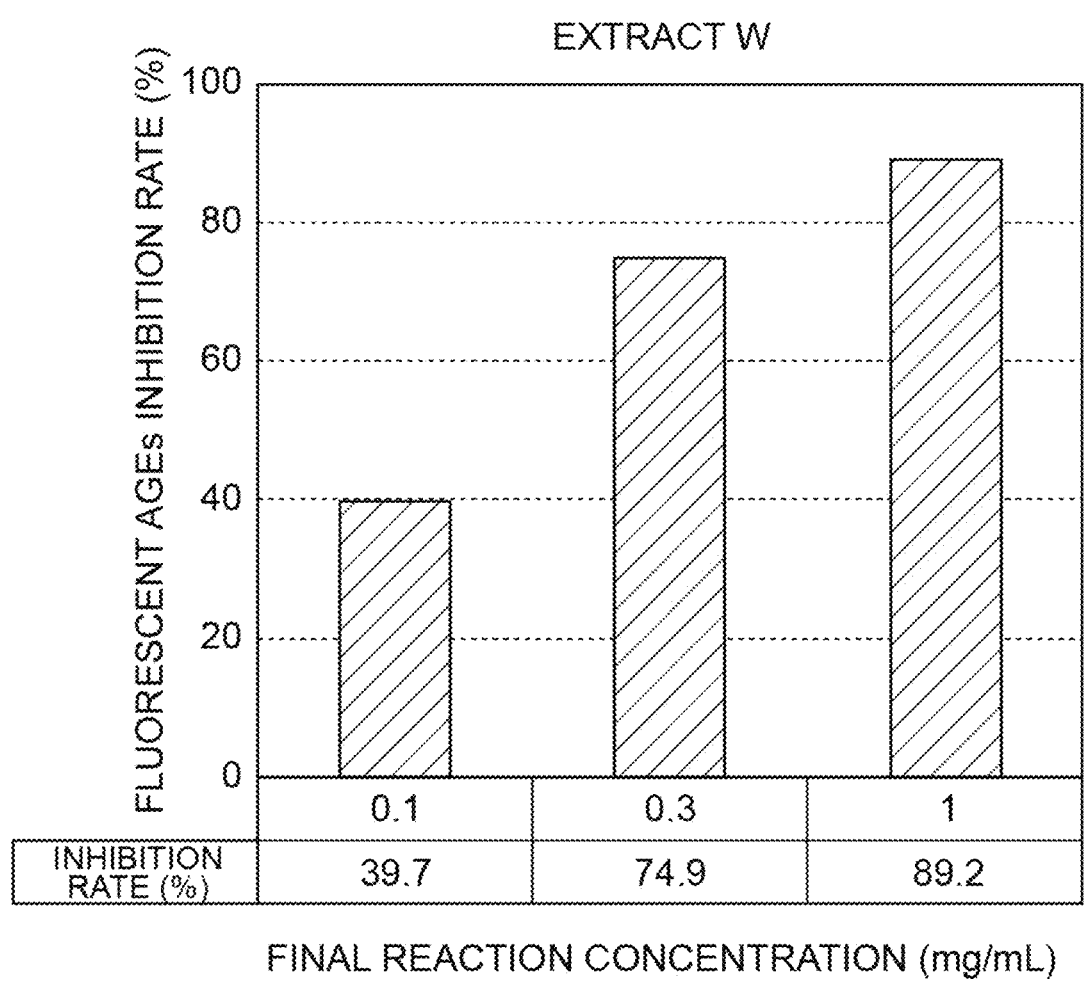
FIG. 7 is a graph showing the results in Test Example e3.

Test Example e3: Evaluation of Anti-Glycation Activity in Human Serum Albumin Model The anti-glycation activity was evaluated in the same manner as in Test Example e1 except that the above extract W was used as a bagasse decomposition extract, and dimethyl sulfoxide (DMSO) was used in place of distill water in preparing a sample. As a positive control, an aqueous solution containing aminoguanidine (final concentration of 0.3 mg/mL) was used. The inhibition rate of fluorescent AGEs (HSA) with 0.3 mg/mL of aminoguanidine as a positive control was 74.6±0.8%. The measurement results are shown in FIG. 7. In addition, $IC_{50}$ (50% production inhibition concentration) calculated from the inhibition rate of the sample at each concentration of the extract W was 0.14 mg/mL, and the extract W exhibited the anti-glycation activity.

Test Example e4: AGEs Crosslinking Cutting Test (Evaluation of AGEs Decomposition Activity)

(Preparation of Sample)
The extract W as a bagasse decomposition extract was dissolved in 50% DMSO to prepare 20 mg/mL of a solution. This solution was serially-diluted in 50% DMSO to prepare a test sample. As a positive control, a 10 mmol/L PTB (N-phenacylthiazoliumbromide) solution was used.
(Crosslinking Cutting Reaction Conditions)
A test solution or a PTB solution (10 mmol/L), a 10 mmol/LPPD solution, and a 0.2 mol/L phosphate buffer solution (pH 7.4) were mixed at a ratio of 5:1:4 and reacted at 37° C. for 8 hours (n=3). After the reaction was completed, hydrochloric acid was added to stop the reaction. Then, the reaction solution was centrifuged at 20° C. and 3,000×g, for 10 minutes, and the amount of benzoic acid in the supernatant was analyzed through reversed phase HPLC. The amount of benzoic acid in the reaction solution was determined by subtracting the amount of benzoic acid in the sample that was separately measured. Since 1 mol of PPD produced 1 mol of benzoic acid, the crosslinking cutting rate was calculated according to the following formula. The relative value of crosslinking cutting (the relative value of the cutting rate) was a value (%) of the crosslinking cutting rate at each concentration when the crosslinking cutting rate of PTB was set to 100. Here, Shimadzu Ultra High Performance Liquid Chromatography Nexera System (commercially available from Shimadzu Corporation) was used as a measurement device.

Crosslinking cutting rate (%)={(A−B)/C}×100

A: the amount of benzoic acid in the reaction solution
B: the amount of benzoic acid in the sample
C: the amount of PPD used in the reaction (the amount of the substrate)
(Crosslinking Cutting Test Results)
When the crosslinking cutting rate in the sample and the PTB solution (5 mmol/L) and the value of the crosslinking cutting rate (a relative value of the cutting rate) in the sample when PTB (5 mmol/L) was set as 100% were determined, the crosslinking cutting rate of the sample was 10.07, the crosslinking cutting rate of PTB was 22.4, and the relative value of the cutting rate of the sample was 44.87%. Therefore, the extract W exhibited the AGEs decomposition activity.

<Test f: Test for Anti-Type I Allergy Agent>
<Test f1: RBL-2H3 Cell Degranulation Inhibition Test Using Extract A>
[Preparation of Test Solution]
The extract A was dissolved in water to prepare 50 mg/mL of a test solution stock solution. The test solution stock solution was diluted with a buffer solution shown in the following Table 5 to prepare test solutions with a specimen concentration of 2,000, 1,000, and 500 µg/mL.
[Test Operation]
RBL-2H3 cells (National Institute of Biomedical Innovation, Health and Nutrition) as rat basophilic leukemia cells were seeded in a 96-well plate and then cultured overnight. A culture medium having a composition shown in Table 5 and further containing anti-DNP-IgE antibodies was added, and the mixture was reacted at 37° C. for 2 hours and the cells was then washed with a buffer solution. In addition, 2,000, 1,000, and 500 µg/mL of the prepared test solutions were added so that the final concentration was 1,000 µg/mL (Example f1), 500 µg/mL (Example f2) and 250 µg/mL (Example f3). Then, the reaction was performed at 37° C. for 10 minutes and a DNP-labeled human serum albumin was then added and the mixture was additionally reacted at 37° C. for 3 hours. In addition, the same test was performed on an untreated control in which no test solution was added and only a buffer solution was added (Comparative Example f1), and a positive control in which Wortmannin (commercially available from Wako Pure Chemical Corporation) was added to a final concentration of 25 nmol/L. In addition, after the culture medium containing no anti-DNP-IgE antibodies was added, the buffer solution and the DNP-labeled human serum albumin were sequentially added, and the mixture reacted in the same manner was used as an unstimulated antigen control.
After a total amount of the cell supernatant was collected into an empty well, a cell lysis buffer (Lysis buffer) was added to the cells, and the cells were left at room temperature for 10 minutes to obtain a cell dissolved solution. A p-nitrophenyl-2-acetamido-2-deoxy-β-D-glucoplanoside solution (hereinafter referred to as a substrate solution) was added to the cell supernatant and the cell dissolved solution, the mixture was reacted at 37° C. for 25 minutes, and a glycine buffer was then added to stop the reaction. In addition, a glycine buffer was added to the cell supernatant and the cell dissolved solution, the mixture was reacted at 37° C. for 25 minutes, and a substrate solution was then added to prepare a sample blank.

TABLE 5

| Materials | Composition |
| --- | --- |
| Culture medium | DMEM culture medium |
| | Fetal bovine serum (10 vol %, with respect to total amount of culture medium) |
| | Penicillin-streptomycin solution (1 vol %, with respect to total amount of culture medium) |
| Buffer solution (MT buffer, pH 7.3) | NaCl (137 mmol/L) |
| | KCl (2.7 mmol/L) |
| | $CaCl_2$ (1.8 mmol/L) |
| | $MgCl_2 \cdot 6H_2O$ (1 mmol/L) |
| | D(+)-glucose (5.6 mmol/L) |
| | HEPES Free acid (20 mmol/L) |
| | Albumin bovine F—V (1 g/L) |

[Calculation of Degranulation Rate]

For respective samples of Examples f1 to f3, Comparative Example f1, the positive control, the unstimulated antigen control and the sample blank, the absorbance of p-nitrophenol produced by the reaction of β-hexosaminidase present in granules with the substrate was measured (measurement wavelength: 405 nm, control wavelength: 650 nm) using a microplate reader (SpectraMax M2e, commercially available from Molecular Devices, LLC.).

The release rate was determined from the absorbance of each sample with respect to the absorbance of Comparative Example f1 according to the following formula, and additionally the degranulation rate was calculated from the release rate. Here, in the formula, "absorbance on cell supernatant side" and "absorbance on cell solution side" were values obtained by subtracting the sample blank.

Release rate (%)=absorbance on cell supernatant side/(absorbance on cell supernatant side+absorbance on cell solution side)

Degranulation rate (%)={average value of (release rate of test solution-release rate of unstimulated antigen control)/(release rate of untreated control-release rate of unstimulated antigen control)}×100

Figure 8:
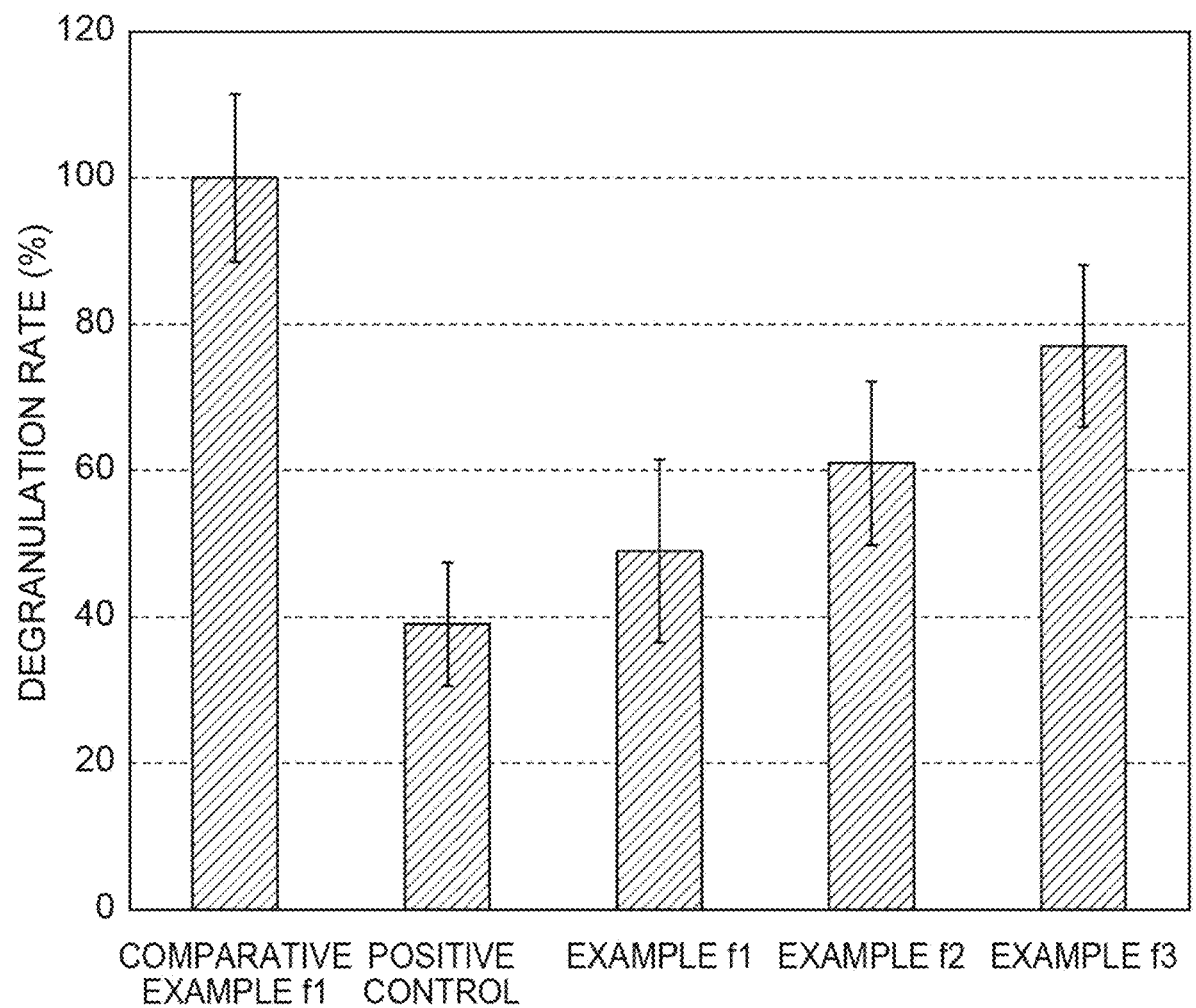
FIG. 8 is a graph showing degranulation rates of Examples f1 to f3, Comparative Example f1 and a positive control.

The calculation results of the degranulation rate are shown in FIG. 8. The degranulation rate was 100±11.5 for Comparative Example f1, 39±8.4 for the positive control, 49±12.5 for Example f1, 61±11.2 for Example f2, and 77±11.1 for Example f3.

<Test f2: RBL-2H3 Cell Degranulation Inhibition Test Using Extract W>

[Preparation of Test Solution]

The extract W was dissolved in ethanol to prepare 50 mg/mL of a test solution stock solution. The test solution stock solution was diluted with a buffer solution shown in the above Table 5 to prepare test solutions with a specimen concentration of 1,000, 500 and 250 μg/mL.

[RBL-2H3 cell degranulation inhibition test] The degranulation rate was calculated in the same method as in Test Example 1 except that the prepared test solution containing the extract W was used, during the test operation in the above Test Example f1, the test solution was added so that the final concentration of the test solution was 500 μg/mL (Example f4), 250 μg/mL (Example f5) and 125 μg/mL (Example f6). Comparative Example f1 was the same untreated control as in Test Example f1.

Figure 9:
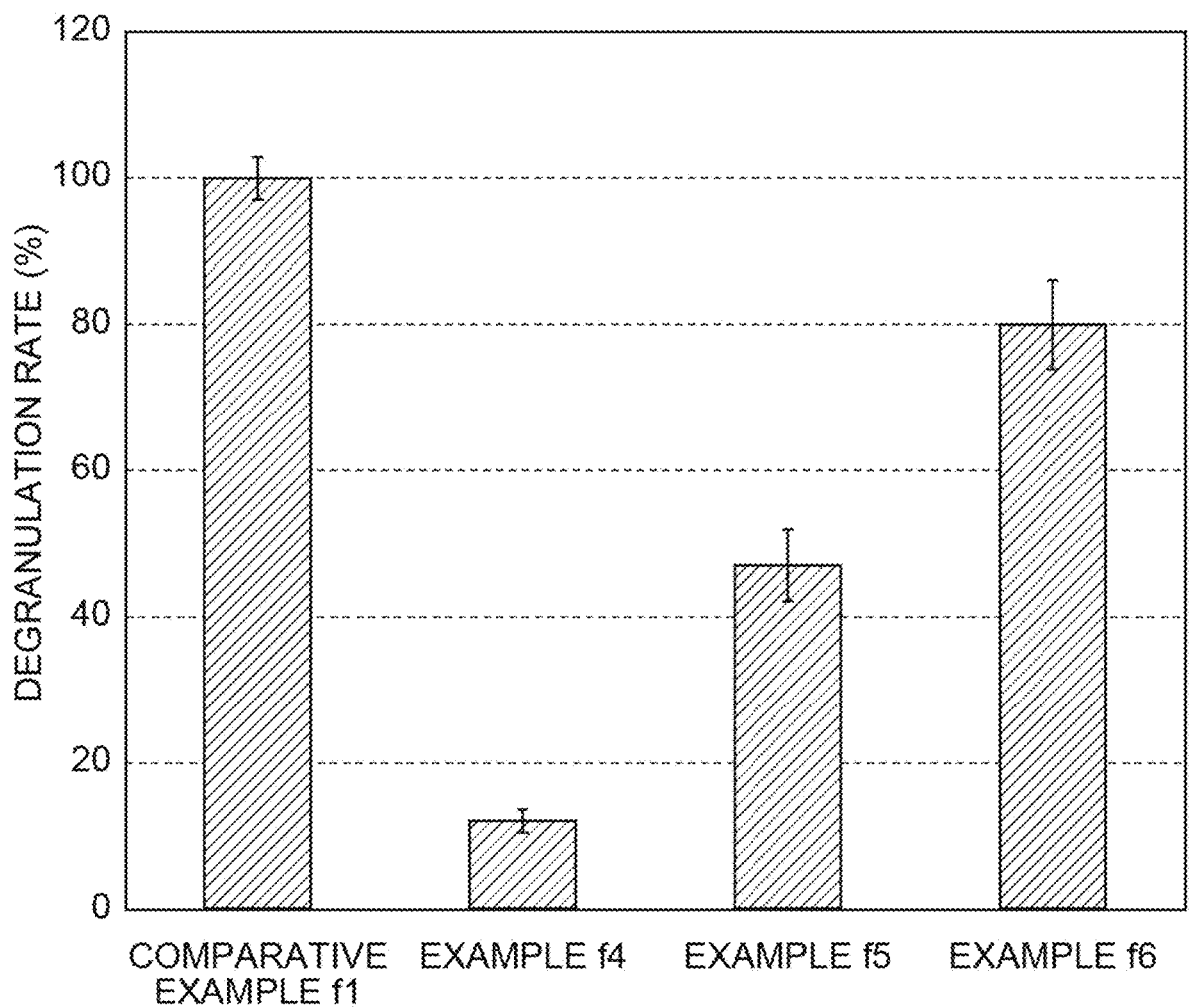
FIG. 9 is a graph showing degranulation rates of Examples f4 to f6 and Comparative Example f1.

The calculation results of the degranulation rate are shown in FIG. 9. The degranulation rate was 100±2.9 for Comparative Example f1, 12±1.6 for Example f4, 47±4.9 for Example f5, and 80±6.1 for Example f6.

<Test g: Test for Antihypertensive Agent>
<Angiotensin Converting Enzyme Inhibition Test>

The angiotensin converting enzyme inhibition test was performed based on the method of Nakano et al. (Nakano et al, Biosci. Biotechnol. Biochem., 70, 1118-1126 (2006)).

1.0 g of each of the extract A and the extract W was extracted in 20 mL of a 50% (V/V) ethanol solution and then appropriately diluted with a 0.1 mol/L Hepes buffer solution (pH 8.3) to prepare a test solution with a concentration shown in Table 6. 25 μL each of a 0.1 mol/L Hepes buffer solution (untreated group) or test solution was added to a 96-well microplate, and additionally, 25 μL of a 20 mU/mL ACE solution was added and the mixture was incubated at 37° C. for 5 minutes. Here, 25 μL of an 8 mmol/L substrate (hippuryl-L-histidine-L-leucine; Hip-His-Leu) solution was additionally added and the mixture was reacted at 37° C. for 30 minutes. Then, 25 μL of a 0.1 mol/L sodium hydroxide aqueous solution was added to stop the reaction, 25 μL of a 1 mass % phthalaldehyde (OPA) aqueous solution was additionally added, and the mixture was left for 20 minutes. Then, 25 μL of a 0.1 mol/L hydrochloric acid was added to prepare a measurement specimen. The measurement specimen was left at room temperature for 10 minutes and the fluorescence intensity was measured using a microplate reader according to the following conditions. Here, a phosphate buffered saline was used in place of the ACE solution for the blank.

(Microplate Reader Operation Conditions)

Model: SpectraMax M2e (commercially available from Molecular Devices, LLC.)

Measurement conditions: fluorescence, endpoint mode, bottom lead

Excitation wavelength: 355 nm

Fluorescence wavelength: 460 nm

The fluorescence intensity of each test solution when the fluorescence intensity of the untreated group was set as 100% was evaluated as the ACE inhibition rate. The results are shown in Table 6.

TABLE 6

|  | Concentration of extract A (with respect to total amount of test solution, mg/mL) | ACE inhibition rate (%) |
| --- | --- | --- |
| Extract A | 0.4 | 25 |
|  | 0.8 | 43 |
|  | 1.0 | 51 |
|  | 2.0 | 74 |
|  | 3.0 | 85 |
| Extract W | 0.3 | 33 |
|  | 0.4 | 41 |
|  | 0.5 | 48 |
|  | 0.6 | 55 |
|  | 0.7 | 60 |

As shown in Table 6, in the extract A and the extract W, the ACE inhibitory effect was observed. $IC_{50}$ of the extract A was 0.95 mg/mL with respect to a total amount of the test solution (final concentration with respect to a total amount of the measurement specimen: 0.16 mg/mL) and $IC_{50}$ of the extract W was 0.52 mg/mL with respect to a total amount of the test solution (final concentration with respect to a total amount of the measurement specimen: 0.087 mg/mL).

<Test h: Test for Flavor Improving Agent>

Test Example h1: Flavor Improving Test Using Extract A

[Soy Milk]

0.6 g (Example h1-1) or 0.3 g (Example h1-2) of the solution containing the extract A (with a solid content concentration of 0.3%) was added to 100 g of soy milk (product name: Otsuka Amazing Soy Unadjusted, commercially available from Otsuka Foods Co., Ltd.) so that the extract A had a concentration shown in Table 7 to prepare test products (Examples h1-1 and h1-2).

[Vinegar-Containing Beverage]

1.7 g of the solution containing the extract A (with a solid content concentration of 0.3%) was added to a vinegar-containing beverage containing 50 g of rice vinegar, 200 g of water, and 15 g of granulated sugar to prepare a test product (Example h1-3).

[Processed Beef Product (Meat Ball)]

30 g of beef and 0.012 g of the solution containing the extract A (with a solid content concentration of 0.3%) were mixed while mincing the beef with a food processor. 10 g of each of the minced meat was divided in aluminum cups and baked in an oven at 200° C. for 5 minutes, and turned upside down, and additionally baked for 5 minutes. The product cooled to about the temperature of human skin after baking was used as a test product (Example h1-4).

[Processed Chicken Product (Chicken Ball)]

25 g of minced chicken breast, 10 g of soy proteins hydrated with water (product name: New soy milk S 20F, commercially available from The Nisshin OilliO Group, Ltd.), and 0.1 g of the solution containing the extract A (with a solid content concentration of 0.3%) were mixed. The mixture was rolled into bite-sized pieces and heated with boiling water for 5 minutes to prepare chicken balls and these were used as test products (Example h1-5).

[Sensory Evaluation]

The foods and drinks of the examples were subjected to sensory evaluation for items shown in Table 7 to Table 10. Here, for evaluation criteria for the sensory evaluation, relative evaluation compared with the control product (those containing no extract A) was performed, and each example was evaluated with a numerical value from −2 points to 2 points based on 0 points for the control product. For each evaluation item, −2 points indicate that "strong flavor was not felt as compared with the control product" and 2 points indicate that "strong flavor was felt as compared with the control product." The average values of the evaluation points are shown in Table 7 to Table 10. Here, "solid content concentration" in the tables indicates the solid content concentration of the extract A with respect to a total amount of the test product, and the same applies hereinafter unless otherwise specified.

TABLE 7

| | | | Average value of evaluation points (11 panelists (Example h1-1) and 10 panelists (Example h1-2) | | | | | |
|---|---|---|---|---|---|---|---|---|
| | | Solid content | Preferred flavor | | | Unpleasant flavor | | |
| | Food | concentration (ppm by mass) | Pure taste | Delicious taste | Refreshing taste | Ease of drinking | Green smells of beans | Unpleasant aftertaste | Astringent taste/ miscellaneous taste |
| Example h1-1 | Soy milk | 18 | 0.93 | 0.65 | 1.13 | 1.15 | −1.06 | −0.85 | −0.79 |
| Example h1-2 | | 9 | 1.12 | 0.94 | 1.08 | 1.26 | −1.05 | −1.13 | −1.02 |

TABLE 8

| | | | Average value of evaluation points (12 panelists) | | | | | | |
|---|---|---|---|---|---|---|---|---|---|
| | | Solid content | Preferred flavor | | | | | Unpleasant flavor | |
| | Food | concentration (ppm by mass) | Ease of drinking | Delicious taste | Refreshing taste | Mellow-ness | Smooth-ness | Sour-ness | Unpleasant aftertaste |
| Example h1-3 | Vinegar-containing beverage | 20.4 | 0.83 | 0.60 | 0.47 | 1.09 | 1.10 | −0.50 | −0.45 |

TABLE 9

| | | | Average value of evaluation points (13 panelists) | | | | | |
|---|---|---|---|---|---|---|---|---|
| | | Solid content | Preferred flavor | | | Unpleasant flavor | | |
| | Food | concentration (ppm by mass) | Delicious taste | Ease of eating | Refreshing taste | Unpleasant aftertaste | Meat smell | Oily taste |
| Example h1-4 | Meat ball | 1.2 | 0.83 | 0.97 | 0.78 | −1.01 | −1.01 | −0.62 |

TABLE 10

| | | | Average value of evaluation points (11 panelists) | | | | | | |
|---|---|---|---|---|---|---|---|---|---|
| | | Solid content | Preferred flavor | | | | Unpleasant flavor | | |
| | Food | concentration (ppm by mass) | Delicious taste | Refreshing taste | Ease of eating | Original flavor of chicken | Green smells of beans | Unpleasant aftertaste | Astringent taste/ miscellaneous taste |
| Example h1-5 | Chicken ball | 5 | 0.88 | 0.93 | 0.98 | 0.27 | −0.82 | −1.07 | −0.78 |

Test Example h2: Flavor Improving Test Using Extract W

[Soy Milk, Vinegar-Containing Beverage, Processed Beef Product (Meat Ball)]

Test products (Examples h2-1 to h2-3) were prepared in the same manner as in Test Example h1 except that, in Test Example h1, the extract W was used in place of the extract A.

[Processed Seafood (Grilled Mackerel)]

An immersion liquid in which 4.175 g of the solution containing the extract W (with a solid content concentration of 0.3%) was added to 500 g of 8% saline was prepared. After thawing frozen mackerel fillets, the skin was cut and the fillets were then immersed in the immersion liquid for 10 minutes. The mackerel was cooked on a grill for 7 minutes on each side to prepare a test product (Example h2-4). The test product that was frozen once was heated in a microwave oven and then subjected to sensory evaluation.

[Lactic Acid Bacteria Beverage]

A lactic acid bacteria beverage containing 100 parts by mass of a commercial beverage (product name: MilMil, commercially available from Yakult Honsha Co., Ltd.), 0.275 parts by mass of 10% acetic acid, 0.007 parts by mass of aspartame (commercially available from Ajinomoto Co., Inc.) and 0.015 parts by mass of a solution containing 1% of 0-carotene (commercially available from Mitsubishi-Chemical Foods Corporation) was prepared. 0.075 g of the solution containing the extract W (with a solid content concentration of 0.3%) was added to 100 g of the lactic acid bacteria beverage to prepare a test product (Example h2-5).

Sensory evaluation was performed for items in the same method as in Test Example h1. The results are shown in Table 11 to Table 15. Here, in Table 11, the solid content concentration in the tables indicates the solid content concentration of the extract W with respect to a total amount of the immersion liquid.

TABLE 11

| | | | Average value of evaluation points (13 panelists) | | | | | |
| --- | --- | --- | --- | --- | --- | --- | --- | --- |
| | | | | | | | Unpleasant flavor | |
| | | Solid content | Preferred flavor | | | Green | | |
| | Food | concentration (ppm by mass) | Pure taste | Delicious taste | Refreshing taste | Ease of drinking | smells of beans | Unpleasant aftertaste | Astringent taste/ miscellaneous taste |
| Example h2-1 | Soy milk | 18 | 0.94 | 0.46 | 0.80 | 0.65 | −0.37 | −0.49 | −0.48 |

TABLE 12

| | | | Average value of evaluation points (13 panelists) | | | | | | |
| --- | --- | --- | --- | --- | --- | --- | --- | --- | --- |
| | | Solid content | Preferred flavor | | | | | Unpleasant flavor | |
| | Food | concentration (ppm by mass) | Ease of drinking | Delicious taste | Refreshing taste | Mellow-ness | Smooth-ness | Sour-ness | Unpleasant aftertaste |
| Example h2-2 | Vinegar-containing beverage | 20.4 | 0.92 | 0.76 | 0.35 | 0.94 | 1.08 | −0.85 | −0.67 |

TABLE 13

| | | | Average value of evaluation points (14 panelists) | | | | | |
| --- | --- | --- | --- | --- | --- | --- | --- | --- |
| | | Solid content | Preferred flavor | | | Unpleasant flavor | | |
| | Food | concentration (ppm by mass) | Delicious taste | Ease of eating | Refreshing taste | Unpleasant aftertaste | Meat smell | Oily taste |
| Example h2-3 | Meat ball | 1.2 | 0.51 | 0.66 | 0.91 | −0.75 | −0.97 | −0.44 |

TABLE 14

| | | | Average value of evaluation points (14 panelists) | | | | | |
| --- | --- | --- | --- | --- | --- | --- | --- | --- |
| | | Solid content | Preferred flavor | | | Unpleasant flavor | | |
| | Food | concentration (ppm by mass) | Delicious taste | Ease of eating | Refreshing taste | Unpleasant aftertaste | Fish odor | Oily taste |
| Example h2-4 | Grilled mackerel | 25 | 0.69 | 1.00 | 0.74 | −0.83 | −0.93 | −0.62 |

TABLE 15

| | Food | Solid content concentration (ppm by mass) | Average value of evaluation points (13 panelists) Preferred flavor | | | | |
|---|---|---|---|---|---|---|---|
| | | | Refreshing taste | Pure taste | Ease of drinking | Delicious taste | Elimination of aftertaste |
| Example h2-5 | Lactic acid bacteria beverage | 2.3 | 0.98 | 1.03 | 0.88 | 0.60 | 0.95 |

Test Example h3: Comparison Test with Sugar Cane-Derived Extract

[Production of Sugar Cane-Derived Extract]

Figure 10:
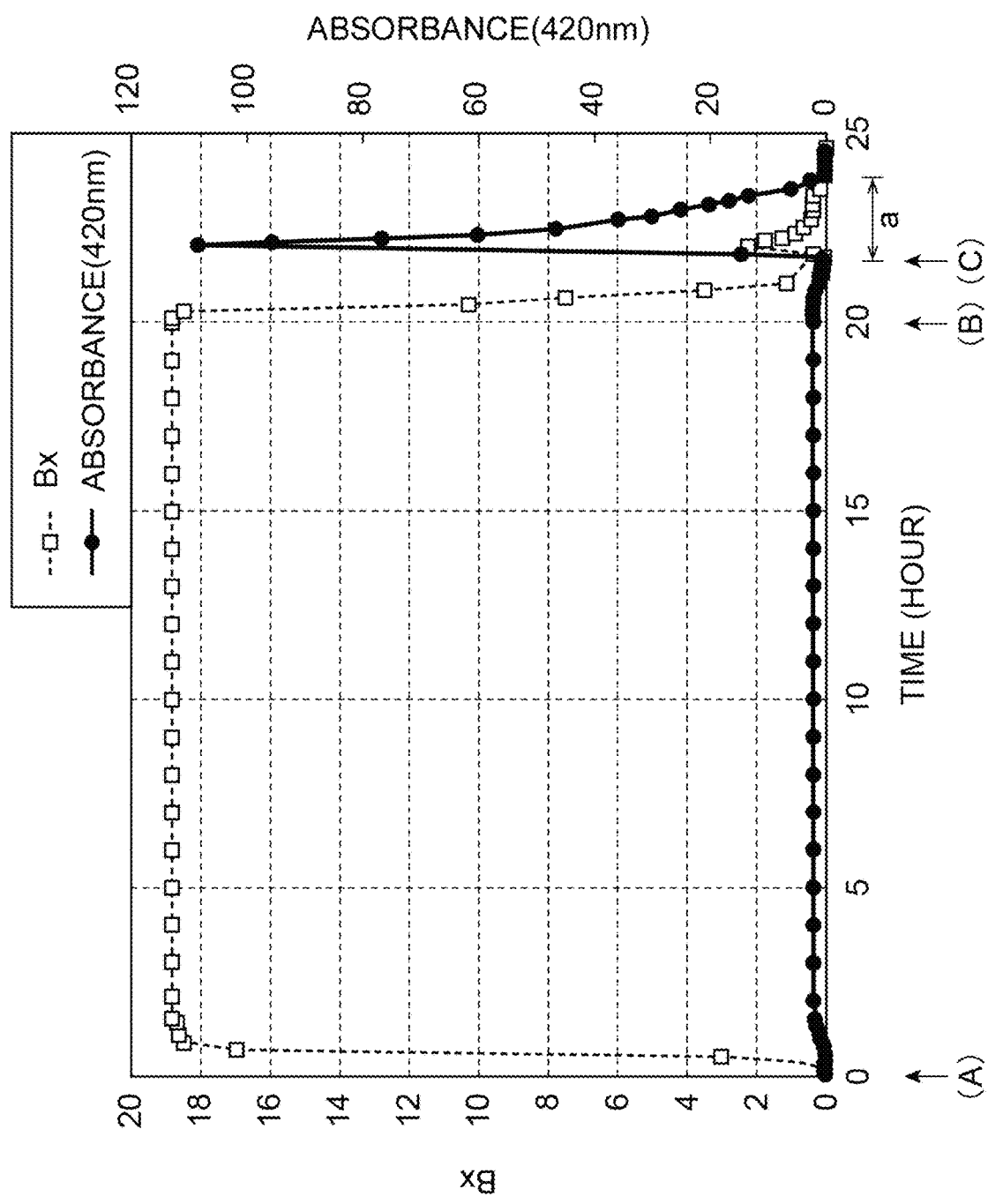
FIG. 10 is a graph showing a dissolution pattern in a sugar cane-derived extract in a test h.

7,500 L of a sugar cane juice (clean juice after lime cleaning obtained in the sugar producing process in the raw sugar production factory, Made in Okinawa, solid content 14%) as a raw material was filtered with a cartridge filter (cotton wind cartridge filter, model TCW-10-CSD commercially available from Advantec Co., Ltd.) to obtain a clean juice filtered product. 500 L of a synthetic adsorbing agent (SP-207 commercially available from Mitsubishi Chemical Corporation) was filled into a resin column (with an inner diameter of 800 mm and a height of 2,000 mm), and the above clean juice filtered product was caused to pass therethrough at a flow rate of 2,500 L/hour (SV=5.0 (hour$^{-1}$)). FIG. 10 shows the dissolution pattern. In FIG. 1, (A) indicates a liquid passing start point. Here, during passing of the clean juice, water at 80° C. was constantly circulated in the water jacket.

Next, 1,200 L of tap water was caused to pass through the resin column at a flow rate of 2,500 L/hour (SV=5.0 (hour$^{-1}$)) for washing. In FIG. 10, (B) indicates a liquid passing start point. After washing with tap water, when a fraction eluted from the resin column was subjected to column detection, it was confirmed that Bx was about 0 in the Refractometer Brix (Bx) meter (model PAL-J, commercially available from Atago Co., Ltd.). Then, 1,500 L of tap water was caused to pass under the resin column at a flow rate of 4,500 L/hour (SV=9.0 (hour$^{-1}$)) and backwashing was performed.

Next, 1,000 L of a 55% ethanol aqueous solution (ethanol/water=55/45 (volume/volume)) as an elution solvent was caused to pass through the resin column at a flow rate of 1,000 L/hour (SV=2.0 (hour$^{-1}$)). In FIG. 10, (C) indicates a liquid passing start point. Subsequently, 760 L of tap water was caused to pass through the resin column at a flow rate of 1,000 L/hr (SV=2.0 (hour$^{-1}$)) to elute components adsorbed on the synthetic adsorbing agent. Here, the 55% ethanol aqueous solution and tap water were heated to 50° C. with a plate heat exchanger (model RX-025A-KNHJR-36 commercially available from Hitachi, Ltd.) and caused to pass through the resin column.

1,460 L in the latter half (the part a in FIG. 10) of the fraction eluted from the resin column was concentrated under a reduced pressure to a concentration of about 50 times with a centrifugal thin film vacuum evaporating device (evaporator, CEP-5S commercially available from Okawara MFG. Co., Ltd.), and then freeze-dried overnight to obtain 8.4 kg of brown powder (I). This powder was dissolved in ethanol and water to prepare a sugar cane-derived extract with a solid content concentration of 30 mass % (hereinafter referred to as a "sugar cane extract").

[Soy Milk, Vinegar-Containing Beverage, Processed Beef Product (Meat Ball), Processed Seafood (Grilled Mackerel), and Lactic Acid Bacteria Beverage]

The control product was prepared using the above sugar cane extract diluted solution (with a solid content concentration of 0.3%) according to the method described in Table 16. On the other hand, in Examples h3-1 to h3-4, and Examples h3-7 to h3-8 (soy milk, vinegar-containing beverage and grilled mackerel), test products were prepared in the same method as in Test Example h1 or Test Example h2. In Examples h3-5 to h3-6 and Examples h3-9 to h3-10 (meat ball and lactic acid bacteria beverage), test products were prepared using the solution containing the extract A or the solution containing the extract W (with a solid content concentration 0.3%) in place of the sugar cane extract diluted solution according to the control product preparation method described in Table 16.

TABLE 16

| Control product | Preparation method |
|---|---|
| Soy milk | Prepared in the same method as in Test Example h1 except that 0.3 g of a sugar cane extract diluted solution was added to 100 g of the above soy milk. |
| Vinegar-containing beverage | Prepared in the same method as in Test Example h1 except that 0.85 g of a sugar cane extract diluted solution was added to 132.5 g of the above vinegar-containing beverage. |
| Meat ball | Prepared in the same method as in Test Example h1 except that 0.14 g of a sugar cane extract diluted solution was added to 225 g of the above minced meat. |
| Grilled mackerel | Prepared in the same method as in Test Example h2 except that a solution in which 4.17 g of a sugar cane extract diluted solution was added to 500 g of 8% saline was used as an immersion liquid. |
| Lactic acid bacteria beverage | Prepared in the same method as in Test Example h2 except that 0.15 g of a sugar cane extract diluted solution was added to 100 g of the above lactic acid bacteria beverage. |

Sensory evaluation was performed for items according to the same method as in Test Example h1. Each example was evaluated with a numerical value from −2 points to 2 points based on 0 points for the control product (food and drink containing the sugar cane extract), and. The results are shown in Table 17 to Table 21.

TABLE 17

| | | | Average value of evaluation points (14 panelists (Example h3-1) and 13 panelists (Example h3-2) | | | | | | |
|---|---|---|---|---|---|---|---|---|---|
| | | Solid content | Preferred flavor | | | | Unpleasant flavor | | |
| | Decomposition extract | Food | concentration (ppm by mass) | Pure taste | Delicious taste | Refreshing taste | Ease of drinking | Green smells of beans | Unpleasant aftertaste | Astringent taste/ miscellaneous taste |
| Example h3-1 | Extract A | Soy milk | 9 | 0.56 | 0.61 | 0.81 | 0.86 | −0.67 | −0.67 | −0.76 |
| Example h3-2 | Extract W | | | 0.69 | 0.51 | 0.83 | 0.65 | −0.69 | −0.63 | −0.67 |

TABLE 18

| | | | Average value of evaluation points (13 panelists (Example h3-3) and 11 panelists (Example h3-4)) | | | | | | |
|---|---|---|---|---|---|---|---|---|---|
| | | Solid content | Preferred flavor | | | | | Unpleasant flavor | |
| | Decomposition extract | Food | concentration (ppm by mass) | Ease of drinking | Delicious taste | Refreshing taste | Mellow- ness | Smooth- ness | Sour- ness | Unpleasant aftertaste |
| Example h3-3 | Extract A | Vinegar- containing beverage | 20.4 | 0.89 | 0.82 | 0.46 | 1.03 | 0.92 | −0.61 | −0.66 |
| Example h3-4 | Extract W | | | 1.03 | 0.98 | 0.35 | 1.20 | 1.29 | −0.66 | −0.74 |

TABLE 19

| | | | Average value of evaluation points (13 panelists) | | | | | | |
|---|---|---|---|---|---|---|---|---|---|
| | | | Preferred flavor | | | | Unpleasant flavor | | |
| | | Solid content | | | | Original | | | |
| | Decomposition extract | Food | concentration (ppm by mass) | Delicious taste | Ease of eating | Refreshing taste | flavor of beef | Unpleasant aftertaste | Meat smell | Oily taste |
| Example h3-5 | Extract A | Meat ball | 1.9 | 0.34 | 0.51 | 0.56 | 0.24 | −0.59 | −0.89 | −0.63 |
| Example h3-6 | Extract W | | | 0.80 | 0.84 | 0.70 | 0.47 | −0.71 | −0.83 | −0.34 |

TABLE 20

| | | | Average value of evaluation points (12 panelists) | | | | | | |
|---|---|---|---|---|---|---|---|---|---|
| | | | Preferred flavor | | | | Unpleasant flavor | | |
| | | Solid content | | | | Original | | | |
| | Decomposition extract | Food | concentration (ppm by mass) | Delicious taste | Ease of eating | Refreshing taste | flavor of fish | Unpleasant aftertaste | Fish odor | Oily taste |
| Example h3-7 | Extract A | Grilled mackerel | 25 | 0.85 | 0.98 | 0.75 | 0.20 | −0.87 | −1.07 | −0.55 |
| Example h3-8 | Extract W | | | 0.80 | 0.90 | 0.77 | 0.20 | −0.77 | −0.93 | −0.62 |

TABLE 21

| | Decomposition extract | Food | Solid content concentration (ppm by mass) | Average value of evaluation points (13 panelists) | | | | | |
|---|---|---|---|---|---|---|---|---|---|
| | | | | Preferred flavor | | | | | Unpleasant flavor |
| | | | | Refreshing taste | Pure taste | Ease of drinking | Delicious taste | Elimination of aftertaste | Offensive taste |
| Example h3-9 | Extract A | Lactic acid bacteria beverage | 4.5 | 0.60 | 0.55 | 0.58 | 0.62 | 0.89 | −0.34 |
| Example h3-10 | Extract W | | | 0.69 | 0.83 | 0.60 | 0.55 | 0.75 | −0.23 |

Test Example h4: Evaluation Using Taste Recognition Device

The above extract A and the sugar cane extract were added to a 0.2% acetic acid aqueous solution to prepare 0.2% acetic acid aqueous solutions with a final solid content concentration of 45 ppm by mass, 90 ppm by mass, and 180 ppm by mass (Examples h4-1 to h4-3, and Comparative Examples h4-1 to h4-3). The acidity of the acetic acid solution was measured using a taste recognition device (TS-5000Z, commercially available from Intelligent Sensor Technology, Inc.). During measurement using the taste recognition device, measurement was performed using a first taste (relative value) of the acidity sensor (CA0). Table 22 shows the relative values of the acidity of the acetic acid aqueous solutions when the acidity of the acetic acid aqueous solution (control) to which the extract A and the sugar cane extract were not added was set to 0. A relative value of the acidity of 0 or less indicates that unpleasant flavors (sourness) felt from acetic acid were reduced as compared with the 0.2% acetic acid aqueous solution as a control.

TABLE 22

| | Extract | Final solid content concentration (ppm by mass) | pH | Acidity |
|---|---|---|---|---|
| Control | — | 0 | 3.093 | 0 |
| Example h4-1 | Extract A | 45 | 3.124 | −0.67 |
| Example h4-2 | | 90 | 3.153 | −1.33 |
| Example h4-3 | | 180 | 3.224 | −2.83 |
| Comparative Example h4-1 | Sugar cane extract | 45 | 3.109 | −0.51 |
| Comparative Example h4-2 | | 90 | 3.135 | −1.03 |
| Comparative Example h4-3 | | 180 | 3.184 | −1.96 |

<Test i: Test for Muscle Enhancing Agent>
[Materials]
In the following test examples, the following materials were used.
(Cells)
Mouse myoblasts C2C12 cells (ATCC, CRL-1772)
(Culture Mediums)
Growth culture medium composition: DMEM culture medium, 10% FBS, antibiotics added
Differentiation culture medium composition: DMEM culture medium, 0.5% FBS, antibiotics added
(Test Reagents)
Dulbecco modified Eagle's culture medium (DMEM culture medium, commercially available from Nacalai Tesque, Inc.)
Fetal Bovine Serum (FBS) (commercially available from Cell CultureBioscience)
Penicillin-streptomycin mixed solution (commercially available from Nacalai Tesque, Inc.) 0.25% trypsin/EDTA mixed solution (commercially available from Nacalai Tesque, Inc.)
Dulbecco PBS (−) (commercially available from Nissui Pharmaceutical Co., Ltd.)
Gelatin (A type, commercially available from MP Biomedicals)
Hoechst (nuclear staining reagent, Hoechst 33342 solution, commercially available from Dojindo Molecular Technologies, Inc.)
MitoTracker (MitoTracker Mitochondrion-Selective Probes, commercially available from Invitrogen)
Rhodamine (VectaCell Rhodamine 123, commercially available from Funakoshi)
4%-paraformaldehyde/phosphate buffer solution (commercially available from Nacalai Tesque, Inc.)
Primary antibodies (Anti-Myosin Heavy Chain Purified clone: MF20, commercially available from eBioscience)
Secondary antibodies (Alexa Fluor 555 F(ab)2 fragment of goat anti-mouse IgG (H+L), commercially available from Life Technologies Japan)
[Cell Pre-Culture]
Cells used in the following test examples were pre-cultured.
C2C12 cells were cultivated using a growth culture medium in a T-75 flask (75 cm$^2$ U-shaped canted neck cell culture flask, commercially available from Corning Co., Ltd.). The T-75 flask was put into a $CO_2$ incubator (5% $CO_2$, 37° C., wet) and the C2C12 cells were cultured. The culture medium was replaced every other day, and when an 80% confluence was reached, the cells were collected and used for the test. Here, in the following test, regarding a well plate for culturing C2C12 cells, a plate coated with gelatin according to the following coating method was used.
(1) A 0.75% gelatin aqueous solution was sterilized in an autoclave.
(2) 100 μL of the 0.75% gelatin aqueous solution was added to each well in the plate, and the wells were left in a $CO_2$ incubator (5% $CO_2$, 37° C.) for 2 hours.
(3) The 0.75% gelatin aqueous solution was removed, and the obtained plate was used.

Test Example i1-1: Mitochondrial Activation Test (Evaluation of Activity Per Cell)

Pre-cultured cells were seeded in a 96-well plate for fluorescence observation (optical bottom plate, commercially available from Nunc) at 4×10$^4$ cells/0.1 mL/well using a growth culture medium. The well plate was cultured in a $CO_2$ incubator (5% $CO_2$, 37° C.) for 2 days. Then, the culture medium was replaced with a differentiation culture medium and culturing was performed for 4 days to form myotube cells. After the myotube cells were formed, the culture medium was replaced with a differentiation culture medium containing the extract A (Examples i1-1 to i1-3), a differentiation culture medium containing the extract W and 1% (v/v) ethanol (Examples i1-4 to i1-6), a differentiation culture medium containing no extract (Comparative Example i1-1), a differentiation culture medium containing no extract but containing 1% (v/v) ethanol (Comparative Example i1-2), or a differentiation culture medium containing resveratrol with a concentration of 50 µM and 1% (v/v) ethanol (Positive Control i1-1), and culturing was performed. The culturing ended 48 hours after the culturing started. The results were used as test samples of Examples i1-1 to i1-6, Comparative Examples i1-1 to i1-2, or Positive Control i1-1. Here, Table 23 shows the final concentrations of the bagasse decomposition extracts in the differentiation culture mediums in Examples i1-1 to i1-6.

After the culture supernatant was removed, a differentiation culture medium containing 5 µg/mL Hoechst (reagent for nuclear staining) or 10 µg/mL rhodamine (mitochondrial activity staining reagent) was added to the well plate, and culturing was performed at 37° C. for 30 minutes. Then, the fluorescence intensity was measured with a fluorescent plate reader. The mitochondrial activity per cell was calculated by dividing the fluorescence intensity of the differentiation culture medium containing rhodamine by the fluorescence intensity of the differentiation culture medium containing Hoechst. The relative values (%) in the test samples of Examples i1-1 to i1-3 when the mitochondrial activity in the test sample of Comparative Example i1-1 was set as 100% were determined. In addition, the relative values (%) in the test samples of Examples i1-4 to i1-6 and Positive Control i1 when the mitochondrial activity in the test sample of Comparative Example i1-2 was set as 100% were determined. The test was performed 5 times for each sample, and the average values are shown in Table 23.

As shown in Table 23, compared with the test sample of Comparative Example i1-1 or i1-2 to which no bagasse decomposition extract was added, the mitochondrial activity per cell increased in the test samples of Examples i1-1 to i1-6 to which the extract was added. Since the mitochondrial activity also increased in Positive Control i1-1, it can be said that the test was performed without any problem.

TABLE 23

| Added | Extract solution in culture medium | | Mitochondrial activity per cell |
|---|---|---|---|
| solvent in culture medium | Type | Concentration (µg/mL) | (relative value, %) (average value ± standard deviation) |
| Comparative Example i1-1 | — | — | 100.0 ± 1.6 |
| Example i1-1 | Extract A | 1 | 106.3 ± 0.6 |
| Example i1-2 | | 10 | 113.1 ± 1.2 |
| Example i1-3 | | 100 | 118.1 ± 0.8 |
| Comparative Example i1-2 | 1% (v/v) ethanol | — | — | 100.0 ± 1.2 |
| Example i1-4 | | Extract W | 1 | 103.6 ± 1.4 |
| Example i1-5 | | | 10 | 105.7 ± 1.4 |
| Example i1-6 | | | 100 | 120.6 ± 1.5 |
| Positive Control i1-1 | | — | — | 178.4 ± 9.6 |

Regarding the test samples of Example i1-5 and Example i1-6, the mitochondrial activity in the test sample after culturing for 72 hours was also evaluated according to the same method as above. When the mitochondrial activity in the test sample of Comparative Example i1-2 after culturing for 72 hours was set as 100% (100.0±1.6%), the mitochondrial activity in the test sample of Example i1-5 was 101.7±1.3% and the mitochondrial activity in the test sample of Example i1-6 was 115.0±2.4%. Here, compared with the test sample of Comparative Example i1-2 to which no bagasse decomposition extract was added, in the test samples of Example i1-5 and Example i1-6 to which the extract was added, the mitochondrial activity per cell also increased after culturing for 72 hours.

Test Example i1-2: Mitochondrial Activation Test (Evaluation of Amount of Mitochondria Per Cell)

Myotube cells were cultured in the same method as in Test Example i1-1. They were used as test samples of Examples i1-7 to i1-11, Comparative Examples i1-3 to i1-4, or Positive Control i1-2. Here, Table 24 shows the final concentrations of the bagasse decomposition extracts in the differentiation culture medium in Examples i1-7 to i1-11. Then, after the culture supernatant was removed, a differentiation culture medium containing 5 µg/mL Hoechst (reagent for nuclear staining) and 500 nM MitoTracker (mitochondria staining reagent) was added to the well plate, and the fluorescence intensity was measured by the same method as in Test Example i1-1. The amount of mitochondria per cell was calculated by dividing the fluorescence intensity of the differentiation culture medium containing MitoTracker by the fluorescence intensity of the differentiation culture medium containing Hoechst. The relative values (%) in the test samples of Examples i1-7 to i1-8 when the amount of mitochondria in the test sample of Comparative Example i1-3 was set as 100% were determined. In addition, the relative values (%) in the test samples of Examples i1-9 to i1-11 and Positive Control i1-2 when the mitochondrial activity in the test sample of Comparative Example i1-4 was set as 100% were determined. The test was performed 5 times for each sample, and the average values are shown in Table 24.

As shown in Table 24, compared with the test sample of Comparative Example i1-3 or i1-4 to which no bagasse decomposition extract was added, in the test samples of Examples i1-7 to i1-11 to which the extract was added, the amount of mitochondria per cell increased. Since the amount of mitochondria also increased in Positive Control i1-2, it can be said that the test was performed without any problem.

TABLE 24

| Added | Extract solution in culture medium | | Mitochondrial activity per cell |
|---|---|---|---|
| solvent in culture medium | Type | Concentration (µg/mL) | (relative value, %) (average value ± standard deviation) |
| Comparative Example i1-3 | — | — | — | 100.0 ± 2.6 |
| Example i1-7 | | Extract A | 10 | 102.4 ± 2.2 |
| Example i1-8 | | | 100 | 110.9 ± 2.4 |
| Comparative Example i1-4 | 1% (v/v) ethanol | — | — | 100.0 ± 1.2 |
| Example i1-9 | | Extract W | 1 | 102.0 ± 1.2 |
| Example i1-10 | | | 10 | 106.1 ± 1.7 |
| Example i1-11 | | | 100 | 115.9 ± 0.8 |
| Positive Control i1-2 | | — | — | 178.4 ± 9.6 |

Regarding the test samples of Example i1-8 and Example i1-11, the amount of mitochondria in the test sample after culturing for 72 hours was also evaluated according to the same method as above. When the amount of mitochondria in the test sample of Comparative Example i1-3 after culturing for 72 hours was set as 100% (100.0±3.4%), the amount of mitochondria in the test sample of Example i1-8 was 104.9±4.5%. In addition, when the amount of mitochondria in the test sample of Comparative Example i1-4 was set as 100% (100.0±0.8%), the amount of mitochondria in the test sample of Example i1-11 was 107.9±1.9%. Here, compared with the test sample of Comparative Example i1-3 or Comparative Example i1-4 to which no bagasse decomposition extract was added, in the test samples of Examples i1-8 and i1-11 to which the extract was added, the amount of mitochondria per cell also increased after culturing for 72 hours.

Test Example i2: Myotube Cell Differentiation Promote Test

Pre-cultured cells were seeded in a 96-well plate for fluorescence observation at 4×10$^4$ cells/0.1 mL/well using a growth culture medium. The well plate was cultured in a $CO_2$ incubator (5% $CO_2$, 37° C.) for 2 days. Then, the culture medium was replaced with a differentiation culture medium containing the extract A (Examples i2-1 to i2-2), a differentiation culture medium containing no extract (Comparative Example i2-1), a differentiation culture medium containing no extract but containing 0.1% (v/v) DMSO (Comparative Example i2-2), or a differentiation culture medium containing 0.5 μM LDN-193189 (4-(6-(4-(piperazine-1-yl)phenyl)pyrazolo [1,5-a] pyrimidin-3-yl)quinoline) and 0.1% (v/v) DMSO (Positive Control i2). After the culture medium was replaced, culturing was performed for 3 days, and after fixing, immunostaining with anti-myosin heavy chain (MHC) antibodies was performed. Here, Table 25 shows the final concentrations of the bagasse decomposition extracts in the differentiation culture mediums in Examples i2-1 to i2-2.

A 4%-paraformaldehyde/phosphate buffer solution was added at 100 μL/well to the cells after the culturing was completed, and the cells were left at 4° C. for 15 minutes. After being left, washing with Dulbecco PBS (DPBS) was performed three times, and a blocking treatment was then performed with DPBS containing 0.1% triton-X and 3% bovine serum albumin (BSA) at room temperature for 1 hour. Then, a 3% BSA/DBPS mixed solution containing primary antibodies (anti-myosin heavy chain antibodies: diluted 300-fold) was added, and the mixture was reacted at 4° C. overnight. After the reaction, washing with a 3% BSA/DBPS mixed solution was performed three times. Next, a 3% BSA/DBPS mixed solution containing secondary antibodies (diluted 500-fold) and Hoechst (nuclear staining reagent, diluted 1,000-fold) was added, and the mixture was reacted at room temperature in the dark for 2 hours and washing with DPBS was performed after the reaction. These were used as the test samples of Examples i2-1 to i2-2, Comparative Examples i2-1 to i2-2, and Positive Control i2.

Data for 1 well was set to n=1, and analysis was performed with a total of 5 wells (n=5). A total number of Hoechst positive nuclei and the number of MHC-positive nuclei were measured, and the Fusion index (% of MHC+ nuclei) was calculated according to the following formula. The average values (n=5) of Fusion indexes are shown in Table 25.

Fusion index (% of MHC+nuclei)=number of MHC-positive nuclei/total number of nuclei×100

As shown in Table 25, in the test samples of Examples i2-1 to i2-2 to which the bagasse decomposition extract was added, compared with the test sample of Comparative Example i2-1 to which no bagasse decomposition extract was added, the Fusion index increased. When a significant difference test (two-sided test according to Student's T test) with Comparative Example i2-1 was performed, the test sample of Example i2-2 had a significantly higher Fusion index (p<0.01) than the test sample of Comparative Example i2-1. Here, as compared with the sample of Comparative Example i2-2, since the Fusion index increased in Positive Control i2, it can be said that the test was performed without any problem.

TABLE 25

| Added | solvent in culture medium | Extract solution in culture medium Type | Concentration (μg/mL) | Fusion index (% of MHC + nuclei) (average value ± standard deviation) |
|---|---|---|---|---|
| Comparative Example i2-1 | — | — | — | 55.1 ± 0.47 |
| Example i2-1 | | Extract A | 1 | 57.8 ± 0.32* |
| Example i2-2 | | | 10 | 57.9 ± 1.33 |
| Comparative Example i2-2 | 1% (v/v) DMSO | — | — | 55.1 ± 0.09 |
| Positive Control i2 | | — | — | 63.7 ± 0.88* |

*Significant increase (p < 0.01)

<Test j: Test for Bone Metabolism Improving Agent>

Test Example j1: Osteoblast Differentiation Promotion Test

[Materials]
In Test Example j1, the following materials were used.
(Cells)
Mouse calvaria-derived cells MC3T3-E1 (Riken Cell Bank, RCB1126)
(Culture Medium)
α-MEM culture medium, 10% FBS, antibiotics added
(Test Reagent)
α-MEM culture medium (phenol red-free, Product No. 41061-029, commercially available from Invitrogen)
Penicillin-streptomycin mixed solution (product name 26253-84, commercially available from Nacalai Tesque, Inc.)
0.25% trypsin-EDTA mixed solution (product name 32777-44, commercially available from Nacalai Tesque, Inc.)
Dulbecco PBS (−) (product name 05913, commercially available from Nissui Pharmaceutical Co., Ltd.)
Alkaline phosphatase activity measurement kit (LabAssay ALP, product name 291-58601, commercially available from Wako Pure Chemical Corporation)
Protein mass measurement kit (Micro BCA Protein Assay Reagent Kit, product name 23235, commercially available from PIERCE)
Cell lysis/protein extraction reagent (Cell-LyEX1, product name 300-34761, commercially available from Wako Pure Chemical Corporation)
10% formalin neutral buffer solution (product name 062-01661, commercially available from Wako Pure Chemical Corporation)
Calcein AM (product name PK-CA707-80011, commercially available from PromoKine)

Recombinant bone morphogenetic protein (Bone Morphogenetic Protein-2 (BMP-2), commercially available from R&D Systems)

[Cell Pre-Culture]

MC3T3-E1 cells were cultivated using a growth culture medium in a T-75 flask (75 cm² U-shaped canted neck cell culture flask, commercially available from Corning Co., Ltd.). The T-75 flask was put into a $CO_2$ incubator (5% $CO_2$, 37° C., wet) and the C2C12 cells were cultured. The culture medium was replaced every other day, and when an 80% confluence was reached, the cells were collected and used for the test.

[Osteoblast Differentiation Promotion Test]

Promoted osteoblast differentiation in MC3T3-E1 cells was confirmed using an alkaline phosphatase (ALP) activity, which is one of osteoblast differentiation markers, as an index.

Pre-cultured MC3T3-E1 cells were adjusted in a culture medium at $1.2 \times 10^5$ cells/0.2 mL/well and seeded in a 48-well plate. The next day, the culture medium was replaced with a culture medium containing 100 μg/mL of the extract A (Example j1-1), a culture medium containing 100 μg/mL of the extract W and 1% (v/v) ethanol (Example j1-2), a culture medium containing no extract (Comparative Example j1-1), a culture medium containing no extract but containing 1% (v/v) ethanol (Comparative Example j1-2), or a culture medium containing BMP-2 (Positive Control j1), and they were cultured for 7 days, for 14 days, and for 21 days. After culturing each day, the cells were washed once with PBS, and each plate was frozen and stored. The culture medium was replaced every 3 to 4 days.

The cells after freezing and storage were washed with PBS and then lysed with a cell lysis agent (Cell-LyEX1 containing 2 mM phenylmethylsulfonyl fluoride (PMSF)) at 100 μL/well. The plate was stirred at room temperature for 30 minutes and then centrifuged, and a solution obtained by diluting the supernatant (5-fold) was used as a measurement sample. The amount of ALP in the cells was measured using an alkaline phosphatase activity measurement kit (LabAssay ALP). In this kit, the ALP activity was measured from the amount of p-nitrophenol per unit protein amount produced within a certain time. The amount of proteins in the solution was measured using a Micro BCA Protein Assay Reagent Kit. The test was performed 5 times, and the average value (n=5) of ALP activities was calculated. The results are shown in Table 26.

As shown in Table 26, compared with Comparative Example j1-1 and Comparative Example j1-2 containing no bagasse decomposition extract, in the samples of Example j1-1 and Example j1-2 containing the bagasse decomposition extract, the ALP activity increased. It can be said that a higher ALP activity indicates further promoted osteoblast differentiation. In addition, when a significant difference test (two-sided test according to Student's T test) with Comparative Example j1-2 was performed, the samples of Example j1-1 and Example j1-2 had a significantly higher ALP activity than the test sample of Comparative Example j1-2 on the 14th day or 21st day of culture. Since the ALP activity also increased in Positive Control j1, it can be said that the test was Performed without any problem.

TABLE 26

| | ALP activity (unit/μg proteins) (average value ± standard deviation) | | |
| --- | --- | --- | --- |
| | On the 7th day | On the 14th day | On the 21st day |
| Example j1-1 | 0.012 ± 0.001 | 0.045 ± 0.002* | 0.025 ± 0.002** |
| Example j1-2 | 0.011 ± 0.001 | 0.041 ± 0.001 | 0.027 ± 0.001* |
| Comparative Example j1-1 | 0.010 ± 0.001 | 0.034 ± 0.001 | 0.011 ± 0.001 |
| Comparative Example j1-2 | 0.010 ± 0.001 | 0.037 ± 0.001 | 0.019 ± 0.002 |
| Positive Control j1 | 0.053 ± 0.006 | 0.217 ± 0.024 | 0.287 ± 0.005 |

*significant increase at $p < 0.01$ with respect to Comparative Example j1-2
**significant increase at $p < 0.001$ with respect to Comparative Example j1-2

Test Example j2: Osteoclast Differentiation Inhibition Test 1

[Materials]

In Test Example j2, the following materials were used.

(Cells)

Human osteoclast precursor cells (commercially available from Cosmo Bio Co., Ltd. PT-267 Lot. RBW-F-OSH-HBV)

(Culture Medium)

Medium for human osteoclast culture, OSCMHB, commercially available from Cosmo Bio Co., Ltd.

(Test Reagent)

Melatonin (M5250, commercially available from Sigma-Aldrich)

TRAP staining kit (AK04F, commercially available from PMC)

[Osteoclast Differentiation Inhibition Test]

Using the above culture medium, 250 μg/mL of a solution containing the extract A was prepared, and this was used as a test solution (Example j2-1).

Figure 11:
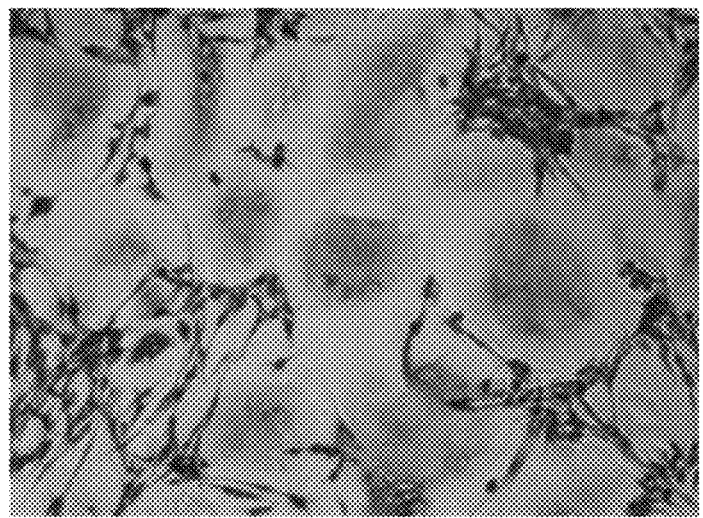
FIG. 11 shows the microscopic observation results of osteoclasts in Test Example j2.
Figure 11:
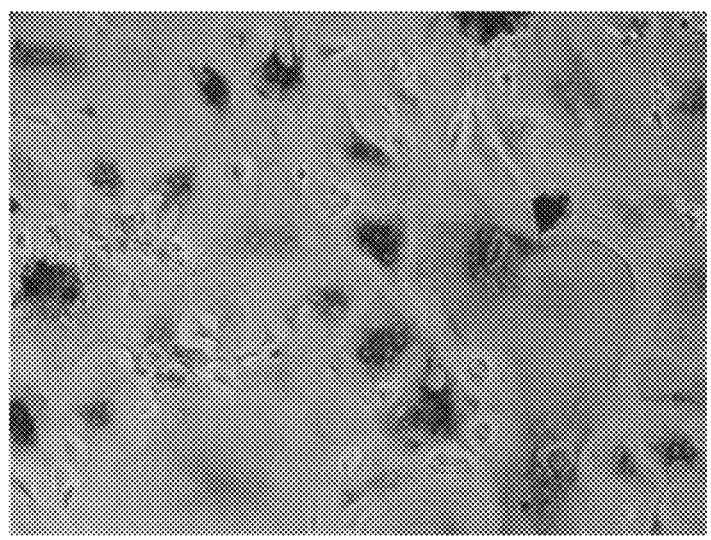
Figure 11:
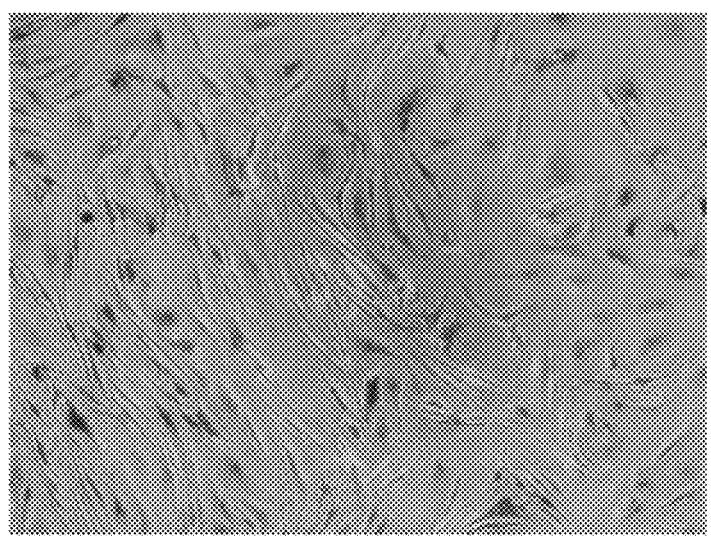

Human osteoclast precursor cells were seeded in a 96-well culture plate at about $0.3 \times 10^5$ cells/50 μl/well. A test solution was added thereto at 50 μL/well and culturing was performed under conditions of 37° C. and 5% $CO_2$ for 7 days. The cultured cells were stained with TRAP using a TRAP staining kit, and observed under a microscope. In the same manner, the same test was performed on a culture medium to which no test solution was added (Comparative Example j2-1) and a culture medium containing 1,000 μM melatonin (Positive Control j2) as a positive control. The results of observation using a microscope are shown in FIG. 11. FIG. 11(a) shows the observation results of Example j2-1, FIG. 11(b) shows the observation results of Comparative Example j2-1, and FIG. 11(c) shows the observation results of Positive Control j2.

As shown in FIG. 11, in Example j2-1, a decrease in the number of multinucleated mature osteoclasts was observed. On the other hand, in Comparative Example j2-1 containing no bagasse decomposition extract, no decrease in the number of osteoclasts was observed. Since a decrease in the number of osteoclasts was also observed in Positive Control j2, it can be said that the test was performed without any problem.

Test Example j3: Osteoclast Differentiation Inhibition Test 2

It is known that, when osteoclasts mature, cells fuse each other and become multinucleated. Therefore, the proportion of mononuclear cells of osteoclasts was measured, and an osteoclast differentiation inhibition effect was confirmed.

Under the same culture conditions as in Example j2-1, human osteoclast precursor cells were cultured using a culture medium containing the extract A with a concentration shown in Table 27 (Example j3-1), a culture medium containing no extract (Comparative Example j3-1), or a culture medium containing melatonin with a concentration shown in Table 27 (Positive Controls j3-1 to j3-2) as positive controls. The proportion of mononuclear cells (%) was calculated by dividing the number of mononuclear cells in the field of view of the microscope by the total number of cells in the field of view. The results are shown in Table 27.

As shown in Table 27, the proportion of mononuclear cells of Example j3-1 containing the bagasse decomposition extract was higher than that of Comparative Example j3-1 containing no bagasse decomposition extract. It can be said that a higher proportion of the mononuclear cells indicates further inhibited differentiation of osteoclasts. Since the proportion of mononuclear cells also increased in Positive Controls j3-1 to j3-2, it can be said that the test was performed without any problem.

TABLE 27

| | Concentration | Proportion of mononuclear cells (%) (average N = 3) | Standard deviation |
|---|---|---|---|
| Example j3-1 | 250 ppm | 89 | 9.0 |
| Comparative Example j3-1 | — | 66 | 9.1 |
| Positive Control j3-1 | 500 µM | 88 | 8.2 |
| Positive Control j3-2 | 1,000 µM | 100 | 0.27 |

The invention claimed is:

1. A deodorant comprising:
a bagasse decomposition extract as an active ingredient, and
a component selected from the group consisting of other deodorants, fragrances, alcohols, surfactants, antibacterial agents, stabilizers, viscosity adjusting agents, pH adjusting agents, preservatives, coloring agents, and combinations thereof;
wherein a decomposed liquid is obtained by subjecting bagasse to at least one decomposition treatment selected from the group consisting of an alkaline treatment at a temperature of 150° C. in a 0.5% (w/w) sodium hydroxide aqueous solution and a hydrothermal treatment using water or water vapor having a temperature higher than 130° C.,
the bagasse decomposition extract is obtained by allowing the decomposed liquid to pass through a column filled with a fixed carrier, removing sugars from the column, and eluting the decomposition extract from the column,
the fixed carrier is a synthetic adsorbing agent or an ion exchange resin.

2. The deodorant according to claim 1,
wherein the fixed carrier comprises a synthetic adsorbing agent, and
the bagasse decomposition extract comprises a fraction obtained by eluting a component adsorbed on the synthetic adsorbing agent in at least one solvent selected from the group consisting of water, methanol, ethanol and a mixture thereof.

3. The deodorant according to claim 1,
wherein the synthetic adsorbing agent comprises an aromatic resin, an acrylic acid-based methacrylic resin, or an acrylonitrile aliphatic resin.

4. The deodorant according to claim 1,
wherein the bagasse decomposition extract comprises a fraction obtained by allowing the decomposed liquid to pass through a column filled with a synthetic adsorbing agent as a fixed carrier and eluting a component adsorbed on the synthetic adsorbing agent in a mixed solvent of ethanol and water,
the synthetic adsorbing agent comprises an unsubstituted aromatic resin,
the column has a temperature of 20 to 60° C., and
the volume ratio of ethanol and water in the mixed solvent (ethanol/water) is 50/50 to 60/40.

5. The deodorant according to claim 1, wherein the component comprises the antibacterial agents.

6. The deodorant according to claim 1, wherein the decomposition treatment comprises the alkaline treatment.

7. The deodorant according to claim 1, wherein the decomposition treatment comprises the hydrothermal treatment.

8. The deodorant according to claim 1, wherein the decomposition treatment further comprises the sub-critical water treatment.

9. A method of producing a deodorant comprising a bagasse decomposition extract, comprising
applying, to bagasse, at least one decomposition treatment selected from the group consisting of an alkaline treatment at a temperature of 150° C. in a 0.5% (w/w) sodium hydroxide aqueous solution and a hydrothermal treatment using water or water vapor having a temperature higher than 130° C. to produce a decomposed liquid,
passing the decomposed liquid through a column filled with a fixed carrier,
eluting the bagasse decomposition extract from the column, and
adding to the bagasse decomposition extract a component selected from the group consisting of other deodorants, fragrances, alcohols, surfactants, antibacterial agents, stabilizers, viscosity adjusting agents, pH adjusting agents, preservatives, coloring agents, and combinations thereof.

10. The method according to claim 9, wherein the decomposition treatment further comprises an alkaline treatment at a temperature higher than 100° C. in an alkaline solution selected from the group consisting of a sodium hydroxide aqueous solution, a potassium hydroxide aqueous solution, and an ammonia aqueous solution.

11. The method according to claim 9, wherein the decomposition treatment comprises the hydrothermal treatment.

12. The method according to claim 9, wherein the hydrothermal treatment is performed with water at 200° C. and under 1.8 MPa of pressure.

13. The deodorant according to claim 1, wherein the hydrothermal treatment is performed with water at 200° C. and under 1.8 MPa of pressure.

14. The method according to claim 9, wherein the decomposition treatment comprises the alkaline treatment.

* * * * *